US006235494B1

(12) United States Patent
Hugli

(10) Patent No.: US 6,235,494 B1
(45) Date of Patent: May 22, 2001

(54) SUBSTRATES FOR ASSESSING MANNAN-BINDING PROTEIN-ASSOCIATED SERINE PROTEASE ACTIVITY AND METHODS USING THE SUBSTRATES

(75) Inventor: Tony E. Hugli, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/246,500

(22) Filed: Feb. 8, 1999

(51) Int. Cl.[7] .................. C12Q 1/37; C12Q 1/00

(52) U.S. Cl. ................. 435/24; 435/4; 435/968; 435/975; 530/300

(58) Field of Search .................. 435/23, 24, 4, 435/968, 975; 530/300

(56) References Cited

U.S. PATENT DOCUMENTS

| 3,884,896 | 5/1975 | Blomback et al. ............... 260/112.5 |
|---|---|---|
| 3,886,136 | 5/1975 | Claeson et al. ................. 260/112.5 |
| 4,016,042 | 4/1977 | Svendsen ........................ 195/103.5 |
| 4,028,318 | 6/1977 | Aurell et al. ................. 260/112.5 R |
| 4,119,620 | 10/1978 | Nagatsu et al. .............. 260/112.5 R |
| 4,147,692 | 4/1979 | Nagatsu et al. .............. 260/112.5 R |
| 4,155,916 | 5/1979 | Smith et al. ..................... 260/345.2 |
| 4,167,449 | 9/1979 | Gargiulo et al. ..................... 435/16 |
| 4,191,808 | 3/1980 | Nagatsu et al. ..................... 435/24 |
| 4,191,809 | 3/1980 | Nagatsu et al. ..................... 435/24 |
| 4,207,232 | 6/1980 | Claeson ............................... 435/23 |
| 4,210,497 | 7/1980 | Loquist et al. ....................... 204/26 |

(List continued on next page.)

FOREIGN PATENT DOCUMENTS

| 0097440 | 6/1983 | (EP) . |
| 9500164 | 1/1995 | (WO) . |

OTHER PUBLICATIONS

Vasta et al, "Developmental and Comparative Immunology", vol. 23(4–5), pp. 401–420, (Abstract only), Jun. 1999.*
Takahashi et al, "International Immunology", vol. 11(5), pp. 859–863, (Abstract Only), May 1999.*
Abou–Ragheb et al., Plasma levels and mode of excretion of the anaphylatoxins C3a and C4a in renal disease, *J. Clin. Lab. Immunol.* 35:113–119 (1991).
Adams et al., Patterns of graft rejection following liver transplantation, *J. Hepatol.* 10:113–119 (1990).
Arlaud et al., A functional model of the human C1 complex, *Immunol Today* 8:106–111 (1987).
Baldwin et al., Complement in organ transplantation, *Transplantation* 59:797–808 (1995).
Bechtel et al., Assessment of soluable adhesion molecules (sICAM–1, sVCAM–1, sELAM–1) and complement cleavage products (sC4d, sC5b–9) in urine, *Transplantation* 58:905–911 (1994).
Berger (1998) Complement–mediated phagocytosis. The human complement system in health and disease.; Volanakis et al. eds., New York: Marcel Dekker, Inc., 12, pp. 285–308.
Bodansky et al. "Peptide Synthesis", Table of Contents, Interscience Publishers (1966).
Bodansky et al., Active esters and resins in peptide synthesis, *Chem. Ind.* (*London*) 38:1597–98 (1966).
Bodansky et al. "The Practice of Peptide Synthesis," Springer–Verlag, Berlin (1984), p. 20.

(List continued on next page.)

*Primary Examiner*—Louise N. Leary
(74) *Attorney, Agent, or Firm*—Stephanie Seidman; Heller Ehrman White & McAuliffe LLP; Dale Rieger

(57) ABSTRACT

Provided herein are assays for measuring in vivo levels of activated mannan-binding protein-associated serine protease (MASP-1 and MASP-2) activity. Also provided are compounds that are useful for assessing the in vivo levels and for monitoring in vitro and in vivo complement-activation (C-activation).

68 Claims, 1 Drawing Sheet

U.S. PATENT DOCUMENTS

| | | | |
|---|---|---|---|
| 4,217,269 | 8/1980 | Cole | 260/112.5 |
| 4,221,706 | 9/1980 | Ali et al. | 260/11.5 R |
| 4,448,715 | 5/1984 | Ryan et al. | 260/112.5 R |
| 4,480,030 | 10/1984 | Svendsen | 435/13 |
| 4,563,305 | 1/1986 | Ryan et al. | 260/112.5 R |
| 4,568,636 | 2/1986 | Svendsen | 435/13 |
| 4,731,336 | 3/1988 | Satoh | 436/506 |
| 5,073,487 | 12/1991 | Lloyd | 435/23 |
| 5,100,899 | 3/1992 | Caine | 514/291 |
| 5,112,952 | 5/1992 | Mallia et al. | 530/387.1 |
| 5,116,735 | 5/1992 | Loesche | 435/34 |
| 5,164,495 | 11/1992 | Lunetta | 540/456 |
| 5,175,083 | 12/1992 | Moulds | 435/7.4 |
| 5,215,899 | 6/1993 | Dattagupta | 435/6 |
| 5,221,616 | 6/1993 | Kolb et al. | 435/18 |
| 5,223,403 | 6/1993 | Loesche et al. | 435/23 |
| 5,225,542 | 7/1993 | Cramer et al. | 530/396 |
| 5,472,939 | 12/1995 | Fearon et al. | 514/8 |
| 5,480,974 | 1/1996 | Morgan et al. | 530/387.9 |
| 5,612,033 | 3/1997 | Tsay et al. | 424/177.1 |
| 5,627,264 | 5/1997 | Fodor et al. | 530/350 |
| 5,679,546 | 10/1997 | Ko et al. | 435/69.2 |
| 5,778,895 | 7/1998 | Barnum et al. | 128/898 |
| 5,807,876 | 9/1998 | Armistead et al. | 514/374 |

OTHER PUBLICATIONS

Bodanszky, Principles of Peptide Synthesis, Second, Revised Edition, Table of Contents, Springer–Verlag.

Bokisch et al., Anaphylatoxin inactivator of human plasma: its isolation and characterization as a carboxypeptidase, *J.Clin.Invest.* 49:2427–2436 (1970).

Bokisch et al., Isolation of a fragment (C3a) of the third component of human complement containing anaphylatoxin and chematotactic activity and description of an anaphylatoxin inactivator of human serum, *J. Exp. Med.* 129(5):1109–30 (1969).

Bone, R.C., The pathogenesis of sepsis, *Ann. Intern. Med.* 115: 457–469 (1991).

Borsos et al., Complement fixation on cell surfaces by 19S and 7S antibodies, *Science* 150(695):505–6 (1965).

Bottger et al., Complement and the regulation of humoral immune responses, *Immunology Today* 8:261–264 (1987).

Boulay, F. et al., Expression cloning of a receptor for C5a anaphylatoxin on differentiated HL–60 cells, 30:2993–2999 (1991).

Brauer et al., The contribution of therminal complement components to acute and hyperacute allograft rejection in the Rat[1,2], *Transplantation* 59:288–293 (1995).

Bronsther et al., Occurrence of cytomegalovirus hepatitis in liver transplant patients, *J. Med. Virol.* 24:423–434 (1988).

Buyon et al., Assessment of disease activity and impending flare in patients with systemic lupus erythematosus, *Arthritis Rheum.* 35:1028–1037 (1992).

Caporale et al., A fluorescent assay for complement activation, *J. Immunol.* 15:1963–1965 (1981).

Chenoweth et al., The C5a receptor of neutrophils and macrophages, *Agents Actions Suppl* 12:252–273 (1983).

Chenoweth et al., Demostration of specific C5a receptor on intact human polymorphonuclear leukocytes, *Proceedings National Academy of Science* 75:3943–3947 (1978).

Cornacoff et al., Primate erythrocyte–immune complex–clearing mechanism, *J. Clin. Invest.* 71:236–247 (1983).

Couser et al., The effects of soluble recombinant complement receptor 1 on complement–mediated experimental glomerulonephritis[1], *J Am Soc Nephrol.* 5:1888–1894 (1995).

Crosbie et al., Studies on stored blood, X. Complement, iso–agglutinins and agglutinogens, *Edinb. Med. J.* 49:766–772 (1942).

Dalmasso et al. The complement system in xenotransplantation, *Immunopharmacology* 24:149–160 (1992).

Davies, J. S. "Amino Acids, Peptides, and Proteins", vol. 29, The Royal Society of Chemistry: Cambridge, U.K. (1997).

Dyker, Amino acid derivatives by multicomponent reactions, *Angew. Chem., Int. Ed. Eng.* 36(16):1700–1702 (1997).

Easton, Free–radical reactions in the synthesis of α–amino acids and derivatives, *Chem. Rev.* 97(1):53–82 (1997).

Ember et al., in *The Human Complement System in Health and Disease,* John E. Volanakis and Michael M. Frank eds. (Marcel Dekker) (1988).

Ember and Hugli, Complement factors and their receptors, *Immunopharmacology* 38:3–15 (1997).

Ember et al., Biologic activity of synthetic analogues of C5a anaphylatoxin, *J. of Immunology* 148(10):3165–3173 (1992).

Epstein et al., The collectins in innate immunity, *Curr. Opin. Immunol.* 8:29–35 (1996).

Feucht et al., Capillary deposition of C4d complement fragment and early renal graft loss, *Kidney Int.* 43:1333–1338 (1993).

Feucht et al., Vascular deposition of complement–split products in kidney allografts with cell–mediated rejection, *Clin. Exp. Immunol.* 86:464–470 (1991).

Frank, M. and Fries, L. Complement. In Paul, W. (ed.) *Fundamental Immunology,* Raven Press, pp. 679–701 (1989).

Fujii et al., New synthetic inhibitors of C1r, C1 esterase, thrombin, plasmin, kallikrein and trypsin, *Biochim. Biophys. Acta* 661:342–345 (1981).

Fujii et al., Defensins promote fusion and lysis of negatively charged membranes, *Protein Science* 2:1301–1312 (1993).

Gerard et al., The chemotactic receptor for human C5a anaphylatoxin, *Nature* 349:614–617 (1991).

Gewruz et al., Interactions of the complement system with endotoxic lipopolysaccharide: consumption of each of the six terminal complement components, *J. Exp. Med.* 128(5):1049–57 (1968).

Gisin, The preparation of merrifield–resins through total esterification with cesium salts, *Helv. Chem. Acta* 56:1476 (1973).

Gordon et al., The antibody crossmatch in liver transplantation, *Surgery* 100:705–715 (1986).

Greene "Protective groups in Organic Synthesis", second edition, Table of Contents, (Wiley–Interscience, 1991).

Hack et al., Elevated plasma levels of the anaphylatoxins C3A and C4a are associated with a fataloutcome in sepsis, *Am.J.Med.* 86:20–26 (1989).

Hecke et al., Circulating complement proteins in multiple trauma patients—correlation with injury severity, development of sepsis, and outcome, *Crit Care Med* 25(12):2015–2024 (1997).

Heideman et al., Anaphylatoxin generation in multisystem organ failure, *J.Trauma* 24 1038–1043 (1984).

Hitomi et al., Inhibition of various immunological reactions in vivo by a new syntehtic complement inhibitor, *Int.Arch.Allergy Appl.Immunol.* 69:262–267 (1982).

Hitomi et al., Inhibitory effect of a new synthetic protease inhibitor (FUT–175) on the coagulation system, *Haemostasis* 15(3):164–168 (1985).

Hourcade et al., The regulators of complement activation (RCA) gene cluster, *Adv. Immunol.* 45:381–416 (1989).

Hugli, *Chemistry and Biology of Thrombin,* Lundblad et al., eds. pp. 345–360, Ann Arbor Science, Ann Arbor (1977).

Hugli et al., 15th International Leucocyte Culture Conference, Asilomar, CA (Abstract) (1982).

Hugli et al., "Immunoassays: Clinical Laboratory Techniques for the 1980s," 443–460 (1980).

Hugli, Structure and function of C3a anaphylatoxin, *Curr. Top. Microbiol. Immunol.* 153:181–208 (1990).

Hugli (1984) Structure and Function of the Anaphylatoxins.; Springer–Verlag, Heidelberg: Springer–Verlag, 7, pp. 193–219.

Hugli et al., Purification and partial characterization of human and porcine C3a anaphylatoxin*, *J. Biol. Chem.* 250:1472–1478 (1975).

Hugli, Human anaphlatoxin (C3a) from the third component of complement, *J. Biol. Chem.* 250:8293–8301 (1975).

Hugli et al., Circular dichroism of C3a anaphylatoxin, *J. Biol. Chem.* 250:1479–1483 (1975).

Hugli et al. in Immune Biology, vol. 14 (Snyderman,R., Ed.), pp. 109–153, Plenum Publishing Company, New York (1984).

Hugli et al. in *Advances in Immunology,* Dixon et al., Eds., pp. 1–53, Academic Press, New York (1978).

Humphrey et al., Chemical synthesis of natural product peptides: coupling methods for the incorporatin of noncoded amino acids into peptides, *Chem. Rev.* 97(6):2243–2266 (1997).

Ikari et al., New synthetic inhibitor to the alternative complement pathway, *Immunology* 49:685–691 (1983).

"IUPAC–IUB Commission on Biochemical Nomenclature. Symbols for amino–acid deriviatives and peptides. Recommendations (1971)", *Biochem. J.* 126:773–780 (1972).

Iwaki et al., Pharmacological studies of FUT–175, nafamostat mesilate. V. Effects on the pancreatic enzymes and experimental acute pancreatitis in rats, *J. Pharmacol.* 41:155–162 (1986).

Ji et al., Activation of the C4 and C2 components of complement by a proteinase in serum bactericidal factor, Ra reactive factor, *J. of Immunology* 150(2):571–578 (1993).

Ji et al., Ancient origin of the complement lectin pathway revealed by molecular cloning of mannan binding protein–associated serine protease from a urochordate, the Japanese ascidian, Halocynthia roretzi, *Immunology* 94:6340–6345 (1997).

Kaiser et al., Color test for detection of free terminal amino groups in the solid–phase synthesis of peptides, *Analyt. Biochem.* 34:595 (1970).

Kapoor A., Recent trends in the synthesis of linear peptides, *J. Pharm. Sci.* 59:1–27 (1970).

Kirschfink et al., Complement activation in renal allograft recipients, *Transplantation Proceedings,* 24:2556–2557 (1992).

Kistler et al., Cardiovascular activating factors from the pancrease, abstract, Biomedical Engineering Society (BMES) Conference, Atlanta, Georgia, Oct. 1999.

Kistler, Erik B., Humoral mechanisms of cellular activation in ischemic shock, A dissertation submitted in partial satisfaction of the requirements for the degree Doctor of Philosophy in Bioengineering, University of California, San Diego (1998).

Kolmer, Preserved citrated blood "banks" in relation to transfusion in the treatment of disease with special reference to the immunologic aspects, *Amer. J. Med. Sci.* 197:442–452 (1993).

Lerner, Richard A., Tapping the immunological repertoire to produce antibodies of predetermined specificity, 299:592–596 (1982).

Lipscombe et al., Distinct physicochemical characteristics of human mannose binding protein expressed by individuals of differing genotype, *Immunology* 85:660–667 (1995).

Lu et al., Binding of the pentamer/hexamer forms of mannan–binding protein to zymosan activates the proenzyme $C1r_2C1s_2$ complex, of the classical pathway of complement, without involvement of C1q, *J. of Immunology* 144(6):2287–2294 (1990).

Malhotra et al., Glycosylation changes of IgG associated with rheumatoid arthritis can activate complement via the mannose–binding protein, *Nature Medicine* 1(3):237–243 (1995).

Manez et al., Anomalous pattern of IgG antibody response to primary cytomegalovirus infection after solid organ retransplantation, *Transplantation* 59:1220–1223 (1995).

Marahiel et al., Modular peptide synthetases involved in nonribosomal peptide synthesis, *Chem. Rev.* 97(7): 2651–2673 (1997).

Mason, Pharmacology of cyclosporine (sandimmune), VII. Pathophysiology and toxicology of cyclosporine in humans and animals, *Pharmacol. Rev.* 42:423–434 (1989).

Matsuda et al., The primary structure of L–1 light chain of chicken fast skeletal muscle myosin and its genetic implication, *FEBS Letters* 126(1):111–113 (1981).

Matsushita and Fujita, Activation of the classical complement pathway by mannose–binding protein in association with a novel C1s–like serine protease, *J. Exp. Med.* 176:1497–1502 (1992).

Matsushita and Fujita, Cleavage of the third component of complement (C3) by mannose–binding protein–associated serine protease (MASP) with subsequent complement activation, *Immunobiol* 194:443–448 (1995).

Matsushita and Fujita, Chapter 8, MASP (MBP–Associated Serine Protease), Collections Innate Immunol., Ezekowitz et al. eds., pp. 165–182 (1996).

Matsushita et al., Complement–related serine proteases in tunicates and vertebrates, *Innate Immunity,* 29–35 (1998).

Maurer et al., Proteins and polypeptides as antiges, *Methods in Enzymology,* 70(A):49–70 (1980).

Mazzoni et al., Mechanisms and consequences of cell activation in the microcirculation, *Cardiovasc Res.* 32(4):709–19 (1996).

McNearney et al., Membrane cofactor protein of complement is present on human fibroblast, epithelial, and endothelial cells, (*1989*) *J. Clin. Ivest.* 84:538:545.

Medof et al., Inhibition of complement activation on the surface of cells after incorporation of decay–accelerating factor (DAF) into their membranes, *J. Exp. Med.* 160:1558–1578 (1984).

Medof et al., Control of the function of substrate–bound C4b–C3b by the complement receptor CR1, *J. Exp. Med.* 159:1669–1685 (1984).

Meuer et al., Comparative study on biological activities of various anaphylatoxins (C4a, C3a, C5a), investigations on their ability to induce platelet secretion[1], *Inflammation* 5:263–273 (1981).

Mitsuoka et al., Inhibition of intestinal proteases decreases cellular activation in SAO shock, abstract, Biomedical Engineering Society (BMES) Conference, Atlanta, Georgia, Oct. 1999.

Moon et al., Complete primary structure of human C4a anaphylatoxin, *J. Biol. Chem.* 256(16):8685–92 (1981).

Mor et al., Late–onset acute rejection in orthotopic liver transplantation—associated risk factors and outcome, *Transplantation* 54:821–824 (1992).

Morgan, Complement fragment C5a and immunoregulation[1], *Complement Today* 1:56–75 (1993).

Morgan et al., Anti–C5a receptor antibodies, *J. of Immunology* 151(1):377–388 (1993).

Morgan et al., Anaphylatoxin–mediated regulation of the immune response, *J.Immunol.* 130:1257–1261 (1983).

Morgan et al., Anaphylatoxin–mediated regulation of the immune response, *J.Exp.Med.* 155:1412–1426 (1982).

Moxley et al., Elevate plasma C3 anaphylatoxin levels in rheumatoid arthritis patients, *Arthritis & Rheumatism* 30:1097–1104 (1987).

Müller Eberhard, Complement[1,2], *Ann Rev Biochem* 38:389–414 (1969).

Müller Eberhard, Molecular organization and function of the complement system, *Ann.Rev.Biochem.* 57:321–347 (1988).

Nicholson–Weller et al., Isolation of a human erythrocyte membrane glycoprotein with decay–accellerating activity for C3 convertases of the complaint system[1], *J. Immunol.* 129:184–189 (1982).

Ochs et al., The role of complement in the induction of antibody responses, *Clin. Exp. Immunol.* 53:208–216 (1983).

Ogata et al., Substrate specificities of the protease of mouse serum Ra–reactive factor, *J. of Immunology* 2351–2357 (1995).

Ohta et al., The mechanism of carbohydrate–mediated complement activation by the serum mannan–binding protein, *J. of Biolog. Chemistry* 285 (4):1960–1984 (1990).

Oppermann et al., Probing the human receptor for C5a anaphylatoxin (C5aR) with anti–peptide antibodies, *Immunobiology* 186(1–2):58 (1992).

Otterness et al., Complement inhibition by amidines and guanidines—in vivo and in vitro results, *Biochem Pharamcol* 27:1873–1878 (1978).

Pfeifer et al., Possible mechanism for in vitro complement activation in blood and plasma samples: Futhan/EDTA controls in vitro complement activation, *Clin Chem.* 45:1190–9 (1999).

Pfeifer et al., Plasma C3a and C4a levels in liver transplant recipients: a longitudinal study, abstract, XVII International Complement Workshop, Rhodes, Greece, Oct. 11–16, 1998.

Pfeiffer et al., Complement activation in EDTA blood–plasma samples may be caused by coagulation proteases, *Techniques in Protein Chemistry VIII*, Marshak, Ed., pp. 363–369, Academic Press, San Diego (1997).

Prizonet et al., Antacids and drug trials for duodenal ulcer, *Lancet* 1:896–897 (1989).

Reich et al., Complement preservation in citrated human blood, *Transfusion* 10:14–16 (1970).

Reid (1998) C1q and mannose–binding lectin. The human complement system in health and disease, Volanakis et al. eds., New York: Marcel Dekker, Inc., 3, p. 33–48.

Reid et al., Complement component CI and the collectins: parallels between routes of acquired and innate immunity, *Immunology Today* 19(2):56–59 (1998).

Reid et al., The protolytic activation systems of complement, *Annu Rev Biochem* 50:433–64 (1981).

Ronholm et al., Complement system activation during orthotopic liver transplantation in man, *Transplantation* 57:1594–1597 (1994).

Sato et al., Molecular characterization of a novel serine protease involved in activation of the complement system by mannose–binding protein, *International Immunology* 6(4):665–669 (1994).

Sauerbrei et al., Enzymatic synthesis of peptide conjugates—tools for the study of biological signal transduction, *Top. Curr. Chem.* 186:65–86 (1997).

Scherer et al., A novel serum protein similar to C1q, produced exclusively in adipocytes, *J. of Biological Chemistry* 270(45):26746–26749 (1995).

Schmid–Schonbein et al., Mechanisms of leukocyte activation in the circulation, *Atherosclerosis* 131:S23–5 (1997).

Schmid–Schonbein, The damaging potential of leukocyte activation in the microcirculation, *Angiology* 44(1):45–56 (1993).

Schmid–Schonbein et al., Perspectives of leukocyte activation in the microcirculation, *Biorheology* 27(6):859–69 (1990).

Schroeder et al., Competitive protein binding assay for biotin monitored by chemiluminescence, *Anal. Chem.* 48:1933 (1976).

Seya et al., Preferential inactivation of the C5 convertase of the alternative complement pathway by factor 1 and membrane cofactor protein (MCP)*, *Mol. Immunol.* 28:1137–1147 (1991).

Seya et al., Purification and characterization of a membrane protein (gp45–70) that is a cofactor for cleavage of C3b and C4b, *Exp. Med.* 163:837–855 (1986).

Seya et al., Functional properties of membrane cofactor protein of complement, *Biochem. J.* 264:581–588 (1989).

Sheriff et al., Human mannose–binding protein carbohydrate recognition domain trimerizes through a triple α–helical coiled–coil, *Structural Biology* 1(11):789–794 (1994).

Sim et al., Kinetics of reaction of human C1–inhibitor with the human complement system proteases C1r and C1s, *Biochem Biophys Acta* 612:433–449 (1980).

Simpson et al., A stable chemiluminescent–labelled antibody for immunological assays, *Nature* 279:646 (1979).

Snover et al., Liver allograft rejection, *Am. J. Surg. Pathol.* 11:1–10 (1987).

Sonntag et al., Anaphylatoxins in fresh–frozen plasma, *Transfusion* 37:798–799 (1997).

Spatola (1983) pp. 267–357 in *Chemistry and Biochemistry of Amino Acids, Peptides, and Proteins,* Weistein, Ed. vol. 7, Marcel Dekker, New York.

Stevens et al., Effects of anti–C5a antibodies on the adult respiratory distress syndrome in septic primates, *J.Clin.Invest.* 77:1812–1816 (1986).

Stewart et al. ("Solid Phase Peptide Synthesis," 2nd Edition, Pierce Chemical Co., Rockford, Illinois (1984), Chapter 2, pp. 27–64.

Stove et al., Circulating complement proteins in patients with sepsis or systemic inflammatory response syndrome, *Clin Diag Lab Immunol* 3:175–183 (1996).

Suankratay et al., Requirement for the alternative pathway as well as C4 and C2 in complement–dependent hemolysis via the lectin pathway, *J. of Immunology* 3006–3013 (1998).

Takayama et al., A 100kDa protein in the C4–activating component of Ra–reactive factor is a new serine protese having module organization similar to C1r and C1s[1], *J. Immunol.* 152:2308–2316 (1994).

Tan et al., Improvements on the purification of mannan–binding lectin and demonstration of its $Ca^{2+}$–independent association with a C1s–like serine protease, *Biochem. J.* 319:329–332 (1996).

Terai et al., Human serum mannose–binding lectin (MBL)–associated serine protease–1 (MASP–1): determination of levels in body fluids and identification of two forms in serum, *Clin. Exp. Immunol.* 110:317–323 (1997).

Thiel et al., The concentration of the C–type lectin, mannan–binding protein, in human plasma increases during an acute phase response, *Clin. Exp. Immunol.* 90:31–35 (1992).

Thiel et al., A second serine protease associated with mannan–binding lectin that activates complement, *Nature* 386:506–510 (1997).

Vallota et al., Formation of C3a and C5a anaphylatoxins in whole human serum after inhibition of the anaphylatoxin inactivator, *J. Exp. Med.* 137(5):1109–23 (1973).

van Son et al., Pulmonary dysfunction is common during a cytomegalovirus infection after renal transplantation even in asymptomatic patients, *Am. Rev. Respir. Dis.* 136:580–585 (1987).

Volanakis and Arlaud, Complement enzymes, Chapter 4, In: The human complement system in health adn disease, Volanakis JE and Frank MM, eds., New York Marcel Dekker, Inc., 4:49–81 (1998).

von Döhren et al., Multifunctional peptide synthetases, *Chem. Rev.* 97(7):2675–2705 (1997).

Wagner and Hugli, Radioimmunoassay for anaphylatoxins: a sensitive method for determing complement activation products in bilogical fluids, *Analytical Biochemistry* 136:75–88 (1984).

Wahlin et al., C3 receptors on human lymphocyte subsets and recruitment of ADCC effector cells by C3 fragments[1], *J. Immunol.* 130:2831–2836 (1983).

Wang et al., Amelioration of lupus–like autoimmune disease in NZB/W $F_1$ mice after treatment with a blocking monoclonal antibody specific for complement component C5, *Proc. Natl. Acad. Sci. U.S.A.* 90:8563–8568 (1996).

Wang et al., Anti–C5 monoclonal antibody therapy prevents collagen–induced arthritis and ameliorates established disease, *Proc. Natl. Acad. Sci. U.S.A.* 92:8955–8959 (1995).

Watkins et al., Nafamostat to stabilise plasma samples taken for complement measurements, *Lancet* 1(8643):896–7 (1989).

Watkins J., Investigation of allergic and hypersensitivity reactions to anaesthetic agents, *Br. J. Anaesth* 59(1):104–11 (1987).

Watson et al. *Molecular Biology of the Gene,* 4th Edition, 1987, The Bejacmin/Cummings Pub. Co., p. 224.

Williams in "Advances in Asymmetric Synthesis", vol. 1, Hassner, A., ed., JAI: Greenwich, CT (1995).

Wuepper et al., Cutaneous responses to human C3 anaphylatoxin in man, *Clin Exp Immunol* 11(1):13–20 (1972).

Yokota et al., Olidomeric structures required for complement activation of serum mannan–binding proteins, *J. Biochem.* 117:414–419 (1995).

Zilow et al., Complement activation and the prognostic value of C3a in patients at risk of adult respiratory distress syndrome, *Clin.Exp.Immunol.* 79:151–157 (1990).

Partrick et al., "Reduced PAF–Acetylhydrolase activity is associated with postinjury multiple organ failure", *Shock* 7(3):170–174 (1997).

Björk et al., Microvascular Effects of Anaphylatoxins C3a and C5a, *Journal of Immunology* 134(2):1115–1119 (1985).

Carney et al., Site–specific mutations in the N–terminal region of human C5a that affect interactions of C5a with the neutrophil C5a receptor, *Protein Science* 2:1391–1399 (1993).

Cui et al., Primary structure and functional characterization of rat C5a: An anaphylatoxin with unusually high potency, *Protein Science* 3:1169–1177 (1994).

Daffern et al., C3a Is a Chemotaxin for Human Eosinophils but Not for Neutrophils I. C3a Stimulation of Neutrophils Is Secondary to Eosinophil Activation, *J. Exp. Med.* 181:2119–2127 (1995).

Ember et al., Induction of Interleukin–8 Synthesis from Monocytes by Human C5a Anaphylatoxin, *American Journal of Pathology* 144(2):393–403 (1994).

Fischer et al., Regulation of B Cell Functions by C3a and $C3a^{desArg}$, *Journal of Immunology* pp. 4279–4286 (1997).

Fukuoka et al., Ligand Binding Sites on Guinea Pig C3aR: Point and Deletion Mutations in the Large Extracellular Loop and Vicinity, *Biochemical and Biophysical Research Communications* 263:357–360 (1999).

Hetland et al., Processing of C5a by human polymorphonuclear leukocytes, *Journal of Leukocyte Biology* 63:456–462 (1998).

Huey et al., Characterizaiton of A C5a Receptor on Human Polymorphonuclear Leukocytes (PMN)[1], *Journal of Immunology* 135(3):2063–2068 (1985).

Morgan et al., Identification and Characterization of the Effector Region Within Human C5a Responsible for Stimulation of IL–6 Synthesis, *Journal of Immnology* 148(12):3937–3942 (1992).

Mousli et al., A Mechanism of Action for Anaphylatoxin C3a Stimulation of Mast Cells, *Journal of Immunology* 148(8):2456–2461 (1992).

Pfeifer et al., Plasma C3a and C4a levels in liver transplant recipients: a longitudinal study, *Immunopharmacoloy* 46(2):163–174 (2000).

Sato et al., Substances Reactive With Mannose–Binding Protein (MBP) In Sera Of Patients With Rheumatoid Arthritis, *Fukishima J. Med. Sci.* 43(2):99–111 (1997).

Scholz et al., C5a–Mediated Release of Interleukin 6 by Human Monocytes, *Clinical Immunology and Immunopathology* 57:297–307 (1990).

Sun et al., Identification of ligand effector binding sites in transmembrane regions of the human G protein–coupled C3a receptor, *Protein Science* 8:2304–2311 (1999).

\* cited by examiner

US 6,235,494 B1

SUBSTRATES FOR ASSESSING MANNAN-BINDING PROTEIN-ASSOCIATED SERINE PROTEASE ACTIVITY AND METHODS USING THE SUBSTRATES

RELATED APPLICATIONS

This application is related to co-pending U.S. application Ser. No. 09/173,579, filed Oct. 15, 1998, to Tony Hugli and Roland Stoughton, entitled "METHODS FOR ASSESSING COMPLEMENT ACTIVATION", and to the continuation-in-part application co-pending U.S. application Ser. No. 09/245,829, filed Feb. 5, 1999, to Tony Hugli and to Roland Stoughton, entitled "METHODS FOR ASSESSING COMPLEMENT ACTIVATION." The subject matter of each of these applications is incorporated herein in its entirety.

FIELD OF THE INVENTION

Provided herein are assays for measuring in vivo levels of activated mannan-binding protein-associated serine protease (MASP-1 and MASP-2) activity. Also provided are compounds that are useful for assessing the in vivo levels and for monitoring in vitro and in vivo complement-activation (C-activation).

BACKGROUND OF THE INVENTION

The complement (C) system of humans and other mammals involves more than 20 components that participate in an orderly sequence of reactions resulting in complement activation. The blood complement system has a wide array of functions associated with a broad spectrum of host defense mechanisms including anti-microbial and anti-viral actions (Müller-Eberhard (1988) *Annu. Rev. Biochem.* 57:321–347; Rother et al. (1984) in Contemporary Topics in Immunology, Vol. 14 (Snyderman, R., Ed.), pp. 109–153, Plenum Publishing Company, New York). Products derived from the activation of C components include non-self recognition molecules C3b, C4b and C5b, as well as the anaphylatoxins C3a, C4a and C5a that influence a variety of cellular immune responses (Hugli et al. (1982) 15th International Leucocyte Culture Conference, Asilomar, Calif. (Abstract); Fujii et al. (1993) *Protein Science* 2:1301–1312; Morgan et al. (1982) *J. Exp. Med.* 155:1412–1426; Morgan (1993) *Complement Today* 1:56–75; Morgan et al. (1983) *J. Immunol.* 130:1257–1261). These anaphylatoxins also act as pro-inflammatory agents (Chenoweth et al. (1983) *Agents Actions* 12:252–273; Hugli et al. (1978) in Advances in Immunology, Dixon et al., Eds., pp. 1–53, Academic Press, New York). The role of C in The C system also has a role in immuno-pathogenesis of a number of disorders, including autoimmune diseases such as rheumatoid arthritis (see, e.g., Wang et al. (1995) *Proc. Natl. Acad. Sci. U.S.A.* 92:8955–8959; Moxley et al. (1987) *Arthritis & Rheumatism* 30:1097–1104), lupus erythematosus (Wang et al. (1996) *Proc. Natl. Acad. Sci. U.S.A.* 93:8563–8568; and Buyon et al. (1992) *Arthritis Rheum.* 35:1028–1037) and acute glomerulonephritis (Couser et al. (1995) *J. Am. Soc. Nephrol.* 5:1888–1894). Other pathologies that involve activation of the C system include sepsis (see, e.g., Stove et al. (1996) *Clin. Diag. Lab. Immunol.* 3:175–183; Hack etal. (1989) *Am. J. Med.* 86:20–26), respiratory distress syndrome (see, e.g., Zilow et al. (1990) *Clin. Exp. Immunol.* 79:151–157; and Stevens et al. (1986) *J. Clin. Invest.* 77:1812–1816) and multiorgan failure (see, e.g., Hecke et al. (1997) *Shock* 7:74; and Heideman etal. (1984) *J. Trauma* 241038–1043). Interest in such pathologies as well as interest in C-activation associated with transplanted organ rejection (see, e.g., Dalmasso et al. (1992) *Immunopharmacology* 24:149–160; Kirschfink et al. (1992) *Transplantation Proceedings* 24: 2556–2557) reveals a need for a reliable and accurate assay system for monitoring in vivo C-activation in patient populations.

The complement system is made up of an array of enzymes and non-enzymatic proteins and receptors. The enzymes include a group of seven serine proteases: factor D, C1r, C1s, MASP, factor B, C2 and factor I. Complement activation occurs by one of three primary modes known as the "classical" pathway, the "alternative" pathway and the lectin pathway (see e.g., Ember et al. (1997) *Immunopharmacology* 38:3–15).

These pathways are distinguished by the processes that initiate complement activation. The classical pathway is initiated by antibody-antigen complexes or aggregated forms of immunoglobulins; the alternative pathway is initiated by several ways, including spontaneous cleavage of a thioester, by certain structures on microbial and cell surfaces, such as amino groups, hydroxyl groups, and by water, and the lectin pathway, which is an antibody-independent pathway that is initiated by the binding of mannan-binding lectin (MBL, also designated mannan-binding protein) to carbohydrates (see, e.g., Thiel et al. (1997) *Nature* 386:506–510).

Complement Pathways

Classical

The classical pathway is initiated by the binding of the first complement component (C1) to immune complexes through C1q, a subcomponent involved in binding to antibody. The c1 complex is composed of C1q and two homologous serine proteases, C1r and C1s (1:2:2 molar ratio). After binding to the immune complexes C1q undergoes a conformational change resulting in the conversions of C1r and C1s to their activated forms. Activated C1s cleaves C4 and C2 to generate a complex of their fragments C4b2a, which in turn cleaves C3 into C3a and C3b. C3b binds to immune complexes.

Alternative

The alternative pathway is activated by microbes without involvement of antibody. C3b molecules generated from C3 by interaction of C3 with two serine proteases, factors B and D, are deposited on the microbial surface where activation of C3 is amplifier. C3b produced by activation of either pathway acts as a central molecule in the subsequent formation of membrane attack complexes that can lyse microbes and also as an opsonin.

Lectin

Another of complement activation, called the lectin pathway (see, Reid (1998) in The human complement system in health and disease; Volanakis et al., Eds., pp. 33–48, Marcel Dekker, Inc., New York) exists. This pathway involves a mannan-binding protein (MBP), also designated mannose-binding lectin (MBL), that is identical to the bactericidal Ra-reactive factor that binds to the Ra polysaccharides on various strains of bacteria (Ji et al. (1993) *J. Immunol.* 150:571–578). MBP is a multi-chain, multi-subunit protein that functions in a similar manner to the C1q component of the classical pathway. There are two proteinases associated with MBL called mannose-binding protein associate serine proteinases or MASP-1 and MASP-2 (see, e.g., Thiel et al. (1997) *Nature* 386:506–510; see, also Takayama etal. (1994) *J. Immunol.* 152:2308–2316). The MBL-MASP-1-MASP-2 complex is activated via MBL binding to neutral sugars resulting in activated MASP-2 enzyme which then cleaves component C4, and possibly the components C2 and C3, to initiate the classical complement pathway.

The collectin MBP, with its associated proteases, has the ability to activate complement and to act as an opsonin (a serum substance, that coats particulates such as viruses to promote phagocytosis). MBP-mediated complement activation is triggered by viruses and other pathogens and stimuli on which neutral sugar residues are exposed (see, Reid et al. (1998) *Immunology Today* 19:56–59). In particular, MBP binds to carbohydrates on microbial and viral surfaces. This pathway differs from the classical and alternative pathways of complement activation. Complement activation via this pathway is mediated by an MBP complex. MBP is associated with serine proteases designated MBP-associated serine proteases (MASP-1 and MASP-2). The complex has C4- and C3-activating capacities upon binding to mannan. The complex contains two serine proteases MASP-1 and MASP-2 linked by a disulfide bond. In this form, MASP is capable of cleaving C4 and C3. The MBP-MASP-mediated complement cascade accompanied by C4 and C3 activation is distinct from the classical and alternative pathways and is designated the lectin pathway.

MBL is structurally related to the complement C1 subcomponent C1q and appears to activate the complement system through an associated serine proteases MASP-1 (see, e.g., Sato et al. (1993) *International Immunol.* 6:66–669) and MASP-2 (see, e.g., Thiel et al. (1997) *Nature* 386:506–510). MBL binds to specific carbohydrate structures on the surface of microorganisms, including bacteria, yeast, parasitic protozoans and viruses, and exhibits antibacterial activity through lytic complement components or by promoting phagocytosis.

Relationships among the pathways

These pathways are important components of host immune response to bacterial and viral infection. The classical pathway attenuates humoral response and is initiated by antibody antigen complexes. The alternative pathway is represents the first line of defense and is activated by a variety of macromolecules, including bacterial lipopolysaccharide, teichoic acids and immune aggregates. Activation of the cascades results in production of complexes involved in proteolysis or cell lysis and peptides involved in opsonization, anaphylaxis and chemotaxis. The following table sets forth biologically active products of complement activation:

| Product | Activity |
| --- | --- |
| C3 | Release of neutrophils from bone marrow |
| C3a | Anaphylatoxin and eosinophil chemotoxin |
| C3b | Mediates phagocytosis of cells via specific lymphocyte receptors, opsonin, co-factor of convertases |
| C4a | Weak anaphylatoxin, spasmogen |
| C4b | Virus neutralization, opsonin, co-factor of convertases |
| C5a | Anaphylatoxin, chemotactic for leukocytes and monocytes |
| C5b-9 | Terminal complement complex (TCC) involved in cell lysis |

Regulatory proteins of the complement system have been identified. Their primary functions are to regulate the activity of C3/C5 convertases for prevention of excessive complement activation and autolytic destruction of host tissues. These complement regulators are either soluble plasma proteins or integral membrane proteins expressed on a variety of cell types. The former include C4b binding protein (C4bp) and Factor H. The latter include the C3b/C4b receptor (Complement receptor 1, CR1, CD35), membrane cofactor protein (MCP, CD46), and decay accelerating factor (DAF, CD55). These proteins possess many structural similarities. Each is composed of multiple short consensus repeats (SCRs) of approximately 60 amino acids in length having conserved cysteine, glycine and proline residues. The genes encoding these proteins have been localized to chromosome 1 and are collectively known as the regulators of complement activation (RCA) gene cluster (Hourcade et al. (1989) *Adv. Immunol.* 45:381). In addition to its role in regulating complement activation, erythrocyte CR1 also functions as a receptor for circulating immune complexes to promote their clearance from plasma (Cornacoff et al. (1983) *J. Clin. Invest.* 71:236).

MCP and DAF proteins prevent autolytic destruction of host tissues by complement activation. MCP (see, Seya et al. (1986) *Exp. Med.* 163:837; Seya et al. (1989) *Biochem. J.* 264:581) binds to C3b and C4b and possesses Factor I cofactor activity. MCP irreversibly inactivate C3b and C4b by proteolytic cleavage to C3bi and C4bi. MCP preferentially binds to C3b, thus making it a more potent inactivator of alternative pathway convertases (Seya et al. (1991) *Mol. Immunol.* 28:1137).

DAF (see, Nicholson-Weller et al. (1982) *J. Immunol.* 129:184) Medofetal. (1984) *J. Exp. Med.* 160:1558) binds to C3b and C4b and dissociates these molecules from the C3 convertase, thus promoting the decay (inactivation) of the convertase. DAF inactivates alternative and classical convertases.

MCP and DAF are composed of only four SCRs, making them the smallest of the complement regulatory proteins. MCP does not possess decay accelerating activity and DAF does not possess cofactor activity. Both proteins are expressed in a variety of cell types, including endothelial cells, fibroblasts, lymphocytes, granulocytes and monocytes (Hourcade et al. (1989) *Adv. Immunol.* 45:381; McNearny et al. (1989) *J. Clin. Invest.* 84:538). MCP and DAF are considered to function, via different complementary mechanisms, as intrinsic inhibitors of complement activation to prevent complement-mediated autolysis of host cells.

Although the pathways converge to produce $C_{5-9}$, they are distinguishable. In the alternative pathway, the cleavage of the $C_3$ component of complement into its C3a and C3b fragments is one of the significant events signalling activation of the alternate complement cascade. Following the conversion of C3a, a C5 convertase enzyme complex is formed. This enzyme cleaves the C5 component to yield the fragments C5a and C5b. Complement activation by the classical pathway mechanism is uniquely characterized by the fact that this route leads to the conversion of the C4 to its fragments C4a and C4b.

The physicochemical and physiological properties of each of the cleavage products C3a, C4a and C5a, termed anaphylatoxins, are known. Each is a potent bioactive polypeptide and plays a key role as a mediator of acute inflammatory processes. Among the three anaphylatoxins, C5a is characterized by its ability to interact with white blood cells. C3a and C4a are rendered spasmogenically inactive in vivo by conversion of the respective des arginine derivatives (C3a des Arg or C3ai C4ai des Arg or C4ai) by a serum carboxypeptidase. Human C5a is converted to C5a des Arg by this serum carboxypeptidase.

Conversion of the human complement components C3 and C5 to yield their respective anaphylatoxin products has been implicated in certain naturally occurring pathologic states including: autoimmune disorders such as systemic lupus erythematosis, rheumatoid arthritis, malignancy, myocardial infarction, Purtscher's retinopathy, sepsis and adult respiratory distress syndrome. In addition, increased circulating levels of C3a and C5a have been detected in certain conditions associated with iatrogenic complement activation such as: cardiopulmonary bypass surgery, renal dialysis, and nylon fiber leukaphoresis. Elevated levels of C4a anaphylatoxin is associated with the autoimmune disorders mentioned above.

Regardless of which initiation pathway is used, the end result is the formation of activated fragments of complement proteins (e.g. C3a, C4a, and C5a anaphylatoxins and $C_{5b-9}$ membrane attack complexes). These fragments mediate several functions including leukocyte chemotaxis, activation of macrophages, vascular permeability and cellular lysis (Frank, M. and Fries, L. Complement. In Paul, W. (ed.) Fundamental Immunology, Raven Press, 1989).

Therefore, the ability to quantitatively measure the circulating levels of these anaphylatoxins or their des-Arg derivatives would be of utility in diagnosing a variety of important pathological conditions. Additionally, the ability to measure levels of C4a and C4a des Arg permits determination of the pathway by which complement activation occurs, thereby permitting a determination of the precise mechanism of complement activation and also whether natural immunological defense mechanisms are functional.

Various methods for measuring C3a, C4a, C5a and their des Arg derivatives are known (see, Hugli et al (1980) in "Immunoassays: Clinical Laboratory Techniques for the 1980s," 443–460, Alan R. Liss, Inc., New York, N.Y. and Wagner et al. (1984) *Analyt. Biochem.* 136:75–88) for an RIA method; (see, Caporale et al. (1981) *J. Immunol.* 15:1963–1965) for a fluorescence-based assay. Commercial kits are also available from, for example, Amersham (see, U.S. Pat. No. 4,731,336).

Neither of the major C-activation pathways (i.e. the classical and alternative pathways), however, can function in the presence of the metal chelator EDTA (see, e.g., Müller-Eberhard (1969) *Ann. Rev. Biochem.* 38:389–414). Drawn EDTA blood samples exhibit extensive in vitro C-activation, complicating the development of accurate assay systems and has impeded the development of a reliable complement assay for research and clinical applications.

In vitro C Activation

Since the discovery of the C system, "spontaneous" loss of C activity in serum or plasma samples stored in vitro has remained a problem. Early definitions of the complement system invariably included a statement about the lability of C present in serum or plasma stored at 4° C. or at room temperature (22° C.) (see, e.g., Reich et al. (1970) *Transfusion* 10:14–16; Kolmer (1939) *Amer. J. Med. Sci.* 197:442–452; Crosbie et al. (1942) *Edinb. Med. J.* 49:766–772). The storage of serum and plasma samples under conditions allowing for the retention of full C activity has always been a problem for basic research and clinical laboratories. This has been solved in part by addition of EDTA to blood, serum and plasma.

The utility of complement (C) assays has been minimized by an inability to stabilize C components in blood or plasma samples and prevent in vitro activation. It is known that C3a and C4a levels in EDTA plasma from certain patients (i.e. autoimmune, trauma, sepsis and organ transplant patients) are greatly elevated but unreliable due to in vitro activation. Even EDTA plasma from normal individuals continues to undergo low level C-activation, particularly cleavage of component C4 to C4a and C4b. EDTA blood samples require immediate processing and analysis of the plasma to avoid further time-dependent C-activation. In designing a routine diagnostic C assay for the clinical laboratory, sample stabilization becomes a key issue. Consequently, understanding the mechanism of in vitro C-activation is as important as developing a method to control it.

Assays for MASP activity

Co-pending U.S. application Ser. No. 09/173,579, and its continuation-in-part U.S. application Ser. No. (attorney docket no. 24730-2203B), filed Feb. 5, 1999, which are noted above, are herein incorporated by reference, identify MASP activity as the agent responsible for in vitro complement activation in plasma containing a metal chelator, such as EDTA or citrate. It is shown therein that MASP, particularly MASP-2, is activated in the complex MBL-MASP complex, but that the activated enzyme when complexed, is not active in fluid phase on the substrates C3 and C4. Addition of a chelator, particularly a divalent metal ion chelator, such as citrate or EDTA, in vitro permits the activated MASP in the complex to cleave its substrates.

It is the activity of in vivo activated MASP in vitro in the presence of a chelator, that results in the observed in vitro complement activation. The observed increase in, for example, C4a concentration in EDTA plasma is a reflection of the amount of activated MASP enzyme in the complex when the blood was drawn. Exposure to EDTA or other agent that binds to divalent metal ions, particularly calcium ions, allows for measurement of the activated MASP that was in the complex in vivo. Therefore, in order to measure such activity, and to thereby monitor diseases for which MASP activity, particularly MASP-2 activity, is an indicator, the rate or amount of C3a and C4a increase over time in plasma containing a metal chelator, such as EDTA or citrate, can be measured.

Monitoring MASP, particularly MASP-2, activity in plasma, containing a metal chelator, such as EDTA or citrate, provides an indicator of in vivo activation of the lectin pathway. In vitro MASP activity can be correlated with any event that exposed neutral sugars to the complex in vivo, such as viral and parasitic diseases and tissue and organ injury, including transplanted organs. Activated MASP (that was in the complex) is assessed by measuring the increase in C3a and C4a in plasma, containing a metal chelator, over time or by measuring the amount compared to a standard or a control. The increase in C3a and C4a in the plasma, containing the chelator, or relative amount above a control or standard in the plasma, containing the chelator, is an indicator of MASP activating factors, such as pathogens, including viruses, particularly coated viruses, and parasites, and tissue injury to which the plasma was exposed in vivo.

In those methods, MASP activity is measured by measuring C3a and C4a levels in in vitro activated plasma, containing EDTA or other metal chelator, using standard methods, such as a commercially available kits, as index of the enzyme activity. The increase in C3a and C4a as a function of time or the relative amount of either compared to a control or standard is an indicator of the amount of activated MASP in the plasma at the time the blood was drawn.

Also provided in the co-pending applications are methods for evaluating activation of the alternative and/or classical pathways without interference from the lectin pathway. In practicing these methods, an effective amount of a MASP-specific inhibitor, particularly Futhan (6-amidino-2-naphthyl p-guanidinobenzoate dimethanesulfonate), is added to a plasma sample, containing a metal chelator, such as EDTA. The amount of inhibitor is selected to be an amount that inhibits substantially all MASP activity exposure of the MBL-MASP complex to an appropriate chelator. In the presence of this inhibitor, levels of C3a or C4a are measured. Generation of C4a under these conditions signals conversion of C4, which is indicates activation of the classical pathway. Formation of C3a in the absence of C4a indicates activation of only the alternative pathway.

The co-pending U.S. applications, thus, provide general methods for assessing in vivo complement activation and thereby identifying certain disorders associated therewith. Although these assays are quite useful, improvements in the assays and methods provided in the co-pending applications would be desirable.

It is an object herein to provide such improvements. In particular, it is an object herein to provide assays for assessing in vivo activated MASP. It is also an object herein to provide substrates for these assays and to thereby more directly measure MASP activity.

SUMMARY OF THE INVENTION

The assays of interest herein, include the following:

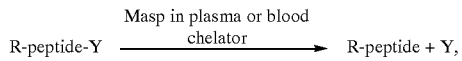

R-peptide-Y $\xrightarrow{\text{Masp in plasma or blood, chelator}}$ R-peptide + Y, where the peptide is a any peptide cleavable by mannan-binding protein-associated serine protease (MASP) or is a peptide or peptide analog provided herein; the Y is a group that includes a tag that is any detectable label, such that cleavage can be assessed. The peptide is added to a sample of blood or plasma that contains an inhibitor of complement pathway convertases (other than a MASP enzyme), such as a calcium chelator, including EDTA, citrate or the equivalent. R is a protecting group, or a capping group or any suitable C-terminal group, such as Cbz, Boc, FMoc, and Ac, or it is additionally or alternatively a tag that will change properties upon cleavage of Y. For example, a combination of a fluorescent moiety, such as 2-methyl-anthranilic acid, whose fluorescence is quenched by the C-terminus or C-terminal moiety, such as pNA can be used. Upon cleavage, fluorescence of the anthranilic acid-labeled peptide can be detected and/or the change in O.D. resulting from cleavage of the pNA can be measured. Other such pairs of tags can be identified. In addition, the method can be generalized and applied to any protease assay.

The tag or tags is (are) selected such that cleavage results in a detectable change in the assay mixture. For example, the tag is selected to undergo a change in fluorescence, or color when cleaved. Generally, the C-terminal is blocked with Ac, Boc or other suitable moiety, and a tag that is detectable upon cleavage or that renders cleavage detectable is added on the C-terminus. The resulting products are detected fluorimetrically, calorimetrically or using any method appropriate for the selected tags.

The peptide is any peptide that comprises a sufficient number of amino acids from the C-terminus of a C3a, C4a, C5a or other convertase substrate to be recognized and cleaved, releasing Y. The tag or cleaved moiety is linked to the residue from which cleavage is effected, typically an Arg, and also a Lys, for MASP enzymes via n amide bond.

Among the preferred substrate compounds are those of formula Blocking group-P5-P4-P3-P2-P1-tag, where, in more preferred embodiments:

P1 is Arg or Lys or, preferably, Arg;

P2 is Ala, Gly, Gln, Leu, Asn, Thr, Ala, or Nle preferably Gln, Asn, Thr, Ala, or Nle;

P3 is Gly, Gln, Leu is preferably Leu and is optional;

P4 is preferably Gly, and can be optional;

P5 can almost any group and can be replaced by a bulky blocking group, such as Cbz;

P1-P5 are preferably the L-isomer;

Ac (acetyl) is among the preferred blocking groups, but can be replaced by an N-terminal blocking group, particularly any that does not markedly change the cleavage rate of the enzyme, or can be a fluorescent label, particularly one whose fluorescence is quenched by the selected tag; and the tag, which is linked via an amide, ester or thioether bond or other such MASP-cleavable bond is any detectable label, including calorimetric, bioluminescent, fluorescent, radiolabels and enzyme labels that can be monitored upon cleavage. Among the preferred tags are colorimetric or chromogenic tags, such as pNA (para-nitroaniline) and fluorescent tags that for which the absorption or emission spectra change upon cleavage. Other tags that, upon cleavage, can react with other substrates, are also contemplated herein.

Thus the substrates include preferably 4 or 5 amino acids, but can include three or two amino acids (or suitable anlogs thereof), such as a compound including Leu-Ala-Arg, such as Ac-Leu-Ala-Arg-Y.

To assess in vivo MASP activation, the assay is run in the presence of a metal ion chelator, particularly a divalent metal ion chelator, such as citrate or EDTA, which is necessary to observe MASP activity in fluid phase, such as plasma or blood. The MASP enzyme assessed includes MASP-2, MASP-1 or mixtures thereof, and is typically primarily or exclusively MASP-2. This assay provides a means for assessing in vivo complement activation, and particularly activation of the lectin pathway.

The above assays may also be performed in the presence of a serine protease inhibitor, such as Futhan, which blocks any MASP activity. Such assay can serve as a negative control for the assays herein. Also, an ELISA for detecting total MASP, can be performed in connection with these assays. This value can serve to normalize the results. The results from the instant assay can be reported as a ratio of the activity or amount determined therefrom compared to total MASP.

Substrates that are useful in methods for assessing in vivo mannan-binding protein-associated serine protease (MASP-1 and MASP-2) activity and for monitoring in vitro and in vivo complement-activation (C-activation) are provided. Substrates for assessing activation of the classical and alternative pathways are also provided.

The substrates provided herein may also be used in assays to assess classical and alternative pathway activation. Reacting the substrates with plasma or serum in the presence of a serine protease, which inhibits MASP activity, can assess in vivo activation of the classical and alternative pathways.

Longer peptides that include the above peptides are also contemplated. Thus, the compounds are pentapeptides, hexapeptides, heptapeptides, etc., or analogs thereof, that are suitable substrates for MASP-1 or MASP-2, such that cleavage occurs at the C-terminal residue resulting in release of the tag.

The compounds for use as substrate in the methods described herein may be shorter peptides and peptide analogs (i.e., tetrapeptides (P1-P4), tripeptides (P1-P3), dipeptides (P1-P2), or amino acids (P1) or analogs thereof). In these embodiments, the compounds are versions of the compounds exemplified herein but are truncated at the N-terminus, and retain the C-terminus requisite for MASP activity. For example, the compounds only may contain the P1-P4 units, contain a C-terminal tag and preferably are capped at the N-terminus It is also to be understood that the compounds may be longer peptides and peptide analogs. The compounds may contain substantially all of the amino acids of a C3a, C4a or C5a proteins (see, e.g., SEQ ID NOS. 1 through 14, which set forth sequences from different species), up to, but, preferably not including, the full-length protein, labeled with a detectable tag at the C-terminus and/or with a tag at the N-terminus that changes properties, i.e., is detectable, upon cleavage and a cleavable group at the C-terminus. In these embodiments, the compounds contain the C-terminal portion of the protein, and also possess at least 4, but less than 76, preferably less than 70, more preferably less than 60, particularly less than 50, more preferably less than 25, amino acid residues or analogs thereof, including the site cleaved by MASP.

Particularly preferred, are compounds that contain the C-terminal portion of a C3a, C4a or C5a peptide and possess 5–10, preferably 5–7, most preferably 5, amino acid residues or analogs thereof.

Among the presently preferred substrates are:
Ac-Ala-Gly-Leu-Gln-Arg-pNA (SEQ ID NO. 15);
Ac-Ala-Gly-Leu-Asn-Arg-pNA (SEQ ID NO. 16);
Ac-Ala-Gly-Leu-Thr-Arg-pNA (SEQ ID NO. 17);
Ac-Ala-Gly-Leu-Nle-Arg-pNA (SEQ ID NO. 18); and
Ac-Ala-Gly-Leu-Gly-Arg (SEQ ID NO. 19).

Also among the preferred substrates are those in which Ac and pNA are replaced by other suitable groups. Ac may be replaced by any suitable blocking group or by a fluorescence moiety whose fluoroescence is quenched in the presence of pNA. pNA may be replaced by any suitable detectable moiety detected upon cleavage from the molecule.

Compounds for use in the methods described herein may be concatamers of the compounds described herein. In these embodiments, the compounds are, for example, 10-mers, 15-mers, 20-mer, etc., containing repeating units of the pentapeptides described herein. Other concatamers, such as those of dimers, trimers, tetramers, hexamers, heptamers, etc., are also included in the compounds for use in the methods described herein.

In all embodiments described herein, compounds that are suitable substrates for MASP-1 or MASP-2 may be identified empirically using the assays provided herein. In addition, certain of the compounds described herein may exhibit species selectivity in complement activation assays. This allows the methods described herein to be optimized for a given species.

In certain embodiments, the compounds for use in methods that determine the level of complement activation have formula (I):

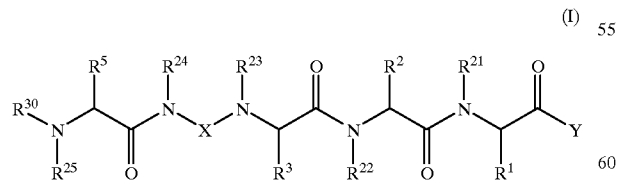

(I)

or analogs thereof, where

R$^1$ is R$^{60}$-A, where A is NH$_t$(R$^{40}$)$_{3-t}$, heterocyclyl, heteroaryl, guanidinyl, amidino or imino, and is capable of forming a cationic salt at about physiological pH, or is N$^+$(R$^{40}$)$_4$;

R$^{60}$ is alkylene, alkenylene, alkynylene, cycloalkylene, heterocyclylene, aralkylene, heteroaralkylene, arylene or heteroarylene;

R$^{40}$ is alkyl, alkenyl, alkynyl, aryl or heteroaryl;

t is 0–3;

R$^{21}$ is H or alkyl;

X is a group that allows for flexibility in the chain, preferably alkylene, alkenylene or CH(R$^4$)C(O), preferably where the alkyl portion is contains from 1 or 2 carbons up to about 20, more preferably 1 or to up to about six, where the chain is preferably straight;

R$^2$, R$^3$, R$^4$, R$^5$, R$^{22}$, R$^{23}$, R$^{24}$, R$^{25}$ and R$^{30}$ are each independently selected as in (i) or (ii) as follows:
(i) R$^2$, R$^3$, R$^4$ and R$^5$ are each independently selected from a side chain of a naturally occurring α-amino acid, H, alkyl, preferably lower (C$_{1-6}$) alkyl, alkenyl, preferably C$_{2-10}$ alkenyl, alkynyl, preferably C$_{2-6}$ alkynyl, aryl, aralkyl, aralkenyl, aralkynyl, heteroaryl, heteroaralkyl, heteroaralkenyl, Z$^1$-substituted aryl, aralkyl, aralkenyl or aralkynyl, and Z$^2$-substituted heteroaryl, heteroaralkyl or heteroaralkenyl;

Z$^1$ is selected from halogen, lower alkyl, lower alkoxy, OH, haloalkyl, preferably CF$_3$, NO$_2$, nitrile, alkylthio, phenyl and —NNR'R";

each of R' and R" is independently H, alkyl, preferably lower alkyl, OH or halo lower alkyl, particularly CF$_3$;

Z$^2$ is lower alkyl, preferably C$_{1-4}$ alkyl, or halo lower alkyl, preferably C$_{1-4}$ haloalkyl, more preferably CF$_3$;

R$^{22}$, R$^{23}$ and R$^{24}$ are each independently H or alkyl; and

R$^{30}$ and R$^{25}$ are each independently selected as in (a), (b) or (c) as follows:
(a) R$^{30}$ is a peptide residue containing any number of residues, particularly, from 1 to 71, preferably 1–65, more preferably 1–55, particularly 1–45, more preferably 1–20 or 1–5, most preferably 1–2, amino acid residues, whereby the resulting compound contains at least the two, preferably 4 or 5 amino acid residues of the C-terminal portion of any C4a, C5a, C3a (see, e.g., SEQ ID NOS. 1 through 14, preferably SEQ ID NOS. 1 through 9, more preferably SEQ ID NOS. 6 through 9, most preferably SEQ ID NO. 6), preferably a C4a protein and is cleavable by MASP, and R$^{25}$ is H or alkyl; or
(b) R$^{30}$ and R$^{25}$ are each independently H, C(O)R$^{10}$, alkyl, alkyl-C(O)R$^{10}$, alkenyl, alkynyl, aryl, heteroaryl, aralkyl, heteroaralkyl, Si(R$^{10}$)$_3$, S(O)$_m$ R$^{10}$ where m is 0–2 or P(O)$_n$(R$^{10}$)$_p$ where n is 0–3; p is 1–2; R$^{10}$ is alkyl, aryl, heteroaryl, aralkyl, heteroaralkyl, alkoxy, aryloxy, heteroaryloxy, aralkoxy, heteroaralkoxy or NR$^{11}$R$^{12}$; and R$^{11}$ and R$^{12}$ are each independently selected from among H, alkyl, aryl, heteroaryl, aralkyl and heteroaralkyl; or
(c) R$^{30}$ and R$^{25}$, together with the nitrogen atom to which they are attached, form a heterocyclyl, heteroaryl, cyclic amide or cyclic imide group; or
(ii) R$^2$ and R$^{22}$, and/or R$^3$ and R$^{23}$, and/or R$^4$ and R$^{24}$, and/or R$^5$ and R$^{25}$ together form alkylene, preferably ethylene, propylene, butylene or pentylene, more preferably propylene; and the remainder of R$^2$, R$^3$, R$^4$, R$^5$, R$^{22}$, R$^{23}$, R$^{24}$, R$^{25}$ and R$^{30}$ are selected as in (i);

Y includes a detectable tag group detectable by radiolabelled, photochemical, colorimetric, chromogenic, fluorescent, fluorogenic, phosphorescent, electrochemical, chemiluminescent or bioluminescent methods, as described in detail below; and $R^1, R^2, R^3, R^4, R^5, R^{25}, R^{30}$, X and Y are unsubstituted or are substituted with one or more substituents selection from Q, which, as defined herein, is halogen, hydroxy, nitrile, nitro, formyl, mercapto, carboxy, hydroxysulfonyl, hydroxyphosphoryl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl, or any two Q groups substituting adjacent atoms on an aryl or heteroaryl group may form 1,3-butadienylene, 1-aza-1,3-butadienylene or 2-aza-1,3-butadienylene.

$R^{30}$ may also include a tag group and can be a moiety selected such that cleavage of Y is detectable. For example, $R^{30}$ and Y may be selected such that one or the other or both is a fluorescent group or colorimetrically detectable group upon cleavage of Y.

Also provided are species-specific assays for determination of the level of complement activation by MASP-1 or MASP-2. Such assays are optimized by selection of a compound provided herein that exhibits selectivity for the species.

Kits containing the compounds provided herein are also provided. The kits contain a compound provided herein, instructions for performing the assay. In addition the kits can contain one or more of an (ii) assay buffer, preferably phosphate-buffered saline (PBS); (iii) a serine protease inhibitor, preferably Futhan (6-amidino-2-naphthyl p-guanidinobenzoate dimethane-sulfonate) or dilute acetic acid, used as reaction stop solution; (iv) trypsin or used as a standard; (v) a substrate or container for performing the assay, such as microtiter plate, such as a 96-well or higher density (i.e., 384 wells or more) microtiter plate; and, optionally (vi) a calcium chelator, including, but not limited to, ethylenediamine tetraacetic acid (EDTA) or citrate or other agent the removes calcium from the blood or plasma sample; (vi) control and other such components. The kit may also contain or be combined with an ELISA kit for assessing total MASP activity. The kits are used in the assays provided herein to assess the level of complement activation by the lectin pathway in a test sample. Such activation indicates, for example, that the source of the text sample has a condition, including, but not limited to, parasitic or viral infection, organ transplant rejection, including, but not limited to, acute organ transplant rejection, chronic rejection or incipient rejection, inflammatory response, autoimmune disease, including, but not limited to, rheumatoid arthritis or system lupus erythematosus (SLE), or tissue injury.

DETAILED DESCRIPTION OF PREFERRED EMBODIMENTS

A. Definitions

Figure 1:
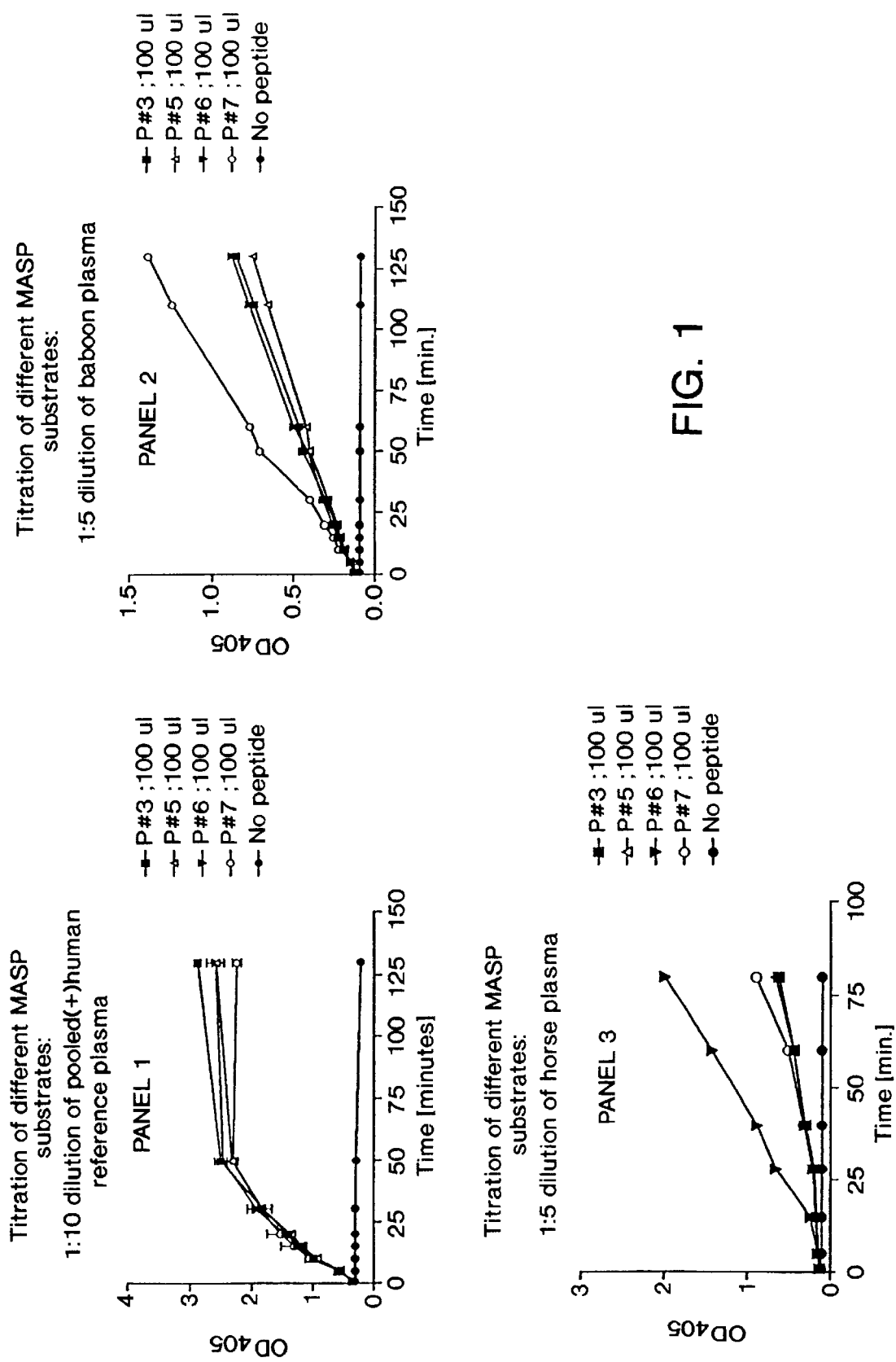
FIG. 1 sets forth the results of exemplary assays (see Example 1) using various sources of plasma and several exemplary substrates as follows: P#3 is Ac-Ala-Gly-Leu-Gln-Arg-pNA; P#5 is Ac-Ala-Gly-Leu-Asn-Arg-pNA; P#6 is Ac-Ala-Gly-Leu-Thr-Arg-pNA; and P#7 is Ac-Ala-Gly-Leu-Nle-Arg-pNA; panel 1 shows titration of various substrates using a 1:10 dilution of pooled human plasma; panel 2 (reading from left to right) shows titration of various substrates using a 1:5 dilution of a sample of baboon plasma; and the panel three (bottom right) shows titration of various substrates using a 1:5 dilution of a sample of horse plasma.

Unless defined otherwise, all technical and scientific terms used herein have the same meaning as is commonly understood by one of skill in the art to which this invention belongs. All patents, patent applications and publications referred to herein are incorporated by reference in their entirety.

As used herein, MBP (mannose binding protein) is also designated mannose-binding lectin (MBL).

As used herein, an inhibitor that specifically inhibits mannan-binding protein-associated serine protease (MASP), inhibits the activity of a MASP, but does not substantially inhibit the activity of other enzymes in the complement activation pathways.

As used herein, CR1 is complement receptor type 1, which is the C3b/C4b receptor. Complement receptor 1 (CR1 or CD35) is found on erythrocytes as well as a select group of leukocytes, including lymphocytes, neutrophils, and eosinophils. CR1 is a 190–280 kDa transmembrane protein that triggers the proteolytic degradation of membrane bound C3b molecules with which it comes in contact. It also promotes the clearance of immune complexes.

As used herein, C-activation refers to activation of complement pathways.

As used herein, cell activation refers to changes in and interactions among circulating white blood cells, including leukocytes, cells lining blood vessels, including endothelial cells, and platelets. These changes are evidenced by increased "stickiness" of cells, changes in shapes of cells, free radical production and release of inflammatory mediators and enzymes. Activated cells project large pseudopods, and express adhesion molecules on their surfaces. For example, adhesion molecules and villi attach macrophage and monocytes to endothelium. Macrophage and monocytes may then infiltrate into tissue outside the blood vessel beginning the development of atherosclerosis, venous insufficiency ulcers an diabetic retinopathy.

Cell activation is necessary for normal human immune defense mechanisms, but inappropriate or excessive activation leads to or participates or intensifies many diseases, including, but not limited to: arthritis, atherosclerosis, acute cardiovascular incidents, Alzheimer's Disease, hypertension, diabetes, venous insufficiency, autoimmune disease and others. Cell activation is a major contributor to rejections processes in organ transplants, and to predisposition to poor outcomes in trauma and high risk surgeries.

For example, LPS (lipopolysaccharide) binds to immunoglobin M and this complex activates the complement system with the release of C3b, which material in turn activates the polymorphonuclear leukocytes (PMN), monocytes, neutrophils, macrophage and endothelial cells. The activation of these substances stimulates the release of several mediators of septic shock including tumor necrosis factor (TNF-α) interleukin-1 (IL-1) and other interleukins including IL6 and IL-8, platelet-activating factor (PAF), prostaglandins and leukotrienes (see, e.g., (1991) *Ann. Intern. Med.* 115: 464–466 for a more comprehensive listing). Of these, the two cytokines TNF-α and IL-1 lead to many of the physiologic changes which eventuate into septic shock.

The LPS-stimulated macrophages also release other free-radicals, including oxyfree-radicals from arachidonic acid metabolism, which free-radicals can also cause extensive damage to endothelial cells. These lead to aggregation and circulatory collapse, which in turn leads to hypotension, tissue damage, multi-organ failure and death. Thus, excess production of the above mentioned free-radicals is linked to the mortality associated with septic shock.

As used herein, polymorphonuclear leukocytes (PMNs). Polymorphonuclear neutrophil granulocytes (PMN) are cells which are mobilized during inflammatory phenomena and which can be stimulated by various compounds, such as, for example, formylmethionyl-leucyl-phenylalanine (FMLP) or prostaglandins E (PGE1). The PMN granulocytes respond to these extracellular stimuli with an activation of the oxygen metabolism with release of toxic oxygenated metabolites. An excessive response of the PMN granulocytes may be the cause of a painful inflammation and is also accompanied by a reduction in the level of cyclic adenosine monophosphate (cAMP) in these granulocytes.

As used herein, EDTA plasma refers to plasma produced from blood drawn into standard containers, such as tubes that contain EDTA. For examples, tubes containing about 5 mg of $Na_2$-EDTA were designed for collecting 2.5–5.0 ml of blood. It is understood that other suitable chelating agents, particularly calcium chelators, can be used in place thereof. Such agents include, but are not limited to: citrate, polycarboxylic acid chelating agents, such as alkylene polyamine polyacetic acids of the formula:

$(HOOCCH_2)2N[(CH_2)_nN(CH_2COOH)]_mCH2COOH$, where n is 1,2,3 or 4 and m is 0,1,2,3, or 4, up to two of the carboxymethyl groups may be replaced with a beta-hydroxyethyl group and one or more of the carboxymethyl groups may be replaced by carboxyethyl groups. Specific examples of such polyacetic acids which are particularly suitable include N-hydroxyethylethylenediaminetriacetic acid, nitrilotriacetic acid, N-2-hydroxyethyliminodiacetic acid, diethylenetriamine-pentaacetic acid, and mixtures thereof.

As used herein an effective amount of a compound or composition for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptoms.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, a control refers to a sample that is substantially identical to the test sample, except that it is not treated with a test parameter, or, if it is a sample plasma sample, it may be from a normal volunteer not affected with the condition of interest; or a control also may be an internal control. For example, if the level of MASP activity is being measured, then it can be measured by determining the rate of increase of cleavage of the substrate or as a relative amount at a particular time point, which time point is selected to be during the linear increase in the component or as an absolute amount. It can be measured relative to the amount at time 0 or relative to the amount at the maximum. An absolute amount can be determined by comparison with a standard curve. A normalized amount can be determined by a ratio with the total amount of MASP in a sample. Those of skill in the art can readily determine suitable controls for a particular assay or suitable means to measure rate, relative amount, or absolute amount.

As used herein, the $IC_{50}$ refers to an amount, concentration or dosage of a particular test compound that achieves a 50% inhibition of a maximal response, such as binding of FGF to tissue receptors, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, pharmaceutically acceptable derivatives of a compound include salts, esters, acids, bases, solvates, hydrates or prodrugs thereof that may be readily prepared by those of skill in this art using known methods for such derivatization and that produce compounds that may be administered to animals or humans without substantial toxic effects and that either are pharmaceutically active or are prodrugs. For example, acidic groups can be esterified or neutralized.

As used herein, treatment means any manner in which the symptoms of a condition, disorder or disease are ameliorated or otherwise beneficially altered. Treatment also encompasses any pharmaceutical use of the compositions herein, such as use as contraceptive agents.

As used herein, amelioration of the symptoms of a particular disorder by administration of a particular pharmaceutical composition refers to any lessening, whether permanent or temporary, lasting or transient that can be attributed to or associated with administration of the composition.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures.

As used herein, the residues of naturally occurring α-amino acids are the residues of those 20 α-amino acids found in nature which are incorporated into protein by the specific recognition of the charged tRNA molecule with its cognate mRNA codon in humans.

As used herein, non-naturally occurring amino acids refer to amino acids that are not genetically encoded. Among those preferred are the non-natural amino acids set forth below with their abbreviations.

As used herein, a conservative amino acid substitution includes any substitution known to one of skill in the art to not substantially alter properties of the resulting peptide. Such substitutions are well known to those of skill in the art or can be determined empirically by making the substitution and testing the ability of the resulting peptide to serve as a substrate.

It is understood that each of the substrates disclosed herein may be modified by making conservative amino acid substitutions and the resulting modified subunits are contemplated herein. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Bejacmin/Cummings Pub. co., p.224). Such substitutions are preferably, although not exclusively, made in accordance with those set forth in TABLE 1 as follows:

TABLE 1

| Original residue | Conservative substitution |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions are also permissible and may be determined empirically or in accord with known conservative substitutions. Any such modification of the polypeptide may be effected by any means known to those of skill in this art. Mutation may be effected by any method known to those of skill in the art, including site-specific or site-directed mutagenesis of DNA encoding the protein and the use of DNA amplification methods using primers to introduce and amplify alterations in the DNA template.

As used herein, a peptidomimetic is a compound that mimics the conformation and certain stereochemical features of the biologically active form of a particular peptide. Peptidomimetics of the substrates exemplified herein are contemplated. In general, peptidomimetics are designed to mimic certain desirable properties of a compound, but not the undesirable properties, such as flexibility, that lead to a loss of a biologically active conformation and bond breakdown. Peptidomimetics may be prepared from biologically active compounds by replacing certain groups or bonds that contribute to the undesirable properties with bioisosteres. Bioisosteres are known to those of skill in the art. For example the methylene bioisostere $CH_2S$ has been used as an amide replacement in enkephalin analogs (see, e.g., Spatola (1983) pp. 267–357 in *Chemistry and Biochemistry of Amino Acids, Peptides, and Proteins,* Weistein, Ed. volume 7, Marcel Dekker, New York). In this instance, any peptidomimetic of the compounds exemplified herein will retain the ability to be cleaved by a MASP.

It is also contemplated herein that compounds disclosed herein may contain chiral centers. Such chiral centers may be of either the (R) or (S) configuration, or may be a mixture thereof. Thus, the compounds disclosed herein may be enantiomerically pure, or be stereoisomeric or diastereomeric mixtures. In the case of amino acid residues, such residues may be of either the L- or D-form. The preferred configuration for naturally occurring amino acid residues is L. It is to be understood that the chiral centers of the compounds provided herein may undergo epimerization in vivo. As such, one of skill in the art will recognize that administration of a compound in its (R) form is equivalent, for compounds that undergo epimerization In vivo, to administration of the compound in its (S) form (and vice versa).

As used herein, hydrophobic amino acids include Ala, Val, Leu, Ile, Pro, Phe, Trp, and Met and any other non-naturally occurring amino acids, including the corresponding D isomers of the hydrophobic amino acids, that have similar hydrophobic properties. It is also understood that certain amino acids may be replaced by substantially equivalent non-naturally occurring variants thereof, such as D-Nva, D-Nle, D-Alle, and others listed below with their abbreviations or known to those of skill in this art.

As used herein a solid support refers to any support to which the compound substrates herein can be linked, either directly or via linker, and by adsorption or absorption, including covalent, ionic or other types of linkages. Solid supports include, but are not limited to materials that are used as affinity matrices or supports for chemical and biological molecule syntheses and analyses, such as: polystyrene, polycarbonate, polypropylene, nylon, glass, dextran, chitin, sand, pumice, teflon, agarose, polysaccharides, dendrimers, buckyballs, polyacrylamide, silicon rubber, and other materials used as supports for solid phase syntheses, affinity separations and purifications, hybridization reactions, immunoassays and other such applications. The support may be particulate or may be in the form of a continuous surface, such as a microtiter dish or well, a glass slide, a silicon chip, a nitrocellulose sheet, nylon mesh, or other such materials. The support may be particularly adapted for linking peptides such as by derivatization or by coating the support with a polymer or other composition, such as derivatized silicon.

As used herein, attached to a solid encompasses any type of attachment including via covalent, ionic and others bonds or frictional forces or any other manner in which the compound is on the surface of the support.

As used herein, alkyl, alkenyl and alkynyl carbon chains, if not specified contain from 1 to 20 carbons, preferably 1 to 16 carbons, and are straight or branched. Alkenyl carbon chains of from 2 to 20 carbons preferably contain 1 to 8 double bonds, and the alkenyl carbon chains of 2 to 16 carbons preferably contain 1 to 5 double bonds. Alkynyl carbon chains of from 2 to 20 carbons preferably contain 1 to 8 triple bonds, and the alkynyl carbon chains of 2 to 16 carbons preferably contain 1 to 5 triple bonds. The alkyl, alkenyl and alkynyl groups may be optionally substituted, with one or more groups, preferably alkyl group substituents that may be the same or different. As used herein, lower alkyl, lower alkenyl, and lower alkynyl refer to carbon chains having less than about 6 carbons.

As used herein, an alkyl group substituent includes halo, haloalkyl, preferably halo lower alkyl, aryl, hydroxy, alkoxy, aryloxy, alkyloxy, alkylthio, arylthio, aralkyloxy, aralkylthio, carboxy alkoxycarbonyl, oxo and cycloalkyl.

As used herein, "aryl" refers to cyclic groups containing from 3 to 19 carbon atoms. Aryl groups include, but are not limited to groups, such as phenyl, substituted phenyl, naphthyl, substituted naphthyl, in which the substituent is lower alkyl, halogen, or lower alkoxy.

As used herein, an "aryl group substituent" includes alkyl, cycloalkyl, cycloalkylalkyl, aryl, heteroaryl optionally substituted with 1 or more, preferably 1 to 3, substituents selected from halo, halo alkyl and alkyl, arylalkyl, heteroarylalkyl, alkenyl containing 1 to 2 double bonds, alkynyl containing 1 to 2 triple bonds, halo, hydroxy, haloalkyl and polyhaloalkyl, preferably halo lower alkyl, especially trifluoromethyl, formyl, alkylcarbonyl, arylcarbonyl that is optionally substituted with 1 or more, preferably 1 to 3, substituents selected from halo, halo alkyl and alkyl, heteroarylcarbonyl, carboxy, alkoxycarbonyl, aryloxycarbonyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, aminoalkyl, alkylaminoalkyl, dialkylaminoalkyl, arylaminoalkyl, amino, alkylamino, dialkylamino, arylamino, alkylarylamino, alkylcarbonylamino, arylcarbonylamino, azido, nitro, mercapto, alkylthio, arylthio, perfluoroalkylthio, thiocyano, isothiocyano, alkylsulfinyl, alkylsufonyl, arylsulfinyl, arylsulfonyl, aminosulfonyl, alkylaminosulfonyl, dialkylaminosulfonyl and arylaminosulfonyl. Exemplary aryl groups include optionally substituted phenyl and optionally substituted pyrenyl.

As used herein, "cycloalkyl" refers to a saturated mono- or multi-cyclic ring system, preferably of 3 to 19 carbon atoms, more preferably 3 to 6 carbon atoms; cycloalkenyl and cycloalkynyl refer to mono- or multicyclic ring systems that respectively include at least one double bond and at least one triple bond. Cycloalkenyl and cycloalkynyl groups may preferably contain 3 to 19 carbon atoms, with cycloalkenyl groups more preferably containing 4 to 7 carbon atoms and cycloalkynyl groups more preferably containing 8 to 10 carbon atoms. The ring systems of the cycloalkyl, cycloalkenyl and cycloalkynyl groups may be composed of one ring or two or more rings which may be joined together in a fused, bridged or spiro-connected fashion, and may be optionally substituted with one or more alkyl group substituents.

As used herein, "heteroaryl" refers to a monocyclic or multicyclic ring system, preferably of about 3 to about 19 members where one or more, more preferably 1 to 3 of the atoms in the ring system is a heteroatom, that is, an element other than carbon, for example, nitrogen, oxygen and sulfur atoms. The heteroaryl may be optionally substituted with one or more, preferably 1 to 3, aryl group substituents. Exemplary heteroaryl groups include, for example, furyl, thienyl, pyridyl, pyrrolyl, N-methylpyrrolyl, quinolinyl and isoquinolinyl, with pyridyl and quinolinyl being preferred.

As used herein, a "heteroarylium" group is a heteroaryl group that is positively charged on one or more of the heteroatoms.

As used herein, "heterocyclic" refers to a monocyclic or multicyclic ring system, preferably of 3 to 19 members, more preferably 4 to 7 members, even more preferably 5 to 6 members, where one or more, preferably 1 to 3 of the atoms in the ring system is a heteroatom, that is, an element other than carbon, for example, nitrogen, oxygen and sulfur atoms. The heterocycle may be optionally substituted with one or more, preferably 1 to 3 aryl group substituents. Preferred substituents of the heterocyclic group include hydroxy, alkoxy containing 1 to 4 carbon atoms, halo lower alkyl, including trihalomethyl, such as trifluoromethyl, and halogen. As used herein, the term heterocycle may include reference to heteroaryl. Exemplary heterocycles include, for example, pyrrolidinyl, piperidinyl, alkylpiperidinyl, morpholinyl, oxadiazolyl or triazolyl.

As used herein, the nomenclature alkyl, alkoxy, carbonyl, etc. are used as is generally understood by those of skill in this art. For example, as used herein alkyl refers to saturated carbon chains that contain one or more carbons; the chains may be straight or branched or include cyclic portions or be cyclic. As used herein, alicyclic refers to aryl groups that are cyclic.

As used herein, "halogen" or "halide" refers to F, Cl, Br or I.

As used herein, pseudohalides are compounds that behave substantially similar to halides. Such compounds can be used in the same manner and treated in the same manner as halides ($X^-$, in which X is a halogen, such as Cl or Br). Pseudohalides include, but are not limited to cyanide, cyanate, thiocyanate, selenocyanate, trifluoromethyl and azide.

As used herein, "haloalkyl" refers to a lower alkyl radical in which one or more of the hydrogen atoms are replaced by halogen including, but not limited to, chloromethyl, trifluoromethyl, 1-chloro-2-fluoroethyl and the like.

As used herein, "haloalkoxy" refers to RO— in which R is a haloalkyl group.

As used herein, "sulfinyl" refers to —S(O)—. As used herein, "sulfonyl" refers to —S(O)$_2$—.

As used herein, "aminocarbonyl" refers to —C(O)NH$_2$.

As used herein, "alkylaminocarbonyl" refers to —C(O)NHR in which R is hydrogen or alkyl, preferably lower alkyl. As used herein "dialkylaminocarbonyl" as used herein refers to —C(O)NR'R in which R' and R are independently selected from hydrogen or alkyl, preferably lower alkyl; "carboxamide" refers to groups of formula —NR'COR.

As used herein, "diarylaminocarbonyl" refers to —C(O)NRR' in which R and R' are independently selected from aryl, preferably lower aryl, more preferably phenyl.

As used herein, "arylalkylaminocarbonyl" refers to —C(O)NRR' in which one of R and R' is aryl, preferably lower aryl, more preferably phenyl, and the other of R and R' is alkyl, preferably lower alkyl.

As used herein, "arylaminocarbonyl" refers to —C(O)NHR in which R is aryl, preferably lower aryl, more preferably phenyl.

As used herein, "alkoxycarbonyl" refers to —C(O)OR in which R is alkyl, preferably lower alkyl.

As used herein, "aryloxycarbonyl" refers to —C(O)OR in which R is aryl, preferably lower aryl, more preferably phenyl.

As used herein, "alkoxy" and "alkylthio" refer to RO— and RS—, in which R is alkyl, preferably lower alkyl.

As used herein, "aryloxy" and "arylthio" refer to RO— and RS—, in which R is aryl, preferably lower aryl, more preferably phenyl.

As used herein, "alkylene" refers to a straight, branched or cyclic, preferably straight or branched, bivalent aliphatic hydrocarbon group, preferably having from 1 to about 20 carbon atoms, more preferably 1 to 12 carbons, even more preferably lower alkylene. The alkylene group is optionally substituted with one or more "alkyl group substituents."

There may be optionally inserted along the alkylene group one or more oxygen, sulphur or substituted or unsubstituted nitrogen atoms, where the nitrogen substituent is alkyl as previously described. Exemplary alkylene groups include methylene (—CH₂—), ethylene (—CH₂CH₂—), propylene (—(CH₂)₃—), cyclohexylene (—C₆H₁₀—), methylenedioxy (—O—CH₂—O—) and ethylenedioxy (—O—(CH₂)₂—O—). The term "lower alkylene" refers to alkylene groups having 1 to 6 carbons. Preferred alkylene groups are lower alkylene, with alkylene of 1 to 3 carbon atoms being particularly preferred.

As used herein, "alkenylene" refers to a straight, branched or cyclic, preferably straight or branched, bivalent aliphatic hydrocarbon group, preferably having from 2 to about 20 carbon atoms and at least one double bond, more preferably 2 to 12 carbons, even more preferably lower alkenylene. The alkenylene group is optionally substituted with one or more "alkyl group substituents." There may be optionally inserted along the alkenylene group one or more oxygen, sulphur or substituted or unsubstituted nitrogen atoms, where the nitrogen substituent is alkyl as previously described. Exemplary alkenylene groups include —CH═CH—CH═CH— and —CH═CH—CH₂—. The term "lower alkenylene" refers to alkenylene groups having 2 to 6 carbons. Preferred alkenylene groups are lower alkenylene, with alkenylene of 3 to 4 carbon atoms being particularly preferred.

As used herein, "alkynylene" refers to a straight, branched or cyclic, preferably straight or branched, bivalent aliphatic hydrocarbon group, preferably having from 2 to about 20 carbon atoms and at least one triple bond, more preferably 2 to 12 carbons, even more preferably lower alkynylene. The alkynylene group is optionally substituted with one or more "alkyl group substituents." There may be optionally inserted along the alkynylene group one or more oxygen, sulphur or substituted or unsubstituted nitrogen atoms, where the nitrogen substituent is alkyl as previously described. Exemplary alkynylene groups include —C≡C—C≡C—, —C≡C— and —C≡C—CH₂—. The term "lower alkynylene" refers to alkynylene groups having 2 to 6 carbons. Preferred alkynylene groups are lower alkynylene, with alkynylene of 3 to 4 carbon atoms being particularly preferred.

As used herein, "arylene" refers to a monocyclic or polycyclic, preferably monocyclic, bivalent aromatic group, preferably having from 3 to about 20 carbon atoms and at least one aromatic ring, more preferably 3 to 12 carbons, even more preferably lower arylene. The arylene group is optionally substituted with one or more "alkyl group substituents." There may be optionally inserted around the arylene group one or more oxygen, sulphur or substituted or unsubstituted nitrogen atoms, where the nitrogen substituent is alkyl as previously described. Exemplary arylene groups include 1,2-, 1,3- and 1,4-phenylene. The term "lower arylene" refers to arylene groups having 5 or 6 carbons. Preferred arylene groups are lower arylene.

As used herein, "heteroarylene" refers to a bivalent monocyclic or multicyclic ring system, preferably of about 3 to about 15 members where one or more, more preferably 1 to 3 of the atoms in the ring system is a heteroatom, that is, an element other than carbon, for example, nitrogen, oxygen and sulfur atoms. The heteroarylene group may be optionally substituted with one or more, preferably 1 to 3, aryl group substituents. Exemplary heteroarylene groups include, for example, 1,4-imidazolylene.

As used herein, "alkylidene" refers to a bivalent group, such as ═CR'R", which is attached to one atom of another group, forming a double bond. Exemplary alkylidene groups are methylidene (═CH₂) and ethylidene (═CHCH₃). As used herein, "arylalkylidene" refers to an alkylidene group in which either R' or R" is and aryl group. As used herein, "diarylalkylidene" refers to an alkylidene group in which R' and R" are both aryl groups. "Diheteroarylalkylidene" refers to an alkylidene group in which R' and R" are both heteroaryl groups.

As used herein, "arylidene" refers to an unsaturated cyclic bivalent group where both points of attachment are on the same atom of the ring. Exemplary arylidene groups include, but are not limited to, quinone methide moieties that have the formula:

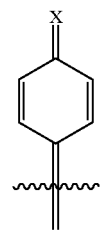

where X is O, S or NR'. "Heteroarylidene" groups are arylidene groups where one or two, preferably two, of the atoms in the ring are heteroatoms, such as, but not limited to, O, S and N.

As used herein, "amido" refers to a bivalent group, either —C(O)NH— or —HNC(O)—. "Thioamido" refers to a bivalent group, either —C(S)CH— or —HNC(S)—. "Oxyamido" refers to a bivalent group, either —OC(O)NH— or —HNC(O)O—. "Thiaamido" refers to a bivalent group, either —SC(O)NH— or —HNC(O)S—. "Dithiaamido" refers to a bivalent group, either —SC(S)NH— or —HNC(S)S—. "Ureido" refers to the bivalent group —HNCONH—. "Thioureido" refers to the bivalent group —HNCSNH—.

As used herein, the term "amino acid" refers to α-amino acids which are racemic, or of either the D- or L-configuration.

As used herein, when any particular group, such as phenyl or pyridyl, is specified, this means that the group is unsubstituted or is substituted. Preferred substituents where not specified are halo, halo lower alkyl, and lower alkyl.

As used herein, the designations "P1, P2, P3 . . . ", etc., refer to residues in the peptide chain, beginning at the C-terminal position. Thus, the P1 residue is the C-terminal residue in the compounds disclosed herein. The P2 residue is the next residue in the peptide chain, followed by the P3 residue, etc.

As used herein, a receptor refers to a molecule that has an affinity for a given ligand. Receptors may be naturally-occurring or synthetic molecules. Receptors may also be referred to in the art as anti-ligands. As used herein, both terms, receptor and anti-ligand are interchangeable. Receptors can be used in their unaltered state or as aggregates with other species. Receptors may be attached, covalently or noncovalently, or in physical contact with, to a binding member, either directly or indirectly via a specific binding substance or linker. Examples of receptors, include, but are not limited to: antibodies, cell membrane receptors surface receptors and internalizing receptors, monoclonal antibodies and antisera reactive with specific antigenic determinants [such as on viruses, cells, or other materials], drugs, polynucleotides, nucleic acids, peptides, cofactors, lectins, sugars, polysaccharides, cells, cellular membranes, and organelles.

Examples of receptors and applications using such receptors, include but are not restricted to:

a) enzymes: specific transport proteins or enzymes essential to survival of microorganisms, which could serve as targets for antibiotic [ligand] selection;

b) antibodies: identification of a ligand-binding site on the antibody molecule that combines with the epitope of an antigen of interest may be investigated; determination of a sequence that mimics an antigenic epitope may lead to the development of vaccines of which the immunogen is based on one or more of such sequences or lead to the development of related diagnostic agents or compounds useful in therapeutic treatments such as for auto-immune diseases c) nucleic acids: identification of ligand, such as protein or RNA, binding sites;

d) catalytic polypeptides: polymers, preferably polypeptides, that are capable of promoting a chemical reaction involving the conversion of one or more reactants to one or more products; such polypeptides generally include a binding site specific for at least one reactant or reaction intermediate and an active functionality proximate to the binding site, in which the functionality is capable of chemically modifying the bound reactant [see, e.g., U.S. Pat. No. 5,215,899];

e) hormone receptors: determination of the ligands that bind with high affinity to a receptor is useful in the development of hormone replacement therapies; for example, identification of ligands that bind to such receptors may lead to the development of drugs to control blood pressure; and f) opiate receptors: determination of ligands that bind to the opiate receptors in the brain is useful in the development of less-addictive replacements for morphine and related drugs.

As used herein, antibody includes antibody fragments, such as Fab fragments, which are composed of a light chain and the variable region of a heavy chain.

As used herein, complementary refers to the topological compatibility or matching together of interacting surfaces of a ligand molecule and its receptor. Thus, the receptor and its ligand can be described as complementary, and furthermore, the contact surface characteristics are complementary to each other.

As used herein, a ligand-receptor pair or complex formed when two macromolecules have combined through molecular recognition to form a complex.

As used herein, an epitope refers to a portion of an antigen molecule that is delineated by the area of interaction with the subclass of receptors known as antibodies. As used herein, a ligand is a molecule that is specifically recognized by a particular receptor. Examples of ligands, include, but are not limited to, agonists and antagonists for cell membrane receptors, toxins and venoms, viral epitopes, hormones [e.g., steroids], hormone receptors, opiates, peptides, enzymes, enzyme substrates, cofactors, drugs, lectins, sugars, oligonucleotides, nucleic acids, oligosaccharides, proteins, and monoclonal antibodies.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942). Other abbreviations used herein are (abbreviation, definition): C3a and C4a, fragments called anaphylatoxins that are generated from complement components C3 and C4, respectively; CMV, cytomegalo-virus; γGT, gamma-glutamyl transferase; CsA, cyclosporine A, FK506 (a well known macrolide antibiotic isolated from the fungus *Streptomyces tsukubaensis* by the Fujisawa Pharmaceutical Company of Japan, see, e.g., U.S. Pat. Nos. 5,807,876, 5,100,899, and 5,164,495); SGPT, aspartate aminotransferase; SGOT, alanine aminotransferase; Nle, norleucine; pNA, para-nitroanilino; Ac, acetyl; MCA, 4-methylcoumaryl- 7-amino; CR1, complement C3b receptor; Futhan, 6-amidino-2-naphthyl-p-guanidinobenzoate dimethanesulfonate; MASP-1, MBL (mannan-binding lectin)-associated serine protease-1; MASP-2, MBL (mannan-binding lectin)-associated serine protease-2; and EDTA, ethylened laminetetraacetic acid.

Each naturally occurring L-amino acid is identified by the standard three letter code or the standard three letter code with or without the prefix "L-"; the prefix "D-" indicates that the stereoisomeric form of the amino acid is D. Other abbreviations for amino acids and non-natural amino acids contemplated herein include: Aib for 2-amino-2-methylpropionic acid, β-Ala for β-alanine, α-Aba for L-α-aminobutanoic acid; D-α-Aba for D-α-aminobutanoic acid; $Ac_3c$ for 1-aminocyclopropanecarboxylic acid; $Ac_4c$ for 1-aminocyclobutanecarboxylic acid; $Ac_5c$ for 1-aminocyclopentanecarboxylic acid; $Ac_6c$ for 1-aminocyclohexanecarboxylic acid; $Ac_7c$ for 1-aminocycloheptanecarboxylic acid; D-Asp(ONa) for sodium D-aspartate; D-Bta for D-3-(3-benzo[b]thienyl) alanine; $C_3$al for L-3-cyclopropylalanine; $C_4$al for L-3-cyclobutylalanine; $C_5$al for L-3-cyclopentylalanine; $C_6$al for L-3-cyclohexylalanine; D-Chg for D-2-cyclohexylglycine; CmGly for N-(carboxymethyl)glycine; D-Cpg for D-2-cyclopentylglycine; CpGly for N-cyclopentylglycine; Cys $(O_3Na)$ for sodium L-cysteate; D-Cys$(O_3H)$ for D-cysteic acid; D-Cys$(O_3Na)$ for sodium D-cysteate; D-Cys$(O_3Bu_4N)$ for tetrabutylammonium D-cysteate; D-Dpg for D-2-(1,4-cyclohexadienyl)- glycine; D-Etg for (2S)-2-ethyl-2-(2-thienyl)glycine; D-Fug for D-2-(2-furyl)glycine; Hyp for 4-hydroxy-L-proline; leGly for N-[2-(4-imida-zolyl)ethyl] glycine; alle for L-L-alloisoleucine; D-alle for D-alloisoleucine; D-ltg for D-2-(isothiazolyl)glycine; D-tertLeu for D-2-amino-3,3-dimethylbutanoic acid; Lys (CHO) for $N^6$-formyl-L-lysine; MeAla for N-methyl-L-alanine; MeLeu for N-methyl-L-leucine; MeMet for N-methyl-L-methionine; Met(O) for L-methionine sulfoxide; Met($O_2$) for L-methionine sulfone; D-Nal for D-3-(1-naphthyl) alanine; Nle for L-norleucine; D-Nle for D-nor-leucine; Nva for L-norvaline; D-Nva for D-norvaline; Orn for L-ornithine; Orn(CHO) for $N^5$-formyl-L-ornithine; D-Pen for D-penicillamine; D-Phg for D-phenylglycine; Pip for L-pipecolinic acid; $^iPrGly$ for N-isopropylglycine; Sar for sarcosine; Tha for L-3-(2-thienyl)alanine; D-Tha for D-3(2-thienyl)-alanine; D-Thg for D-2-(2-thienyl)glycine; Thz for L-thiazolidine-4-carboxylic acid; D-Trp(CHO) for $N^{in}$-formyl-D-tryptophan; D-trp(O) for D-3-(2,3-dihydro-2-oxoindol-3-yl)alanine; D-trp$((CH_2)_mCOR^1)$ for D-tryptophan substituted by a —$(CH_2)_mCOR^1$ group at the 1-position of the indole ring; Tza for L-3-(2-thiazolyl) alanine; D-Tza for D-3-(2-thiazolyl)alanine; D-Tzg for D-2-(thiazolyl)glycine; Bzl for benzyl; DMF for N,N-dimethylformamide; Boc for tert-butoxycarbonyl; TFA for trifluoroacetic acid; HF for hydrogen fluoride; HFIP for hexafluoroisopropanol; HPLC for high performance liquid chromatography; FAB-MS for fast atom bombardment mass spectrometry; DCM is dichloromethane, Bom is benzyloxymethyl; Pd/C is palladium catalyst on activated charcoal; BOP is benzotriazol-1-yloxy-tris(dimethylamino) phosphonium hexafluorophosphate; DIC is diisopropylcarbodiimide; DCC is N,N'-dicyclohexylcarbodiimide; and (For) is formyl.

B. Assay

Background

Key among these are the results in the copending applications (U.S. application Ser. No. 09/173,579 and the continuation-in-part, filed Feb. 5, 1999) were those that demonstrated that EDTA is the activator of the MASP activity in EDTA plasma. When the benzamidine, a coagulation inhibitor is added, there is no C4a generated in whole blood, but upon addition of EDTA, high levels of C4a are generated. Since benzamidine blocks the alterative and classical and coagulation pathways but does not inhibit MASP activity, the high levels of C4a generated are attributable to activated MASP, particularly MASP-2, previously present in the MBL complex, but released upon contact with EDTA. Thus, the increase must attributed to MASP activity generated upon exposure of the complex to EDTA or other chelator. Futhan inhibits MASP. Therefore, even in EDTA, no MASP activity is observed.

The proteinase responsible for the in vitro activation of C4 is the MASP-2 enzyme of the lectin pathway (Thiel et al. (1997) Nature 386:506–510). The MASP-2 enzyme of the lectin pathway is primarily responsible for in vitro C-activation (See Table II, below). Thus, assessing MASP activity provides a status of abnormality, to assess exposure to viruses and parasites, tissue injury or anything that leads to exposure of neutral sugars.

Assays of MASP activity can be used for evaluating blood units drawn in blood banks to identify virally (or parasitically) infected blood samples. They also can be used to monitor patient conditions, such as viral, parasitic infections and other diseases, and for longitudinal monitoring to detect changes in status, such as in organ transplant patients.

The assays of MASP activity can also be used to monitor for effectiveness of therapeutics, such as antiviral treatments (for treatment of hepatitis B, C, CMV, HIV infections), antiparasitics, and tissue injury treatments.

Summary of assays provided herein

The complement system includes three distinct pathways composed of more than 25 proteins that activate, regulate and/or potentiate these cascade systems. The best known pathways are defined as the classical and the alternative Pathways. These pathways function to recognize and help destroy pathogens, are involved in recognition of host tissue injury and repair, and generally assist or complement the host's humoral immune response.

The third pathway of complement activation is called the lectin pathway. The components of this pathway include the mannan-binding lectin (MBL) and two serine proteinases called mannan-binding lectin associated serine proteinase 1 (MASP-1) and 2 (MASP-2). MBL binds to neutral sugars, such as those on virus particles, parastites and injured tissue, and the MASP enzymes are activated.

Activated MASP-1 enzyme has been shown to activate the MASP-2 enzyme, which in turn cleaves the fourth (C4) component of complement. There is evidence that MASP-1 cleaves C3.

One of the manifestations of lectin pathway activation is the generation of the fragment C4a in the blood/plasma. Generation of the fragment C4a can be used to monitor the presence of the activated Lectin enzyme MASP-2 in plasma. The classical and alternative pathways are inhibited when calcium is removed. EDTA plasma samples collected for complement measurements are unstable; C3 and C4 can continue to be converted in vitro after the sample is collected. This activation of the complement components occurs even when samples stored at 4° C.

The lectin enzyme MASP-2 is a serine proteinase having trypsin-like (i.e. Arg-X) specificity, a direct functional assay has been designed using selected peptide fragments that this enzyme cleaves. MASP-2 is stable in plasma samples and the rate of substrate conversion is proportional to the level of this enzyme, thereby providing a rapid and simple assay system to quantitate the activity of the enzyme in biological fluids.

As noted above, the assay of interest herein, include the following:

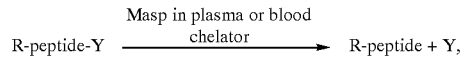

where the peptide is a any peptide cleavable by MASP or is a peptide or peptide analog provided herein; the Y is a group that includes a tag that is any detectable label, such that cleavage can be assessed. Generally these substrates include any trypsin-like peptide selected for the ability to be cleaved by MASP, but preferably include the C-terminal 3 to 5 amino acids of a C3a, C4a or C5a protein, preferably a C4a.

In practicing the assays, the peptide substrate is added to a sample of blood or plasma that contains an inhibitor of complement pathway convertases (other than a MASP enzyme), such as a calcium chelator, including EDTA, citrate or the equivalent. R is a protecting group, or a capping group or any suitable C-terminal group, such as Cbz, Boc, FMoc, and Ac, or it is additionally or alternatively a tag that will change properties upon cleavage of Y. For example, a combination of a fluorescent moiety, such as 2-methyl-anthranilic acid, whose fluorescence is quenched by the C-terminus or C-terminal moiety, such as pNA can be used. Upon cleavage, fluorescence of the anthranilic acid-labeled peptide can be detected and/or the change in O.D. resulting from cleavage of the pNA can be measured. Other such pairs of tags can be identified.

In the assays herein, the cleavage of a substrate recognized by a MASP enzyme in a sample of blood or plasma in the presence of a calcium chelator or other agent that removes calcium, is measured. The change in a property, such as O.D. or fluorescence of the mixture resulting from cleavage of the substrate is measured.

In certain embodiments, assay of the tag, especially β-naphthylamino, may be performed with the assistance of a color developer, such as azo-diazo dyes, fast garnet-gbc salt (o-aminoazotoluene diazonium salt, available from Simga Chemicals, St. Louis, Mo.), fast blue, fast black and p-dimethylaminocinnamaldehyde. See, U.S. Pat. Nos. 5,116,735 and 5,223,403, the disclosures of which are incorporated herein by reference. Addition of the color developer following incubation of the compound with the test sample results in a more intense color change and/or better color differentiation between a positive and a negative result, simplifying the assay.

It has been found herein, that certain substrates are species-specific in that they are more preferred substrates for assessing MASP activation from a particular species. Accordingly, species-specific assays are provided.

C. Compounds for use in Complement Activation Assays

The assays employ compounds of formula:

R-peptide-Y, where one or both of R and Y are detectable upon cleavage of Y. Each of Y and R can include a tag that is detectable upon cleavage of the substrate by MASP. The compounds, which include compounds heretofore known for other uses and also compounds provided herein in intended for use as substrates in the assays that measure activation of MASP. The compounds are peptides and peptide derivatives that are substrates for MASP-1 or MASP-2.

The peptide portion is any peptide that includes at least two, preferably three to five or six residues from the C-terminal portion of any convertase substrate, particularly C3a, C4a or C5a, preferably C4a, up to the full-length of such substrate and including additional residues, if desired. Shorter peptides are preferred.

The compounds possess at the C-terminus, and/or at the N-terminus, a tag that can be quantitatively assayed following exposure to a test sample to determine the amount of activated MASP in the sample. The compounds are selected so that upon cleavage of the substrate by MASP-1 or MASP-2, the tag is detectable. If it is present at the C-terminus it is released. Subsequent quantitative analysis of the released tag in the sample is therefore indicative of the amount of activated MASP enzyme in the sample.

The compounds are peptide and peptide derivatives, and are C-terminal esters, amides or thioesters that contain the compounds contain at least two, preferably four to five, amino acid residues or analogs thereof. The compounds include Y, which contains a tag at the C-terminus and preferably are capped and/or include a tag at the N-terminus. Among the most preferred compounds for use a substrates are those of the following formula:

Blocking group-P5-P4-P3-P2-P1-tag, where:

P1 is Arg or Lys or, preferably, Arg;

P2 is Ala, Gly, Gln, Leu, Asn, Thr, Ala, or Nle preferably Gln, Asn, Gly, Thr, Ala, or Nle;

P3 is Gly, Gln, Leu is preferably Leu and is optional;

P4 is preferably Gly, and can be optional;

P5, which is also optional, can almost any group and can be replaced by a bulky blocking group, such as Cbz;

P1-P5 are preferably the L-isomer;

Ac (acetyl) is among the preferred blocking groups, but can be replaced by an N-terminal blocking group, particularly any that does not markedly change the cleavage rate of the enzyme; and the tag is any detectable label, including colorimetric, bioluminescent, fluorescent, radiolabels and enzyme labels that can be monitored upon cleavage. Among the preferred tags are colorimetric or chromogenic tags, such as pNA (para-ntiranilide) and fluorescent tags that for which the absorption or emission spectra change upon cleavage. Other tags that, upon cleavage, can react with other substrates, are also contemplated herein.

Compounds are provided for use in methods for determining the level of complement activation in a test sample. In particular, compounds are provided for use in methods that measure the activation of mannan-binding protein-associated serine protease (MASP). The compounds are peptides and peptide derivatives that are substrates for MASP-1 or MASP-2. The compounds possess at the C-terminus a tag that can be quantitatively assayed following exposure to a test sample to determine the amount of activated MASP in the sample. The compounds are preferably substrates specific for MASP-1 or MASP-2, where the action of MASP-1 or MASP-2 on the compound releases the tag. Subsequent quantitative analysis of the released tag in the sample is therefore indicative of the amount of activated MASP in the sample.

Among the preferred compounds are those in which the peptide includes or has SEQ ID Nos. 15–19.

3. Compounds

Also provided herein are compounds for use in the assays and in the kits for the assays. The compounds are peptide and peptide derivatives, and are C-terminal esters, amides or thioesters. The compounds contain a tag at the C-terminus and preferably are capped at the N-terminus, as described above. It is to be understood that the compounds contain from about 2 up to about 76, preferably less than 70, more preferably less than 60, particularly less than 50, more preferably less than 25, amino acid residues or analogs thereof, containing the sequence of amino acids in a C3a, C4a or C5a peptide. Particularly preferred embodiments are compounds that contain 5–10, preferably 5–7, most preferably 5, amino acid residues of a C3a, C4a or C5a peptide or analogs thereof.

It is also to be understood that the compounds for use in the methods described herein may be concatamers of the compounds described herein. In all embodiments described herein, compounds of formula (I), (II) and (III) that are suitable substrates for MASP-1 or MASP-2 may be determined empirically by testing them as substrates is the assays.

In preferred embodiments, the compounds for use in methods that determine the level of complement activation have formula (I):

$$R^{30}\underset{R^{25}}{\overset{R^{5}}{N}}\underset{O}{\overset{R^{24}}{\underset{}{N}}}X\underset{R^{3}}{\overset{R^{23}}{N}}\underset{}{\overset{O}{\underset{}{}}}\underset{R^{22}}{\overset{R^{2}}{N}}\underset{O}{\overset{R^{21}}{\underset{}{N}}}\underset{R^{1}}{\overset{O}{Y}} \quad (I)$$

or analogs thereof, where $R^1$ is $R^{60}$-A, where A is $NH_t(R^{40})_{3-t}$, heterocyclyl, heteroaryl, guanidinyl, amidino or imino, and is capable of forming a cationic salt, preferably at about physiological pH, or is $N^+(R^{40})_4$;

$R^{60}$ is alkylene, alkenylene, alkynylene, cycloalkylene, heterocyclylene, aralkylene, heteroaralkylene, arylene or heteroarylene;

$R^{40}$ is alkyl, alkenyl, alkynyl, aryl or heteroaryl;

t is 0–3;

$R^{21}$ is H or alkyl;

X is a group that allows for flexibility in the chain, preferably alkylene, alkenylene or $CH(R^4)C(O)$;

$R^2$, $R^3$, $R^4$, $R^5$, $R^{22}$, $R^{23}$, $R^{24}$, $R^{25}$ and $R^{30}$ are each independently selected as in (i) or (ii) as follows:

(i) $R^2$, $R^3$, $R^4$ and $R^5$ are each independently selected from a side chain of a naturally occurring a-amino acid, H, alkyl, preferably lower ($C_{1-6}$) alkyl, alkenyl, preferably $C_{2-10}$ alkenyl, alkynyl, preferably $C_{2-6}$ alkynyl, aryl, aralkyl, aralkenyl, aralkynyl, heteroaryl, heteroaralkyl, heteroaralkenyl, $Z^1$-substituted aryl, aralkyl, aralkenyl or aralkynyl, and $Z^2$-substituted heteroaryl, heteroaralkyl or heteroaralkenyl;

$Z^1$ is selected from halogen, lower alkyl, lower alkoxy, OH, haloalkyl, preferably $CF_3$, $NO_2$, nitrile, alkylthio, phenyl and —NNR'R";

each of R' and R" is independently H, alkyl, preferably lower alkyl, OH or halo lower alkyl, particularly $CF_3$;

$Z^2$ is lower alkyl, preferably $C_{1-4}$ alkyl, or halo lower alkyl, preferably $C_{1-4}$ haloalkyl, more preferably $CF_3$;

$R^{22}$, $R^{23}$ and $R^{24}$ are each independently H or alkyl; and $R^{30}$ and $R^{25}$ are each independently selected as in (a), (b) or (c) as follows:

(a) $R^{30}$ is a peptide residue containing any number of residues such that the resulting compound is cleaved by MASP, and preferably containing from 1 to 71, preferably 1–65, more preferably 1–55, particularly 1–45, more preferably 1–20 or 1–5, most preferably 1–2, amino acid residues, wherein the resulting compound contains a site cleavable by MASP, and particularly contains a C-terminal portion of at least 2, preferably 3–10, more preferably 4–6 residues of SEQ ID NOS. 1 through 14, preferably SEQ ID NOS. 1 through 9, more preferably SEQ ID NOS. 6 through 9, most preferably SEQ ID NO. 6, and $R^{25}$ is H or alkyl; or (b) $R^{30}$ and $R^{25}$ are each independently H, $C(O)R^{10}$, alkyl, alkenyl, alkynyl, aryl, heteroaryl, aralkyl, heteroaralkyl, $Si(R^{10})_3$, $S(O)_m R^{10}$ where m is 0–2 or $P(O)_n(R^{10})_p$ where n is 0–3; p is 1–2; $R^{10}$ is alkyl, aryl, heteroaryl, aralkyl, heteroaralkyl, alkoxy, aryloxy, heteroaryloxy, aralkoxy, heteroaralkoxy or $NR^{11}R^{12}$; and $R^{11}$ and $R^{12}$ are each independently selected from among H, alkyl, aryl, heteroaryl, aralkyl and heteroaralkyl; or (c) $R^{30}$ and $R^{25}$, together with the nitrogen atom to which they are attached, form a heterocyclyl, heteroaryl, cyclic amide or cyclic imide group; or (ii) $R^2$ and $R^{22}$, and/or $R^3$ and $R^{23}$, and/or $R^4$ and $R^{24}$, and/or $R^5$ and $R^{25}$ together form alkylene, preferably ethylene, propylene, butylene or pentylene, more preferably propylene; and the remainder of $R^2$, $R^3$, $R^4$, $R^5$, $R^{22}$, $R^{23}$, $R^{24}$, $R^{25}$ and $R^{30}$ are selected as in (i);

Y contains or is detectable tag group that is detectable labeled from a member selected from a radiolabel, a photochemical label, a colorimetric label, a chromogenic label, a fluorescent a label, a fluorogenic label, a phosphorescent label, an electrochemical label, chemiluminescent or a bioluminescent label or a reporter-labeled ligand or receptor therefor, including a reporter-labeled antibody or antigen; and $R^1$, $R^2$, $R^3$, $R^4$, $R^5$, $R^{25}$, $R^{30}$, X and Y are unsubstituted or are substituted with one or more substituents selection from Q, which, as defined herein, is halogen, hydroxy, nitrile, nitro, formyl, mercapto, carboxy, hydroxysulfonyl, hydroxyphosphoryl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl, or any two Q groups substituting adjacent atoms on an aryl or heteroaryl group may form 1,3-butadienylene, 1-aza-1,3-butadienylene or 2-aza-1,3-butadienylene.

The compounds of formula (I) contain a P1 residue that possesses a side chain that is cationic, preferably at about physiological pH. Preferred side chains possess a basic nitrogen atom. Thus, suitable side chains contain, for example, $NH_t(R^{40})_{3-t}$, heterocyclyl, heteroaryl, guanidinyl or imino groups, where $R^{40}$ is alkyl, alkenyl, alkynyl, aryl or heteroaryl and t is 0–3. Alternatively, the side chains may possess quaternary ammonium ions of structure $N^+(R^{40})_4$.

Preferred P1 side chains include those that contain $NH_t(R^{40})_{3-t}$, heteroaryl or guanidinyl groups, where $R^{40}$ is alkyl, alkenyl, alkynyl, aryl or heteroaryl and t is 0–3, more preferably $NH_t(R^{40})_{3-t}$ or guanidinyl groups. $R^{40}$ is preferably alkyl, alkenyl or alkynyl.

In certain preferred embodiments, the P1 residue is that of a naturally occurring amino acid. Thus, more preferred P1 residues are lysine, arginine and histidine, lysine and arginine are particularly preferred, arginine is most preferred.

In certain embodiments herein, the compounds of formula (I) are selected such that the P5 residue is a non-aromatic hydrophobic group. Thus, in these embodiments, $R^5$, $R^{25}$ and $R^{30}$ are selected from (i), (ii) or (iii) as follows:

(i) $R^5$ is the side chain of isoleucine, methionine, leucine, valine, alanine, glycine, serine or threonine; and $R^{25}$ and $R^{30}$ are selected as in (a), (b) or (c) as follows:

(a) $R^{30}$ is a peptide residue containing from 1 to about 100, preferably about 72 amino acid residues, such that the resulting compound contains the C-terminal portion, at least two residues, up to the full-length of SEQ ID NOS. 1 through 14, preferably SEQ ID NOS. 1 through 9, more preferably SEQ ID NOS. 6 through 9, most preferably SEQ ID NO. 6, and $R^{25}$ is H or alkyl; or (b) $R^{30}$ and $R^{25}$ are each independently H, $C(O)R^{10}$, alkyl, alkenyl, alkynyl, aryl, heteroaryl, aralkyl, heteroaralkyl, $Si(R^{10})_3$, $S(O)_m R^{10}$ where m is 0–2 or $P(O)_n(R^{10})_p$ where n is 0–3; p is 1–2; $R^{10}$ is alkyl, aryl, heteroaryl, aralkyl, heteroaralkyl, alkoxy, aryloxy, heteroaryloxy, aralkoxy, heteroaralkoxy or $NR^{11}R^{12}$; and $R^{11}$ and $R^{12}$ are each independently selected from among H, alkyl, aryl, heteroaryl, aralkyl and heteroaralkyl; or (c) $R^{30}$ and $R^{25}$, together with the nitrogen atom to which they are attached, form a heterocyclyl, heteroaryl, cyclic amide or cyclic imide group; or (ii) $R^5$ and $R^{25}$ together form alkylene, preferably ethylene, propylene, butylene or pentylene, more preferably propylene (i.e., the P5 residue is proline); and $R^{30}$ is selected as in (i)(a) or (i)(b); or (iii) $R^5$ is alkyl, preferably lower ($C_{1-6}$) alkyl, alkenyl, preferably $C_{2-10}$ alkenyl, or alkynyl, preferably $C_{2-6}$ alkynyl; and $R^{25}$ and $R^{30}$ are selected as in (i).

In other embodiments, $R^{30}$ is an acyl group and $R^1$ is the side chain of arginine. In these embodiments, the compounds of formula (I) have formula (III):

(II)

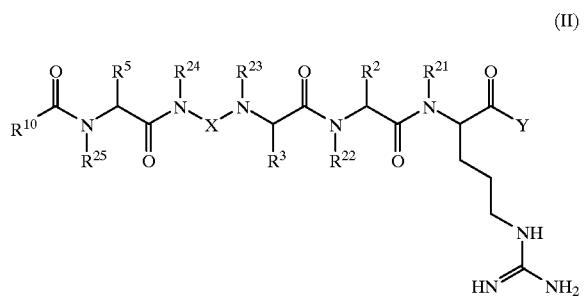

where $R^{21}$ is H or alkyl;

X is a group that allows for flexibility in the chain, preferably alkylene, alkenylene or $CH(R^4)C(O)$;

$R^{10}$ is selected from (i) or (ii) as follows:
(i) alkyl, aryl, heteroaryl, aralkyl, heteroaralkyl, alkoxy, aryloxy, heteroaryloxy, aralkoxy, heteroaralkoxy or $NR^{11}R^{12}$; or
(ii) $R^{10}$ contains 1–5, preferably 1–2, amino acid residues or analogs thereof, with the N-terminus capped with $C(O)R^{70}$;

$R^{70}$ is alkyl, aryl, heteroaryl, aralkyl, heteroaralkyl, alkoxy, aryloxy, heteroaryloxy, aralkoxy, heteroaralkoxy or $NR^{11}R^{12}$;

$R^{11}$ and $R^{12}$ are each independently H, alkyl, aryl, heteroaryl, aralkyl or heteroaralkyl;

$R^2$, $R^3$, $R^4$, $R^5$, $R^{22}$, $R^{23}$, $R^{24}$ and $R^{25}$ are each independently selected as in (i) or (ii) as follows:
(i) $R^2$, $R^3$, $R^4$ and $R^5$ are each independently selected from a side chain of a naturally occurring α-amino acid, H, alkyl, preferably lower ($C_{1-6}$) alkyl, alkenyl, preferably $C_{2-10}$ alkenyl, alkynyl, preferably $C_{2-6}$ alkynyl, aryl, aralkyl, aralkenyl, aralkynyl, heteroaryl, heteroaralkyl, heteroaralkenyl, $Z^1$-substituted aryl, aralkyl, aralkenyl or aralkynyl, and $Z^2$-substituted heteroaryl, heteroaralkyl or heteroaralkenyl;

$Z^1$ is selected from halogen, lower alkyl, lower alkoxy, OH, haloalkyl, preferably $CF_3$, $NO_2$, nitrile, alkylthio, phenyl and —NR'R";

each of R' and R" is independently H, alkyl, preferably lower alkyl, OH or halo lower alkyl, particularly $CF_3$;

$Z^2$ is lower alkyl, preferably $C_{1-4}$ alkyl, or halo lower alkyl, preferably $C_{1-4}$ haloalkyl, more preferably $CF_3$;

$R^{22}$, $R^{23}$, $R^{24}$ and $R^{25}$ are each independently H or alkyl; or (ii) $R^2$ and $R^{22}$, and/or $R^3$ and $R^{23}$, and/or $R^4$ and $R^{24}$, and/or $R^5$ and $R^{25}$ together form alkylene, preferably ethylene, propylene, butylene or pentylene, more preferably propylene; and the remainder of $R^2$, $R^3$, $R^4$, $R^5$, $R^{22}$, $R^{23}$, $R^{24}$ and $R^{25}$ are selected as in (i);

Y is a tag group capable of being detected by assays that detect radiolabelled, photochemical, colorimetric, chromogenic, fluorescent, fluorogenic, phosphorescent, electrochemical, chemiluminescent or bioluminescent tags, as described above; and $R^2$, $R^3$, $R^4$, $R^5$, X and Y are unsubstituted or are substituted with one or more substituents selection from Q, which, as defined herein, is halogen, hydroxy, nitrile, nitro, formyl, mercapto, carboxy, hydroxysulfonyl, hydroxyphosphoryl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl, or any two Q groups substituting adjacent atoms on an aryl or heteroaryl group may form 1,3-butadienylene, 1-aza-1,3-butadienylene or 2-aza-1,3-butadienylene.

In particularly preferred embodiments, $R^{10}$ is selected preferably from $CH(R^6)$—$NH(R^{26})$—$C(O)R^{70}$ or $CH(R^6)$—$NH(R^{26})C(O)$—$CH(R^7)$—$NH(R^{27})$—$C(O)$—$R^{70}$, where $R^6$, $R^7$, $R^{26}$ and $R^{27}$ are each independently selected from (i) or (ii) as follows:
(i) $R^6$ and $R^7$ are each independently selected from a side chain of a naturally occurring α-amino acid, H, alkyl, preferably lower ($C_{1-6}$) alkyl, alkenyl, preferably $C_{2-10}$ alkenyl, alkynyl, preferably $C_{2-6}$ alkynyl, aryl, aralkyl, aralkenyl, aralkynyl, heteroaryl, heteroaralkyl, heteroaralkenyl, $Z^1$-substituted aryl, aralkyl, aralkenyl or aralkynyl, and $Z^2$-substituted heteroaryl, heteroaralkyl or heteroaralkenyl;

$Z^1$ is selected from halogen, lower alkyl, lower alkoxy, OH, haloalkyl, preferably $CF_3$, $NO_2$, nitrile, alkylthio, phenyl and —NR'R";

each of R' and R" is independently H, alkyl, preferably lower alkyl, OH or halo lower alkyl, particularly $CF_3$;

$Z^2$ is lower alkyl, preferably $C_{1-4}$ alkyl, or halo lower alkyl, preferably $C_{1-4}$ haloalkyl, more preferably $CF_3$; and $R^{26}$ and $R^{27}$ are each independently H or alkyl; or (ii) $R^6$ and $R^{26}$ and/or $R^7$ and $R^{27}$ together form alkylene, preferably ethylene, propylene, butylene or pentylene, more preferably propylene; and the remainder of $R^6$, $R^7$, $R^{26}$ and $R^{27}$ are selected as in (i); and $R^{70}$ is alkyl, aryl, heteroaryl, aralkyl, heteroaralkyl, alkoxy, aryloxy, heteroaryloxy, aralkoxy, heteroaralkoxy or $NR^{11}R^{12}$, where $R^{11}$ and $R^{12}$ are each independently H, alkyl, aryl, heteroaryl, aralkyl or heteroaralkyl.

In more preferred embodiments, $R^{30}$ is acetyl and $R^1$ is the side chain of arginine. In these embodiments, the compounds of formula (I) have formula (III):

(III)

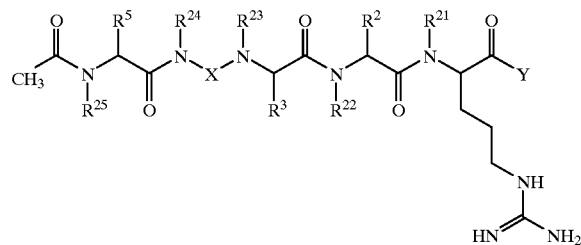

where $R^{21}$ is H or alkyl;

X is a group that allows for flexibility in the chain, preferably alkylene, alkenylene or $CH(R^4)C(O)$;

$R^2$, $R^3$, $R^4$, $R^5$, $R^{22}$, $R^{23}$, $R^{24}$ and $R^{25}$ are each independently selected as in (i) or (ii) as follows:
(i) $R^2$, $R^3$, $R^4$ and $R^5$ are each independently selected from a side chain of a naturally occurring a-amino acid, H, alkyl, preferably lower ($C_{1-6}$) alkyl, alkenyl, preferably $C_{2-10}$ alkenyl, alkynyl, preferably $C_{2-6}$ alkynyl, aryl, aralkyl, aralkenyl, aralkynyl, heteroaryl, heteroaralkyl, heteroaralkenyl, $Z^1$-substituted aryl, aralkyl, aralkenyl or aralkynyl, and $Z^2$-substituted heteroaryl, heteroaralkyl or heteroaralkenyl;

$Z^1$ is selected from halogen, lower alkyl, lower alkoxy, OH, haloalkyl, preferably $CF_3$, $NO_2$, nitrile, alkylthio, phenyl and —NR'R";

each of R' and R" is independently H, alkyl, preferably lower alkyl, OH or halo lower alkyl, particularly $CF_3$;

$Z^2$ is lower alkyl, preferably $C_{1-4}$ alkyl, or halo lower alkyl, preferably $C_{1-4}$ haloalkyl, more preferably $CF_3$;

$R^{22}$, $R^{23}$, $R^{24}$ and $R^{25}$ are each independently H or alkyl; or (ii) $R^2$ and $R^{22}$, and/or $R^3$ and $R^{23}$, and/or $R^4$ and $R^{24}$, and/or $R^5$ and $R^{25}$ together form alkylene, preferably ethylene, propylene, butylene or pentylene, more preferably propylene; and the remainder of $R^2$, $R^3$, $R^4$, $R^5$, $R^{22}$, $R^{23}$, $R^{24}$ and $R^{25}$ are selected as in (i);

Y is a tag group capable of being detected by assays that detect radiolabelled, photochemical, colorimetric, chromogenic, fluorescent, fluorogenic, phosphorescent, electrochemical, chemiluminescent or bioluminescent tags, as described above; and $R^2$, $R^3$, $R^4$, $R^5$, X and Y are unsubstituted or are substituted with one or more substituents selection from Q, which, as defined herein, is halogen, hydroxy, nitrile, nitro, formyl, mercapto, carboxy, hydroxysulfonyl, hydroxyphosphoryl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl, or any two Q groups substituting adjacent atoms on an aryl or heteroaryl group may form 1,3-butadienylene, 1-aza-1,3-butadienylene or 2-aza-1,3-butadienylene.

In embodiments of the compounds, the compounds of formula (I), (II) or (III) are selected as above, with the proviso that the compound is not Ac-Tyr-Ile-Gly-Ser-Arg-pNA, and $R^{30}$ is selected such that the resulting molecule is less than the full-length of any of C4a, C3a or C5a from any species.

In certain embodiments herein, the compounds of formula (II) or (III) are selected such that the P5 residue is a non-aromatic hydrophobic group. Thus, in these embodiments, $R^5$ and $R^{25}$ are selected from (i), (ii) or (iii) as follows:

(i) $R^5$ is the side chain of isoleucine, methionine, leucine, valine, alanine, glycine, serine or threonine; and $R^{25}$ is H or alkyl; or (ii) $R^5$ and $R^{25}$ together form alkylene, preferably ethylene, propylene, butylene or pentylene, more preferably propylene (i.e., the P5 residue is proline); or (iii) $R^5$ is alkyl, preferably lower ($C_{1-6}$) alkyl, alkenyl, preferably $C_{2-10}$ alkenyl, or alkynyl, preferably $C_{2-6}$ alkynyl; and $R^{25}$ is selected as in (i).

In particularly preferred embodiments, the compounds are of formula (I), (II) or (III), where the P3 residue is preferably leucine. This residue is conserved in human, porcine, bovine, rat, mouse and guinea pig C3a, C4a and C5a peptides (see, e.g., Ember et al. in "The Human Complement System in Health and Disease", John E. Bolanakes and Michael M. Frank eds. (Marcel Dekker, 1998).

In other preferred embodiments, the compounds are of formula (I), (II) or (III), where the P4 residue (X) is an amino acid or other group that allows for flexibility in the peptide chain. Preferred P4 residues are glycine, histidine, glutamine, leucine, alkylene or alkenylene, more preferred are glycine and alkylene, most preferred is glycine.

In preferred embodiments, the compounds are of formula (I), (II) or (III), where Y is $SR^{13}$, $OR^{13}$ or $NR^{13}R^{14}$, where $R^{13}$ is alkyl, aryl, heteroaryl, aralkyl and heteroaralkyl and $R^{14}$ is H, alkyl, aryl, heteroaryl, aralkyl and heteroaralkyl, where $HSR^{13}$, $HOR^{13}$ and $HNR^{13}R^{14}$ are capable of being quantitatively assayed by radiolabelled, photochemical, colorimetric, chromogenic, fluorescent, fluorogenic, phosphorescent, electrochemical, chemiluminescent or bioluminescent assays, as described above. Preferred tags are para-nitroanilino (pNA), 4-methylcoumaryl-7-amino (MCA) or (CMA), most preferably para-nitroanilino (pNA).

Presently more preferred compounds of formula (I), (II) or (III) are those where the P1 residue is arginine or lysine, preferably arginine; the P2 residue is alanine, glycine, glutamine, asparagine, threonine or norleucine, preferably glutamine, norleucine or threonine, more preferably norleucine or threonine, most preferably threonine; the P3 residue is leucine; the P4 residue in glycine, histidine, glutamine or leucine, preferably glycine or glutamine, more preferably glycine; and the P5 residue is alanine, leucine, isoleucine, methionine or valine, preferably leucine, alanine or methionine, more preferably alanine.

Presently preferred compounds of formula (I), (II) or (III) include compounds containing the peptides set forth in SEQ ID Nos. 15–19, such as Ac-Ala-Gly-Leu-Asn-Arg-pNA, Ac-Ala-Gly-Leu-Gly-Arg-pNA, Ac-Ala-Gly-Leu-Gln-Arg-pNA, Ac-Ala-Gly-Leu-Thr-Arg-pNA and Ac-Ala-Gly-Leu-Nle-Arg-pNA.

2. Tags

The compounds contain tags at the C-terminal position. The tags are any known to those of skill in the art for use in enzyme assays (see, e.g., U.S. Pat. Nos. 4,448,715, 4,480,030, 4,563,305, 4,568,636, 5,073,487, 5,116,735 and 5,223,403, the disclosures of which are incorporated herein by reference). Preferred tags include, but are not limited to, tags that are capable of being assayed, preferably quantitatively, by radiolabels, by photochemical, colorimetric, chromogenic, fluorescent, fluorogenic, phosphorescent, electrochemical, chemiluminescent or bioluminescent or immunoassays.

More preferred tags are those detectable in calorimetric, chromogenic, fluorescent, fluorogenic, chemiluminescent or bioluminescent assays. Particularly preferred tags are those detectable in a calorimetric, chromogenic, fluorescent or fluorogenic assay format; most preferred are those capable of being assayed in a colorimetric or chromogenic assay.

Among the preferred groups are those the include a tag group that can be a radioactively tagged group, or a fluorogenic tag, a chromogenic tag or a chemiluminescent tag. All of these indicators form either an amide linkage or an ester linkage with L-arginine (or L-Lysine) such that these linkages are cleavable by the enzyme.

Chromogenic and fluorogenic labels and the use thereof are known in this art (see, e.g., U.S. Pat. Nos. 4,448,715; 3,884,896; 3,886,136; 4,016,042; 4,028,318; 4,119,620; 4,147,692; 4,155,916; 4,191,808; 4,191,809 4,207,232; and 4,167,449 which contain lists of specific chromogenic or fluorogenic substrates for various proteolytic enzymes; colorimetric substances are shown in U.S. Pat. Nos. 4,217,269, 4,210,497 and 4,221,706).

Fluorogenic or fluorescent tags suitable for use in the present methods include, but are not limited to, dansyl, 4-methylcoumaryl-7-amino, 4-trifluoromethylcoumaryl-7-amino, naphthylamino, 7-oxycoumaryl, 5-amino-isophthalic acid di(lower alkyl, preferably methyl or ethyl) ester, coumaryl-7-amino tagged with radioactive halogen or $^3$H, or naphthylamino tagged with radioactive halogen of $^3$H. Preferred fluorogenic tags include 4-methylcoumaryl-7-amino or 4-trifluoromethylcoumaryl-7-amino.

When the tag is a fluorogenic tag, it can be 4-methyl coumaryl-7-amino, 4-trifluoromethyl coumaryl-7-amino, naphthylamino, 7-oxy-coumaryl, 5-amino isophthalic acid diethyl ester, dansyl, coumaryl-7-amino, 4-trifluoromethyl coumaryl-7-amino, 2-methylanthranilic acid.

Colorimetric or chromogenic tags suitable for use in the present methods include, but are not limited to, para-nitroanilino, para-nitrophenoxy, ortho-nitrophenoxy, ortho-carboxyphenoxy, nitrophenylamino, 1-carboxy-2-nitrophen-5-ylamino, 1-sulfo-2-nitrophen-5-ylamino, naphthylamino, $\mu$-naphthylamino, $\beta$-naphthylamino, nitronaphthylamino, 5-nitro-$\alpha$-naphthylamino, methoxynaphthylamino, 4-methoxy-$\mu$-naphthylamino, quinonylamino, quinon-5-ylamino, nitroquinonylamino, 8-nitroquinon-5-ylamino, 4-methylcoumaryl-7-amino, 4-trifluoromethylcoumaryl-7-amino, and naphthylamino tagged with radioactive halogen. When the tag is a chromogenic tag, it can be, for example, p-nitro-anilino, p-nitro-phenyloxy, nitrophenylamino, naphthylamino, nitronaphthylamino, methoxynaphthylamino, quinolylamino, nitroquinolylamino, 4-trifluoromethyl coumaryl-7-amino, or naphthylamino. Preferred colorimetric or chromogenic tags include para-nitroanilino and 2-naphthylamino, most preferably para-nitroanilino.

Chemiluminescent tags suitable for use in the present methods include, but are not limited to, luminol (5-amino-2,3-dihydro-1,4-phthalazinedione), iso-luminol (6-amino-2,3-dihydro-1,4-phthalazinedione) and N-(4-aminobutyl)-N-ethyl-iso-luminol (6-(N-(4-aminobutyl)-N-ethylamino)-2,3-dihydrophthalazine-1,4-dione). See, Simpson et al. (1979) *Nature* 279:646.

Radiolabelled tags suitable for use in the present methods include, but are not limited to, either $^{14}$C- or $^3$H-labelled anilino, benzylamino or lower alkoxy; or a halo label, such as 1251 or 1311, in a hydroxyanilino, naphthylamino, hydroxybenzylamino or coumaryl-7-amino group. Preferred radiolabelled tags include $^{14}$C- or $^3$H-labelled anilino or benzylamino; more preferably $^3$H-labelled benzylamino.

When the tag is a radioactively tagged group it can be, for example, a $^{14}$C or a $^3$H] label in anilino, benzylamino, or lower alkoxy; or a halo label in hydroxy anilino, naphthylamino, hydroxybenzylamino or coumaryl-7-amino.

Alternatively, the tag can be a reporter, such as chemiluminescent tag such as, amino-isoluminol, amino-luminol or other luminol derviative; or a bioluminescent tag, such as a luciferin, particularly a coelentrazine, or a luciferase, that upon cleavage is able to react with a suitable luciferase and luciferin, respectively. Also contemplated are immunoreporters, in which a reporter-labeled antibody (or antigen, i.e., ligand) binds to a an antigen (receptor) on Y; and biotin/avidin linked reporters.

3. N-Terminal Capping Groups

The compounds preferably are capped at the N-terminus, but may be used as the free amine. Capping groups are well known to those of skill in the art (see, e.g., Greene "Protecting Groups in Organic Synthesis", second edition (Wiley-Interscience, 1991) and Bodansky et al. "Peptide Synthesis" (Interscience Publishers, 1966)).

Preferred capping groups include, but are not limited to, those that form, together with the nitrogen atom to which they are attached, the following groups: amides, imides, carbamates, ureas, amidines, imidines, thioureas, thioamides, phophinamides, phosphonamides, phosphoramides, sulfonamides, sulfinamides, sulfenamides, sulfinimides and silylamines.

More preferred capping groups are those that form, together with the nitrogen atom to which they are attached, an amide, imide, urea or carbamate group. Thus, preferred capping groups include acetyl, benzoyl, phthalimide, succinimide, maleimide, N-phenylaminocarbonyl, tert-butoxycarbonyl and benzyloxycarbonyl groups, with acyl being particularly preferred, and acetyl being most preferred.

Other preferred capping groups include alkyl, alkenyl, alkynyl, aryl, heteroaryl, aralkyl and heteroaralkyl groups; more preferred are aralkyl and heteroaralkyl groups; most preferred are aralkyl groups, particuarly benzyl groups.

D. Preparation of the compounds

The compounds provided herein may be prepared by methods of peptide synthesis that are well known to those of skill in the art. The desired amino acids, derivatives and isomers thereof can be obtained commercially or can be synthesized according to standard practices and procedures well known in the art. For recent reviews of amino acid and peptide synthesis, see, for example, Bodansky et al. "Peptide Syntesis", Interscience Publishers (1966); Davies, J. S. "Amino Acids, Peptides, and Proteins", vol. 29, The Royal Society of Chemistry: Cambridge, U.K. (1997); Humphrey et al. (1997) *Chem. Rev.* 97(6):2243–2266; Williams in "Advances in Asymmetric Synthesis", vol. 1, Hassner, A., ed., JAI: Greenwich, Conn. (1995); Sauerbrei et al. 11997) *Top. Curr. Chem.* 186:65–86; Easton (1997) *Chem. Rev.* 97(1): 53–82; Dyker (1997) *Angew. Chem., Int. Ed. Eng.* 36(16):1700–1702; Marahiel et al (1997) *Chem. Rev.* 97(7): 2651–2673; and von Dohren et al. (1997) *Chem. Rev.* 97(7):2675–2705; which are incorporated herein by reference. As an example, solid phase synthesis of the peptides disclosed herein is described below.

Briefly, a solid phase sequential coupling procedure can be performed using established methods such as use of an automated peptide synthesizer. Automated synthesizers are commercially available and are well known to those of skill in the art. In this procedure, an amino protected amino acid is bound to a resin support at its carboxyl terminus, the protected amine is deprotected where the peptide linkage is desired, the amino group neutralized with a base and the next amino protected amino acid in the desired sequence is coupled in a peptide linkage. The deprotection, neutralization and coupling steps are repeated until the desired peptide is synthesized. The compounds provided herein may be thus synthesized from their carboxyl terminal end to their amino terminal end. It is to be understood that the compounds provided herein may also be synthesized from their amino terminus to their carboxyl terminus using minor modifications of the methods described herein. The amino protected amino acid can be a conventional amino acid, a derivative or isomer thereof, or a spacer group.

The resin support employed can be any suitable resin conventionally employed in the art for the solid phase preparation of polypeptides. One such resin is polystyrene which has been cross-linked with from about 0.5 to about 3% divinylbenzene, which has been, e.g., benzhydrylamidated, chloromethylated or hydroxymethylated to provide sites for amide or ester formation with the initially introduced amino protected amino acid. Alternatively, the resin support may be, e.g., carboxylated to provide sites for binding the initially introduced carboxyl protected amino acid (for N-terminal C-terminal synthesis).

An example of a hydroxymethyl resin is described by Bodansky et al. ((1966) *Chem. Ind.* (*London*) 38:1597–98). The preparation of chloromethyl and benzhydrylamine resins are described by Stewart et al. ("Solid Phase Peptide Synthesis," 2nd Edition, Pierce Chemical Co., Rockford, Ill. (1984), Chapter 2, pp. 54–55). Many of these resins are available commercially. In general, the amino protected amino acid which is desired on the carboxyl-terminal end of the peptide is bound to the resin using standard procedures and practices as are well known and appreciated in the art. For example, the amino protected amino acid can be bound to the resin by the procedure of Gisin ((1973) *Helv. Chem. Acta* 56:1476). When it is desired to use a resin containing a benzhydrylamine moiety as the resin binding site an amino protected amino acid is coupled to the resin through an amide linkage between the α-carboxylic acid and the amino moiety of the resin. The coupling is effected using standard coupling procedures as described below. Many resin-bound amino acids are available commercially.

The α-amino protecting group employed with each amino acid introduced into the polypeptide sequence may be any such protecting group known in the art. Among the classes of amino protecting groups contemplated are: (1) acyl type protecting groups such as formyl, trifluoroacetyl, phthalyl, 2-toluenesulfonyl (tosyl), benzenesulfonyl, nitrophenylsulfonyl, tritylsulfonyl, o-nitrophenoxyacetyl, and α-chlorobutryl; (2) aromatic urethane type protecting groups such as benzyloxycarbonyl and substituted benzyloxycarbonyls such as p-chlorobenzyloxycarbonyl, p-methoxybenzyloxycarbonyl, p-nitrobenzyloxycarbonyl, p-bromobenzyloxycarbonyl, 1-(p-biphenylyl)-1-methylethoxycarbonyl, α,α-dimethyl-3,5-dimethoxybenzyloxycarbonyl, and benzhydryloxycarbonyl; (3) aliphatic urethane protecting groups such as t-butyloxycarbonyl (BOC), diisopropylmethoxycarbonyl, isopropyloxycarbonyl, ethoxycarbonyl, and allyloxycarbonyl; (4) cycloalkyl urethane type protecting groups such as cyclopentyloxycarbonyl, adamantyloxycarbonyl, and cyclohexyloxycarbonyl; (5) thiourethane type protecting groups such as phenylthiocarbonyl; (6) alkyl type protecting groups such as triphenylmethyl (trityl) and benzyl (Bn); and (7) trialkylsilane protecting groups such as, but not limited to, trimethylsilane. The preferred α-amino protecting group is t-butyloxycarbonyl (BOC); its use as an α-amino protecting group for amino acids is well known to those of skill in the art (see, e.g., Bodansky et al. "The Practice of Peptide Synthesis," Springer-Verlag, Berlin (1984), p. 20).

Following the coupling of the amino protected amino acid to the resin support, the α-amino protecting group may be removed using any suitable procedure such as by using trifluoroacetic acid, trifluoroacetic acid in $CH_2Cl_2$, or HCl in dioxane. The deprotection is carried out at a temperature of between 0° C. and room temperature. Other standard cleaving reagents may be used for removal of specific amino protecting groups under conditions well known and appreciated in the art.

After removal and neutralization of the α-amino protecting group, the next desired amino-protected amino acid is coupled through a peptide linkage. This deprotection, neutralization and coupling procedure is repeated until a peptide of the desired sequence is obtained. Alternatively, multiple amino acid groups may be coupled by the solution method prior to coupling with the resin supported amino acid sequence.

The selection and use of an appropriate coupling reagent is within the skill of the skilled artisan. Particularly suitable coupling reagents where the amino acid to be added is Gln, Asn, or Arg include N,N-dicyclohexylcarbodiimide and 1-hydroxybenzotriazole. The use of these reagents prevents nitrile and lactam formation. Other coupling agents are (1) other carbodiimides (e.g., N-ethyl-N'-(γ-dimethylaminopropylcarbodiimide); (2) ketenimines; (3) isoxazolium salts (e.g., N-ethyl-5-phenylisoxazolium-3-sulfonate); (4) monocyclic nitrogen-containing heterocyclic amides of aromatic character containing one through four nitrogens in the ring such as imidazolides, pyrazolides, and 1,2,4-triazolides (specific heterocyclic amides that are useful include N,N-carbonyldiimidazole and N,N-carbonyl-di-1,2,4-triazole); (5) alkoxylated acetylene (e.g., ethoxyacetylene); (6) reagents which form a mixed anhydride with the carboxyl moiety of the amino acid (e.g., ethyl chloroformate and iso-butyl chloroformate) or the symmetrical anhydride of the amino acid to be coupled (e.g., BOC-Ala-O-Ala-BOC); and (7) nitrogen-containing heterocyclic compounds having a hydroxyl group on one ring nitrogen (such as, but not limited to, N-hydroxyphthalimide, N-hydroxysuccinimide, and 1-hydroxybenzotriazole). Other activating reagents and their use in peptide coupling can be obtained and used as known in the art (see, Kapoor (1970) *J. Pharm. Sci.* 59:1–27).

The preferred coupling method for Gln, Asn and Arg is to react the protected amino acid, or derivatives or isomers thereof, with N,N-dicyclohexylcarbodiimide and 1-hydroxybenzotriazole (1:1) in DMF in the presence of the resin or resin-bound amino acid or peptide. The preferred coupling method for other amino acids involves reacting the protected amino acid, or derivative or isomer thereof, with N,N-dicyclohexylcarbodiimide in $CH_2Cl_2$ to form the symmetrical anhydride. The symmetrical anhydride is then introduced into the solid phase reactor containing the resin or resin-bound amino acid or peptide, and the coupling is carried out in a medium of DMF, or $CH_2Cl_2$, or DMF:$CH_2Cl_2$ (1:1). A medium of DMF is preferred. The success of the coupling reaction at each stage of the synthesis is monitored by a ninhydrin test as described by Kaiser et al. ((1970) *Analyt. Biochem.* 34:595). In cases where incomplete coupling occurs, the coupling procedure is repeated.

After the desired amino acid sequence has been obtained, the peptide is cleaved from the resin. This can be effected by procedures which are well known and appreciated in the art, such as by hydrolysis of the ester or amide linkage to the resin. It is preferred to cleave the peptide from the benzhydrylamine resin with a solution of dimethyl sulfide, p-cresol, thiocresol, or anisole in anhydrous hydrogen fluoride. The cleavage reaction is preferably carried out at temperatures between about 0° C. and about room temperature, and is allowed to continue preferably from between about 5 minutes to about 5 hours.

As is known in the art of solid phase peptide synthesis, many of the amino acids bear side chain functionalities requiring protection during the preparation of the peptide. The selection and use of an appropriate protecting group for these side chain functionalities is within the ability of those skilled in the art and will depend upon the amino acid to be protected and the presence of other protected amino acid residues in the peptide. The selection of such a side chain protection group is critical in that it must not be removed during the deprotection and coupling steps of the synthesis. For example, when BOC is used as the α-amino protecting group, the following side chain protecting groups are suitable: p-toluenesulfonyl (tosyl) moieties can be used to protect the amino side chains of amino acids such as Lys and Arg; p-methylbenzyl, acetamidomethyl, benzyl (Bn), or t-butylsulfonyl moieties can be used to protect the sulfide-containing side chains of amino acids such as cysteine, homocysteine, penicillamine and the like or derivatives thereof; benzyl or cyclohexyl ester moieties can be used to protect carboxylic acid side chains of amino acids such as Asp, Glu; a benzyl ether can be used to protect the hydroxyl-containing side chains of amino acids such as Ser and Thr; and a 2-bromocarbobenzoxy (2Br-Cbz) moiety can be used to protect the hydroxyl-containing side chains of amino acids such as Tyr. These side chain protecting groups are added and removed according to standard practices and procedures well known in the art. It is preferred to deprotect these side chain protecting groups with a solution of anisole in anhydrous hydrogen fluoride (1:10). Typically, deprotection of side chain protecting groups is performed after the peptide chain synthesis is complete but these groups can alternatively be removed at any other appropriate time. It is preferred to deprotect these side chains at the same time as the peptide is cleaved from the resin.

Finally, the C-terminal end of the synthesized peptide is converted to an ester, thioester or amide that, upon enzymatic cleavage, results in the release of a compound that can be assayed by radiolabelled, photochemical, colorimetric, chromogenic, fluorescent, fluorogenic, phosphorescent, electrochemical, chemiluminescent or bioluminescent assays, as described above. Such esters, thioesters or amides may be prepared by procedures well known to those of skill in the art. For example, esters may be prepared in refluxing alcohol using a catalytic amount of a mineral acid or thionyl chloride, or by using standard dehydrative coupling procedures (e.g., 2-chloro-N-methylpyridinium iodide and a tertiary amine). Amides and thioesters may be prepared using standard solution phase peptide coupling techniques, with the amine or thiol substituting for the amino acid residue to be introduced. Thus, para-nitroanilino (pNA) or 4-methylcoumaryl-7-amino (MCA) amides may be prepared by reaction of the peptide carboxylic acid with the corresponding amine in the presence of a peptide coupling agent.

Radiolabelled compounds may be prepared by the procedures set forth in U.S. Pat. Nos. 4,448,715 and 4,563,305, the disclosures of which are incorporated herein by reference. Briefly, radiolabelled esters may be prepared from $^{14}$C- or $^{3}$H-ethanol, both of which are commercially available. Compounds that contain halogen substituents on the C-terminal tag can be radiolabelled, e.g., with $^{125}$I, by halogen exchange. For example, brominated naphthylamino groups can be converted to $^{125}$I substituted naphthylamino groups by halogen exchange. Other radiolabelled tag groups may be synthesized by methods that are well known to those of skill in the art.

Compounds containing colorimetric, chromogenic, fluorometric and fluorogenic tags may be prepared by the methods described in U.S. Pat. Nos. 3,884,896; 3,886,136; 4,016,042; 4,028,318; 4,119,620; 4,147,692; 4,155,916; 4,191,808; 4,191,809; 4,207,232; 4,167,449; 4,480,030; 4,448,715; 4,568,636 and 5,073,487, the disclosures of which are incorporated herein by reference. Briefly, such compounds are C-terminal esters or amides of peptides and peptide derivatives. These esters or amides may be prepared by methods well known to those of skill in the art.

Use of a chemiluminescent tag group has been described previously. See, Schroeder et al. (1976) Anal. Chem. 48:1933.

The compounds are then isolated and purified by standard techniques.

E. Selection of substrates

Any of the compounds described herein may be used as substrates in the assays. Suitable compounds can be selected empirically by performing the assays (see, the EXAMPLES for detailed protocols), and selecting those with detectable activity. Particularly preferred are those that give a signal at least 1 order of magnitude above background within the first thirty minutes of the assay.

F. Kits and diagnostic systems

The assay systems herein may be provided in kit form that is useful for determining activated MASP in a blood or plasma sample. The kits will include a substrate contained in a suitable container or linked to a solid support, such as a microtiter plate or other suitable support, or contained in the wells of a microtiter plate. All kits also include instructions for performing the assays.

The kits will optionally include other reagents for performing the assays, including controls, trypsin, Futhan or other serine protease inhibitor, buffers, such as PBS, stop solutions, and other such reagents. The kits may also include suitable ancillary supplies, such as microtiteir plates, vials, labeled ligand or labeled anti-ligand, calibrator solutions, controls, wash solutions, solid-phase supports and the like.

The packages discussed herein in relation to diagnostic systems are those customarily utilized in diagnostic systems. Such packages include glass and plastic, such as polyethylene, polypropylene and polycarbonate, bottles and vials, plastic and plastic-foil laminated envelopes and the like. The packages may also include containers appropriate for use in auto analyzers. The packages typically include instructions for performing the assays.

G. Methods of Diagnosis Using Complement Activation

The complement system is a fundamental element of normal host defense mechanisms. As a consequence, complement activation is commonly associated with a variety of pathological states such as certain malignancies, myocardial infarction, systemic lupus erythematosus, and adult respiratory distress syndrome. Because of these correlations clinical laboratory methods that detect complement activation are useful in diagnosing certain disease conditions. Unfortunately, as noted above, because of in vivo complement activation, accurate in vivo (ex vivo) measurements of the classical and alternative pathways are difficult to obtain. Furthermore, methods for assessing activity of the lectin pathway are unavailable. Methods for assessing, including detecting and monitoring, the activation level and activity of these various pathways are provided herein. For example, activation of the classical pathway is associated with certain disorders, including inflammatory responses, such as those seen in Alzheimer's disease and bacterial diseases.

Thus, methods for monitoring disorders and conditions associated with in vivo activation of the classical and alternative pathways are provided. In these methods, the activity of MASP is inhibited in EDTA plasma, thereby permitting accurate measurements of components of the complement pathways, particularly the classical and alternative pathways.

Lectin Pathway

In addition, methods for monitoring the lectin pathway components are provided. In particular, a method for monitoring MASP activity in plasma is provided. In the method, in vitro complement activation is assessed as a function of time. This activity results from activated MASP, particularly activated MASP-2, in MBL-MASP complex, the in vitro complement activation, as measured by detecting and monitoring cleavage of the substrate, which is directly proportional to the with MASP activity in the original sample. The activity can be quantitated for example, by measuring the activity at time 0, and as a function of time. The rate of increase and/or the magnitude of the increase in activity reflects MASP activity. The particulars of such determination can be determined empirically.

Alternatively, the amount of activity can be reported as a ratio of MASP activity in the assay, at a selected time, typically about mid-way in the linear portion of the activity vs. time curve, which time can be empirically determined, but is typically between about 10 and 30 minutes, and total MASP, as assess by any means known to those of skill in the art, such as by the known ELISA assays therefor.

Thus methods for detecting and monitoring conditions and diseases associated with the lectin pathway, including but not limited to, tissue and organ injury, particularly transplanted organs and tissues, and viral and parasitic infection are provided.

MBL binds to a variety of microorganisms, coating the targets with activated C4 and activated C3, making them accessible to phagocytic cells that carry these molecules. MBL recognizes complex carbohydrate structures, particularly neutral sugars, and interacts with two associated proteases, MASP-1 and MASP-2. It appears that activated MASP-2 is responsible for C4 cleavage, thus, integrating MBL into the complement system at the C4 activation step. MASP activation is implicated not only responses to microorganisms, but in any response that involves exposing neutral sugars, including by not limited to tissue injury, such as that observed in organ transplants. Thus, monitoring MASP activity provides means to monitor microbial, particularly parasitic, infections, viral infections, particularly CMV (cytomegalovirus), hepatitis virus (HbA and HbB), and HIV infection, and acute and chronic organ rejection.

Elevated ratios compared to normal controls or other standard reflect activation of the lectin pathway, which is correlated with certain disease states and disorders, include viral or parasitic infection, organ transplant rejection, tissue injury and other such states. For a particular patient (human or other mammal) these levels can be monitored to assess disease progress, responses to therapeutic intervention and to detect the onset of such disorders.

Thus, these assays have veterinary applications to detect certain infections or other disease states in farm animals and other animals and to screen therefor.

In other embodiments, animal models for certain disease states can serve as models for drug screening by assessing the effects of candidate drugs on levels of activated MASP.

Futhan and the lectin pathway

Amidines and guanidine derivatives will inhibit complement-mediated hemolysis (i.e. C-activation; see, Otterness et al. (1978) *Biochem. Pharmacol.* 27:1873–1878). Based in part on this information, a potent synthetic inhibitor of complement and coagulation proteinases 6-amidino- 2-naphthyl-4-guanidinobenzoate dimethanesulfonate (trade name Futhan or FUT-175; generic name nafamostat mesilate, which is 6-amidino-2-naphthyl p-guanidinobenzoate dimethanesulfonate) was designed, synthesized and characterized (see, Fujii et al. (1981) *Biochim. BiophyslActa* 661:342–345). This proteinase inhibitor has a broad specificity for serine proteases, and is a potent inhibitor of coagulation and complement proteinases. Futhan inhibits thrombin, plasmin and kallikrein (plasma and pancreatic), all of which can degrade complement components C3, C4 and/or C5 (Hugli (1977) in Chemistry and Biology of Thrombin, Lundblad et al., Eds. p. 345, Ann Arbor Science, Ann Arbor, Mich.; Pfeiffer et al. (1997) in Techniques in Protein Chemistry VIII Techniques in Protein Chemistry VIII, Marshak, Ed., pp. 363–369, Academic Press, San Diego). Studies have focused on identifying complement proteinase targets of Futhan, which include C1r, C1s, Factor B, and D (Ikari et al. (1983) *Immunology* 49:685–691). This inhibitor is also effective toward Hageman factor and Factor Xa at the sub-micromolar level (Hitomi et al. (1985) *Haemostasis* 15:164–168). Several studies have examined the in vivo protective effects of Futhan in various models of immunological reactions including Forssman shock in guinea pigs, passive cutaneous anaphylaxis in rats, and delayed hypersensitivity reactions and endotoxin shock in mice (Hitomi et al. (1982) *Int. Arch. Allergy Appl. Immunol.* 69:262–267; Iwaki et al. (1986) *Japan J. Pharmacol.* 41:155–162). Since Futhan inhibits complement-mediated hemolysis by the alternative and classical pathways (Watkins et al. (1989) *Lancet* 1:896–897), it was concluded that the major effect of this compound on in vivo immunological reactions resulted from direct inhibition of enzymes in the C-activation pathways.

Studies have been undertaken to characterize Futhan activity in vivo and to identify the various proteases that it inhibits. It has been shown that Futhan effectively stabilizes freshly drawn blood samples from normal individuals permitting direct measurement of the anaphylatoxins C3a and C4a (Pfeiffer et al. (1997) in Techniques in Protein Chemistry VIII Techniques in Protein Chemistry VIII, Marshak, Ed., pp. 363–369, Academic Press, San Diego).

For purposes herein, addition of Futhan to the samples of blood or plasma inhibits MASP activity. Such samples thus can serve as negative controls for the assays herein.

The following example is included for illustrative purposes only and are not intended to limit the scope of the invention.

EXAMPLE 1

Assays Using Exemplary Substrates Were Performed

Reagents: Futhan was obtained from Banyu Pharm. Co., LTD., Tokyo, Japan. The complement C3a (code RPA 518) and C4a (code RPA 519) Biotrak RIA assay kits were obtained from Amersham Life Sciences, Arlington Heights, Ill. EDTA Na$_4$(sigma grade) was purchased from Sigma, St Louis, Mo. All other chemicals, buffer salts and reagents were analytical reagent grade.

Blood processing protocols: Blood samples were either drawn into EDTA tubes (Venoject, Terumo Corp. Elkston, Md.) or Futhan/EDTA tubes (Venoject, Terumo Europe, Leuven, Belgium). The plasma was collected immediately by centrifugation at 2000 g for 15 min. at 4° C. unless otherwise indicated. The plasma samples were either processed immediately for analysis or snap frozen in liquid nitrogen and stored at −70° C. Frozen samples were thawed at 4° C. and processed.

Preparation of the assay plates

Fifty μl peptide solution (MASP substrate, such as Ac-Ala-Leu-Gly-Gln-Arg-pNA; SEQ ID NOs. 15–19) containing 1 mg/ml peptide dissolved in distilled water is delivered into designated 1 wells of a 96 well microtiter plate (Costar ELMUA flat bottom-well Cat. #3590, or equivalent or higher density or lower density format), and dried overnight at 37° C. Designated "control" wells background absorption control) receive no peptide. The dry plates are sealed with a plastic plate sealer (Cost& Cat. #3095, or equivalent) and stored at 4° C. until use, up to about four weeks.

Assay procedure:

MASP Activity

EDTA plasma samples are collected according to standard blood drawing procedures and stored at −20° C. or −70° C. until use. To measure MASP activity, the samples are thawed, 50 µl of the plasma is diluted to 500 µl with phosphate buffered saline (PBS) buffer, pH=7.9 (ten fold dilution). For duplicate measurement, 100 µl each of the diluted sample is delivered into two "assay" wells (peptide-containing wells) and one control well. The plate is incubated at 37° C., and optical density at 405 nm is measured and recorded (using a microplate reader fitted with a 405 nm filter) at the following time points: 0, 2, 5, 10, 15, 25, 35,45 and 60 min. OD value of the control well is subtracted from the average obtained for the assay wells, and the data are plotted (OD versus time).

The rate of increase in OD as a function of time reflects the amount of activated MASP that was present in circulation. Alternatively, since the amount of MASP activity is substantial relative to other proteases in the mixture. The amount of MASP activity in the reaction, if taken at a time point in the linear range of increase, reflects that amount of activated MASP in vivo.

Controls

The assays can be performed as above, except that Futhan, sufficient to inhibit MASP (about 0.05 mg/ml Futhan) is added to each well tested, and substrate cleavage is assessed. Any cleavage reflects cleavage that is not attributable to MASP.

Results

Exemplary assays have been performed using the following exemplary substrates:

P#3 Ac-Ala-Gly-Leu-Gln-Arg-pNA;

P#5 Ac-Ala-Gly-Leu-Asn-Arg-pNA;

P#6 Ac-Ala-Gly-Leu-Thr-Arg-pNA; and

P#7 Ac-Ala-Gly-Leu-Nle-Arg-pNA.

The results are set forth in FIG. 1. The figure shows that different substrates are more active with plasma from different species. These results suggest that species-specific assays systems can be devised.

EXAMPLE 2

KITS for Practice of the Assay

Background

MASP is activated by neutral sugars, such as mannose. Any event that exposes neutral sugars should activate the MASP enzyme. The MASP enzyme is activated in the complex, but not active in fluid phase on the substrate C3 and C4, calcium ions are removed, such as by metal chelation in vitro. In vivo it appears that the MASP enzyme acts locally in the complex by achieving high effecting concentrations at the site of action, such as a viral particle or injured cell surface.

MASP activity can be used as a indicator of certain diseases or disorders, particularly any that involve exposure of neutral sugars, such as viral and parasitic infection and tissue injury, particularly immune injury. Also, tissue injury leading to exposure of neutral sugars on the cell surface can activate MASP enzyme. Mechanism for MASP activation in tissue injury.

Summary of the Assay

This assay is based on the selective cleavage of a synthetic substrate by the MASP-2 enzyme in plasma. The zero order rate of cleavage is directly proportional to the level of activated enzyme according to the formula velocity=k[E], where the rate of cleavage or velocity equals k (the rate constant) times the enzyme concentration [E]. The relative [E] value is obtained by determining the slope of the zero order portion of the curve formed by plotting the amount of substrate cleaved (O.D. units) versus time. The conversion of the substrate is measured at 405 nm and the extinction value is #O.D. units per nanomole. A milliunit of MASP activity is defined as cleavage of one nanomole of substrate per minute at 37° C. The average level of MASP measured in normal EDTA plasma (n=10) is # milliunits.

The milliunits of MASP in the sample are calculated as follows: O.D. units per min×dilution of sample/# O.D. units per nanomole substrate:.

The assay system, which should be stored at 2–8° C. until used, contains the following components for assaying forty samples.

Components of the kits

Pre-loaded 96-well plate

The plate is pre-loaded with MASP-2 susbtrate, such that 40 wells contain the substrate and 40 do not. Sample should be applied to all 80 wells so that background absorbance can be subtracted.

Assay buffer

The assay buffer contains 0.15N saline and 0.05 M phosphate (PBS) buffer at pH 7.5 for use to dilute samples.

Reaction stop solution

The stop solution contains 0.05 mg/ml futhan (or dilute acetic acid) to terminate the enzymatic reaction.

Standard Trypsin solution

Five wells containing various levels of substrate are designated standard wells (A–E). A vial containing 10 µg trypsin is included and 1.0 ml of the assay buffer should be added to the vial containing the trypsin. 100 µl of the resulting trypsin solution should be added to each of the standard wells.

After 30 min at 37° C., the standard wells should give the following readings:

| Well | O.D. Range |
|------|------------|
| A | 0.1–0.2 |
| B | 0.3–0.4 |
| C | 0.5–0.6 |
| D | 0.7–0.8 |
| E | 1.0–1.2 |

Since modifications will be apparent to those of skill in this art, it is intended that this invention be limited only by the scope of the appended claims.

What is claimed is:

1. A method for determining in vivo levels of activated mannan-binding protein-associated serine protease (MASP) enzyme, comprising:

contacting a sample of blood or plasma that comprises a metal ion chelator with a compound of formula:

R-peptide-Y, wherein one or both of R and Y are detectable upon cleavage of Y or a portion of the peptide comprising Y, and the peptide comprises a site recognized by a MASP enzyme; and measuring the rate of cleavage or the amount of cleavage at about the $t_{1/2}$ relative to the maximum level of activation.

2. The method of claim 1, wherein, the peptide comprises at least 4 residues from the C-terminus of an anaphylatoxin selected from C3a, C4a and C5a.

3. The method of claim 2, wherein the anaphylatoxins comprise a sequence of amino acids set forth in one of SEQ ID Nos. 1–14.

4. The method of claim 1, wherein R is a peptide blocking group, protecting group or capping group.

5. The method of claim 1, wherein R is selected from Cbz, Boc, FMoc, and Ac.

6. The method of claim 1, wherein Y is any group cleavable from the compound by MASP and comprises a radiolabelled, photochemical, colorimetric, chromogonic, fluorescet, fluorogenic, phosphorescent, electrochemical, chemiluminescent or bioluminescently-labelled tag or, where R comprises a tag, Y is an amino acid residue such that upon cleavage, the tag on R is detectable.

7. The method of claim 1, wherein the compound of has formula (I):

$$R^{30}\text{-}N(R^{25})\text{-}CH(R^5)\text{-}C(O)\text{-}N(R^{24})\text{-}CH(R^{23})\text{-}X\text{-}N\text{-}CH(R^3)\text{-}C(O)\text{-}N(R^{22})\text{-}CH(R^2)\text{-}C(O)\text{-}N(R^{21})\text{-}CH(R^1)\text{-}Y$$ (I)

or analogs thereof:, wherein:

R is $R^{30}$;

$R^1$ is $R^{60}$-A, where A is $NH_t(R^{40})_{3-t}$, heterocyclyl, heteroaryl, guanidinyl, amidino or imino, and is capable of forming a cationic salt at physiological pH, or is $N^+(R^{40})_4$;

$R^{60}$ is alkylene, alkenylene, alkynylene, cycloalkylene, heterocyclylene, aralkylene, heteroaralkylene, arylene or heteroarylene;

$R^{40}$ is alkyl, alkenyl, alkynyl, aryl or heteroaryl;

t is 0–3;

$R^{21}$ is H or alkyl;

X is alkylene, alkenylene or $CH(R^4)C(O)$;

$R^2$, $R^3$, $R^4$, $R^5$, $R^{22}$, $R^{23}$, $R^{24}$, $R^{25}$ and $R^{30}$ are each independently selected as in (i) or (ii) as follows:

(i) $R^2$, $R^3$, $R^4$ and $R^5$ are each independently selected from a side chain of a naturally occurring α-amino acid, H, alkyl, alkenyl, alkynyl, aryl, aralkyl, aralkenyl, aralkynyl, heteroaryl, heteroaralkyl, heteroaralkenyl, $Z^1$-substituted aryl, aralkyl, aralkenyl or aralkynyl, and $Z^2$-substituted heteroaryl, heteroaralkyl or heteroaralkenyl;

$Z^1$ is selected from halogen, lower alkyl, lower alkoxy, OH, haloalkyl, $NO_2$, nitrile, alkylthio, phenyl and —NR'R";

each of R'R" is independently H, alkyl, OH or halo lower alkyl;

$Z^2$ is lower alkyl or halo lower alkyl;

$R^{22}$, $R^{23}$ and $R^{24}$ are each independently H or alkyl; and $R^{30}$ and $R^{25}$ are each independently selected as in (a), (b) or (c) as follows:

(a) $R^{30}$ is a peptide residue containing from 1 or more amino acid residues such that the compound contains at least two contiguous amino acids from the C-terminal portion of any one of SEQ ID NOS. 1 through 14 or other anaphylatoxin selected from C3a, C4a, and C5a, and the resulting peptide is cleaved by a MASP; and $R^{25}$ is H or alkyl; or (b) $R^{30}$ and $R^{25}$ are each independently H, $C(O)R^{10}$, alkyl, alkenyl, alkynyl, aryl, heteroaryl, aralkyl, heteroaralkyl, $Si(R^{10})_3$, $S(O)_m R^{10}$ where m is 0–2 or $P(O)_n(R^{10})_p$ where n is 0–3; p is 1–2; $R^{10}$ is alkyl, aryl, heteroaryl, aralkyl, heteroaralkyl, alkoxy, aryloxy, heteroaryloxy, aralkoxy, heteroaralkoxy or $NR^{11}R^{12}$; and $R^{11}$ and $R^{12}$ are each independently selected from among H, alkyl, aryl, heteroaryl, aralkyl and heteroaralkyl; or (c) $R^{30}$ and $R^{25}$, together with the nitrogen atom to which they are attached, form a heterocyclyl, heteroaryl, cyclic amide or cyclic imide group; or (ii) $R^2$ and $R^{22}$, and/or $R^3$ and $R^{23}$, and/or $R^4$ and $R^{24}$, and/or $R^5$ and $R^{25}$ together form alkylene; and the remainder of $R^2$, $R^3$, $R^4$, $R^5$, $R^{22}$, $R^{23}$, $R^{24}$, $R^{25}$ and $R^{30}$ are selected as in (i);

Y is any group cleavable from the compound by MASP and comprises a radiolabelled, photochemical, colorimetric, chromogenic, fluorescent, fluorogenic, phosphorescent, electrochemical, chemiluminescent or bioluminescently-labelled tag or, where R comprises a tag, Y is an amino acid residue such that upon cleavage the tag on R is detectable; and $R^1$, $R^2$, $R^3$, $R^4$, $R^5$, $R^{25}$, $R^{30}$, X and Y are unsubstituted or are substituted with one or more substituents selection from Q, which, as defined herein, is halogen, hydroxy, nitrile, nitro, formyl, mercapto, carboxy, hydroxysulfonyl, hydroxyphosphoryl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl, or any two Q groups substituting adjacent atoms on an aryl or heteroaryl group may form 1,3-butadienylene, 1-aza-1,3-butadienylene or 2-aza-1, 3-butadienylene.

8. The method of claim 7, wherein A is $NH_t(R^{40})_{3-t}$, heterocyclyl, heteroaryl, guanidinyl or imino; where $R^{40}$ is selected from alkyl, alkenyl and alkynyl.

9. The method of claim 7, wherein $R^1$ is the side chain of lysine or arginine.

10. The method of claim 7, wherein $R^1$ is the side chain of arginine.

11. The method of claim 7, wherein A is $N^+(R^{40})_4$.

12. The method of claim 7, wherein $R^5$, $R^{25}$ and $R^{30}$ are selected from (i), (ii) or (iii) as follows:
  (i) $R^5$ is the side chain of isoleucine, methionine, leucine, valine, alanine, glycine, serine or threonine; and $R^{25}$ and $R^{30}$ are selected as in (a), (b) or (c) as follows:
    (a) $R^{30}$ is a peptide containing from 1 to 71 amino acid residues such that the compound contains the C-terminal portion of any one of SEQ ID Nos. 1 through 14, and $R^{25}$ is H or alkyl; or
    (b) $R^{30}$ and $R^{25}$ are each independently H, $C(O)R^{10}$, alkyl, alkenyl, alkynyl, aryl, heteroaryl, aralkyl, heteroaralkyl, $Si(R^{10})_3$, $S(O)_mR^{10}$ where m is 0–2 or $P(O)_n(R^{10})_p$ where n is 0–3; p is 1–2; $R^{10}$ is alkyl, aryl, heteroaryl, aralkyl, heteroaralkyl, alkoxy, aryloxy, heteroaryloxy, aralkoxy, heteroaralkoxy or $NR^{11}R^{12}$; and $R^{11}$ and $R^{12}$ are each independently selected from among H, alkyl, aryl, heteroaryl, aralkyl and heteroaralkyl; or
    (c) $R^{30}$ and $R^{25}$, together with the nitrogen atom to which they are attached, form a heterocyclyl, heteroaryl, cyclic amide or cyclic imide group; or
  (ii) $R^5$ and $R^{25}$ together form alkylene; and $R^{30}$ is selected as in (i)(a) or (i)(b); or
  (iii) $R^5$ is alkyl, alkenyl or alkynyl; and $R^{25}$ and $R^{30}$ are selected as in (i).

13. The method of claim 1, wherein:
the compound has formula (II):

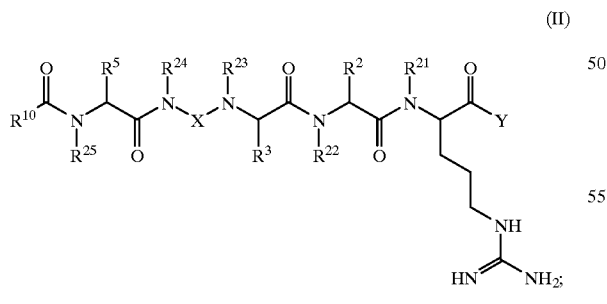

(II)

R is $R^{30}$;
$R^{21}$ is H or alkyl;
X is alkylene, alkenylene or $CH(R^4)C(O)$;
$R^{10}$ is selected from (i) or (ii) as follows:
  (i) alkyl, aryl, heteroaryl, aralkyl, heteroaralkyl, alkoxy, aryloxy, heteroaryloxy, aralkoxy, heteroaralkoxy or $NR^{11}R^{12}$; or (ii) $R^{10}$ contains 1–5 amino acid residues or analogs thereof, with the N-terminus capped with $C(O)R^{70}$;
$R^{70}$ is alkyl, aryl, heteroaryl, aralkyl, heteroaralkyl, alkoxy, aryloxy, heteroaryloxy, aralkoxy, heteroaralkoxy or $NR^{11}R^{12}$;
$R^{11}$ and $R^{12}$ are each independently H, alkyl, aryl, heteroaryl, aralkyl or heteroaralkyl;
$R^2$, $R^3$, $R^4$, $R^5$, $R^{22}$, $R^{23}$, $R^{24}$ and $R^{25}$ are each independently selected as in (i) or (ii) as follows:
  (i) $R^2$, $R^3$, $R^4$ and $R^5$ are each independently selected from a side chain of a naturally occurring α-amino acid, H, alkyl, alkenyl, alkynyl, aryl, aralkyl, aralkenyl, aralkynyl, heteroaryl, heteroaralkyl, heteroaralkenyl, $Z^1$-substituted aryl, aralkyl, aralkenyl or aralkynyl, and $Z^2$-substituted heteroaryl, heteroaralkyl or heteroaralkenyl;
$Z^1$ is selected from halogen, lower alkyl, lower alkoxy, OH, haloalkyl, $NO_2$, nitrile, alkylthio, phenyl and —NR'R";
each of R' and R" is independently H, alkyl, OH or halo lower alkyl;
$Z^2$ is lower alkyl or halo lower alkyl;
$R^{22}$, $R^{23}$, $R^{24}$ and $R^{25}$ are each independently H or alkyl; or
  (ii) $R^2$ and $R^{22}$, and/or $R^3$ and $R^{23}$, and/or $R^4$ and $R^{24}$, and/or $R^5$ and $R^{25}$ together form alkylene; and the remainder of $R^2$, $R^3$, $R^4$, $R^5$, $R^{22}$, $R^{23}$, $R^{24}$ and $R^{25}$ are selected as in (i);
Y is a tag group capable of being assayed by radiolabelled, photochemical, colorimetric, chromogenic, fluorescent, fluorogenic, phosphorescent, electrochemical, chemiluminescent or bioluminescent assays; and
$R^2$, $R^3$, $R^4$, $R^5$, X and Y are unsubstituted or are substituted with one or more substituents selection from Q, which, as defined herein, is halogen, hydroxy, nitrile, nitro, formyl, mercapto, carboxy, hydroxysulfonyl, hydroxyphosphoryl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl, or any two Q groups substituting adjacent atoms on an aryl or heteroaryl group may form 1,3-butadienylene, 1-aza-1,3-butadienylene or 2-aza-1, 3-butadienylene.

14. The method of claim 13, wherein $R^{10}$ is alkyl, aryl, heteroaryl, aralkyl, heteroaralkyl, alkoxy, aryloxy, heteroaryloxy, aralkoxy, heteroaralkoxy or $NR^{11}R^{12}$.

15. The method of claim 13, wherein:
$R^{10}$ is selected from $CH(R^6)$—$NH(R^{26})$—$C(O)R^{70}$ and $CH(R^6)$—$NH(R^{26})C(O)$—$CH(R^7)$—$NH(R^{27})$—C (O)—$R^{70}$, where $R^6$, $R^7$, $R^{26}$ and $R^{27}$ are each independently selected from (i) or (ii) as follows:
(i) $R^6$ and $R^7$ are each independently selected from a side chain of a naturally occurring α-amino acid, H, alkyl, alkenyl, alkynyl, aryl, aralkyl, aralkenyl, aralkynyl, heteroaryl, heteroaralkyl, heteroaralkenyl, $Z^1$-substituted aryl, aralkyl, aralkenyl or aralkynyl, and $Z^2$-substituted heteroaryl, heteroaralkyl or heteroaralkenyl;
$Z^1$ is selected from halogen, lower alkyl, lower alkoxy, OH, haloalkyl, $NO_2$, nitrile, alkylthio, phenyl and —NR'R";
each of R' and R" is independently H, alkyl, OH or halo lower alkyl;
$Z^2$ is lower alkyl or halo lower alkyl; and
$R^{26}$ and $R^{27}$ are each independently H or alkyl; or
(ii) $R^6$ and $R^{26}$ and/or $R^7$ and $R^{27}$ together form alkylene; and the remainder of $R^6$, $R^7$, $R^{26}$ and $R^{27}$ are selected as in (i); and
$R^{70}$ is alkyl, aryl, heteroaryl, aralkyl, heteroaralkyl, alkoxy, aryloxy, heteroaryloxy, aralkoxy, heteroaralkoxy or $NR^{11}R^{12}$, where $R^{11}$ and $R^{12}$ are each independently H, alkyl, aryl, heteroaryl, aralkyl or heteroaralkyl.

16. The method of claim 1 wherein: the compound has formula (III):

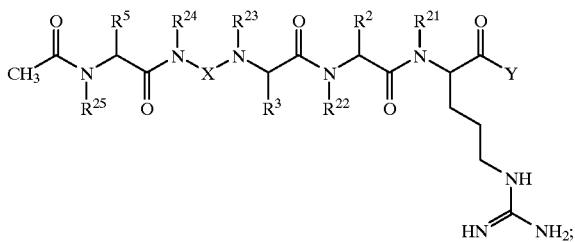

(III)

R is $R^{30}$;
$R^{21}$ is H or alkyl;
X is alkylene, alkenylene or $CH(R^4)C(O)$;
$R^2$, $R^3$, $R^4$, $R^5$, $R^{22}$, $R^{23}$, $R^{24}$ and $R^{25}$ are each independently selected as in (i) or (ii) as follows:
(i) $R^2$, $R^3$, $R^4$ and $R^5$ are each independently selected from a side chain of a naturally occurring α-amino acid, H, alkyl, alkenyl, alkynyl, aryl, aralkyl, aralkenyl, aralkynyl, heteroaryl, heteroaralkyl, heteroaralkenyl, $Z^1$-substituted aryl, aralkyl, aralkenyl or aralkynyl, and $Z^2$-substituted heteroaryl, heteroaralkyl or heteroaralkenyl;
$Z^1$ is selected from halogen, lower alkyl, lower alkoxy, OH, haloalkyl, $NO_2$, nitrile, alkylthio, phenyl and —NR'R";
each of R' and R" is independently H, alkyl, OH or halo lower alkyl;
$Z^2$ is lower alkyl or halo lower alkyl;
$R^{22}$, $R^{23}$, $R^{24}$ and $R^{25}$ are each independently H or alkyl; or
(ii) $R^2$ and $R^{22}$, and/or $R^3$ and $R^{23}$, and/or $R^4$ and $R^{24}$, and/or $R^5$ and $R^{25}$ together form alkylene; and the remainder of $R^2$, $R^3$, $R^4$, $R^5$, $R^{22}$, $R^{23}$, $R^{24}$ and $R^{25}$ are selected as in (i);
Y is a tag group capable of being assayed by radiolabelled, photochemical, colorimetric, chromogenic, fluorescent, fluorogenic, phosphorescent, electrochemical, chemiluminescent or bioluminescent assays; and $R^2$, $R^3$, $R^4$, $R^5$, X and Y are unsubstituted or are substituted with one or more substituents selection from Q, which, as defined herein, is halogen, hydroxy, nitrile, nitro, formyl, mercapto, carboxy, hydroxysulfonyl, hydroxyphosphoryl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl, or any two Q groups substituting adjacent atoms on an aryl or heteroaryl group may form 1,3-butadienylene, 1-aza-1,3-butadienylene or 2-aza-1, 3-butadienylene.

17. The method of claim 16, wherein $R^5$ and $R^{25}$ are selected from (i), (ii) or (iii) as follows:
(i) $R^5$ is the side chain of isoleucine, methionine, leucine, valine, alanine, glycine, serine or threonine; and $R^{25}$ is H or alkyl; or
(ii) $R^5$ and $R^{25}$ together form alkylene; or
(iii) $R^5$ is alkyl, alkenyl or alkynyl; and $R^{25}$ is selected as in (i).

18. The method of claim 16, wherein $R^5$ and $R^{25}$ are selected from (i), (ii) or (iii) as follows:
(i) $R^5$ is the side chain of isoleucine, methionine, leucine, valine, alanine, glycine, serine or threonine; and $R^{25}$ is H or alkyl; or
(ii) $R^5$ and $R^{25}$ together form alkylene; or
(iii) $R^5$ is alkyl, alkenyl or alkynyl; and $R^{25}$ is selected as in (i).

19. The method of claim 7, wherein $R^3$ is the side chain of leucine.

20. The method of claim 13, wherein $R^3$ is the side chain of leucine.

21. The method of claim 16, wherein $R^3$ is the side chain of leucine.

22. The method of claim 7, wherein X is alkylene or $CH(R^4)C(O)$ where $R^4$ is H.

23. The method of claim 13, wherein X is alkylene or $CH(R^4)C(O)$ where $R^4$ is H.

24. The method of claim 16, wherein X is alkylene or $CH(R^4)C(O)$ where $R^4$ is H.

25. The method of claim 7, wherein Y is $SR^{13}$, $OR^{13}$ or $NR^3R^{14}$, where $R^{13}$ is alkyl, aryl, heteroaryl, aralkyl and heteroaralkyl and $R^{14}$ is H, alkyl, aryl, heteroaryl, aralkyl and heteroaralkyl, wherein $HSR^{13}$, $HOR^{13}$ and $HNR^{13}R^{14}$ are capable of being quantitatively assayed by radiolabelled, photochemical, colorimetric, chromogenic, fluorescent, fluorogenic, phosphorescent, electrochemical, chemiluminescent or bioluminescent assays.

26. The method of claim 13, wherein Y is $SR^{13}$, $OR^{13}$ or $NR^{13}R^{14}$, where $R^{13}$ is alkyl, aryl, heteroaryl, aralkyl and heteroaralkyl and $R^{14}$ is H, alkyl, aryl, heteroaryl, aralkyl and heteroaralkyl, wherein $HSR^{13}$, $HOR^{13}$ and $HNR^{13}R^{14}$ are capable of being quantitatively assayed by radiolabelled, photochemical, colorimetric, chromogenic, fluorescent, fluorogenic, phosphorescent, electrochemical, chemiluminescent or bioluminescent assays.

27. The method of claim 16, wherein Y is $SR^{13}$, $OR^{13}$ or $NR^{13}R^{14}$, where $R^{13}$ is alkyl, aryl, heteroaryl, aralkyl and heteroaralkyl and $R^{14}$ is H, alkyl, aryl, heteroaryl, aralkyl and heteroaralkyl, wherein $HSR^{13}$, $HOR^{13}$ and $HNR^{13}R^{14}$, and Y is labeled for quantitatively detection by radiolabelled, photochemical, colorimetric, chromogenic, fluorescent, fluorogenic, phosphorescent, electrochemical, chemiluminescent or bioluminescent assays.

28. The method of claim 1, wherein Y is selected from 4-methyl coumaryl-7-amino, 4-trifluoromethyl coumaryl-7-amino, dansyl, naphthylamino, 7-oxy-coumaryl, 5-amino isophthalic acid diethyl ester, dansyl, coumaryl-7-amino, 4-trifluoromethyl coumaryl-7-amino, 2-methylanthranilic acid, para-nitroanilino, para-nitrophenoxy, ortho-nitrophenoxy, ortho-carboxyphenoxy, nitrophenylamino, 1-carboxy-2-nitrophen-5-ylamino, 1-sulfo-2-nitrophen-5-ylamino, naphthylamino, $\mu$-naphthylamino, $\beta$-naphthylamino, nitronaphthylamino, 5-nitro-$\alpha$-naphthylamino, riboflavin methoxynaphthylamino, 4-methoxy-$\mu$-naphthylamino, quinonylamino, a luminol, isoluminol, a luciferin, quinon-5-ylamino, nitroquinonylamino, 8-nitroquinon-5-ylamino, 4-methylcoumaryl-7-amino, 4-trifluoromethylcoumaryl-7-amino, and naphthylamino tagged with radioactive halogen.

29. The method of claim 27, wherein Y is para-nitroanilino (pNA) or 4-methylcoumaryl-7-amino (MCA).

30. The method of claim 1, wherein R and Y comprise a detectable tag.

31. The method of claim 29, wherein R is a fluoroscent tag and Y comprises a colorimetric, wherein the fluorescence of R is quenched until cleavage of Y.

32. The method of claim 30, wherein R comprises 2-methylanthranilic acid.

33. The method of claim 31, where Y comprises pNA.

34. The method of claim 7, wherein:
   $R^1$ is the side chain of arginine or lysine;
   $R^2$ is the side chain of alanine, glycine, glutamine, asparagine, threonine or norleucine;
   $R^3$ is the side chain of leucine;
   $R^4$ is the side chain of glycine, histidine, glutamine or leucine; and
   $R^5$ is the side chain of alanine, leucine, isoleucine, methionine or valine.

35. The method of claim 13, wherein:
   $R^2$ is the side chain of alanine, glycine, glutamine, asparagine, threonine or norleucine;
   $R^3$ is the side chain of leucine;
   $R^4$ is the side chain of glycine, histidine, glutamine or leucine; and
   $R^5$ is the side chain of alanine, leucine, isoleucine, methionine or valine.

36. The method of claim 16, wherein:
   $R^2$ is the side chain of alanine, glycine, glutamine, asparagine, threonine or norleucine;
   $R^3$ is the side chain of leucine;
   $R^4$ is the side chain of glycine, histidine, glutamine or leucine; and
   $R^5$ is the side chain of alanine, leucine, isoleucine, methionine or valine.

37. The method of claim 1, selected from the group consisting of Ac-Ala-Gly-Leu-Asn-Arg-pNA, Ac-Ala-Gly-Leu-Gly-Arg-pNA, Ac-Ala-Gly-Leu-Gln-Arg-pNA, Ac-Ala-Gly-Leu-Thr-Arg-pNA and Ac-Ala-Gly-Leu-Nle-Arg-pNA.

38. The method of claim 1 that is Ac-Ala-Gly-Leu-Thr-Arg-pNA.

39. The method of claim 1, wherein Y is a group capable of being assayed by a colorimetric, chromogenic, fluorometric or fluorogenic assay.

40. The method of claim 1, wherein Y is selected from the group consisting of 4-methylcoumaryl-7-amino, 4-trifluoromethylcoumaryl-7-amino, naphthylamino, 7-oxycoumaryl, 5-amino-iso-phthalic acid di(methyl or ethyl) ester, para-nitroanilino, para-nitrophenoxy, ortho-nitrophenoxy, ortho-carboxyphenoxy, nitrophenylamino, 1-carboxy-2-nitrophen-5-ylamino, 1-sulfo-2-nitrophen-5-ylamino, $\mu$-naphthylamino, $\beta$-naphthylamino, nitronaphthylamino, 5-nitro-$\alpha$-naphthylamino, methoxynaphthylamino, 4-methoxy-$\mu$-naphthylamino, quinonylamino, quinon-5-ylamino, nitroquinonylamino and 8-nitroquinon-5-ylamino.

41. The method of claim 1, wherein the compound is selected from the group consisting of:
   R-Ala-Gly-Leu-Gln-Arg-Y,
   R-Ala-Gly-Leu-Asn-Arg-Y,
   R-Ala-Gly-Leu-Thr-Arg-Y,
   R-Ala-Gly-Leu-Nle-Arg-,
   R-Ala-Gly-Leu-Nle-Arg-Y, and
   R-Leu-Ala-Arg-Y.

42. The method of claim 1, wherein the compound is selected from the group consisting of:
   Ac-Ala-Gly-Leu-Gln-Arg-pNA,
   Ac-Ala-Gly-Leu-Asn-Arg-pNA,
   Ac-Ala-Gly-Leu-Thr-Arg-pNA,
   Ac-Ala-Gly-Leu-Nle-Arg-pNA,
   Ac-Ala-Gly-Leu-Nle-Arg-pNA, and
   Ac-Leu-Ala-Arg-pNA.

43. A compound of formula (I):

$$R^{30}\diagdown\underset{R^{25}}{N}-\underset{R^{5}}{\overset{}{C}}-\underset{O}{\overset{}{C}}-\underset{R^{24}}{N}-X-\underset{R^{23}}{N}-\underset{R^{3}}{\overset{O}{C}}-\underset{R^{22}}{N}-\underset{R^{2}}{\overset{}{C}}-\underset{O}{\overset{}{C}}-\underset{R^{21}}{N}-\underset{R^{1}}{\overset{O}{C}}-Y \quad (I)$$

or analogs thereof:, wherein:
   $R^1$ is $R^{60}$-A, where A is $NH_t(R^{40})_{3-t}$, heterocyclyl, heteroaryl, guanidinyl, amidino or imino, and is capable of forming a cationic salt at physiological pH, or is $N^+(R^{40})_4$;
   $R^{60}$ is alkylene, alkenylene, alkynylene, cycloalkylene, heterocyclylene, aralkylene, heteroaralkylene, arylene or heteroarylene;
   $R^{40}$ is alkyl, alkenyl, alkynyl, aryl or heteroaryl;
   t is 0–3;
   $R^{21}$ is H or alkyl;
   X is alkylene, alkenylene or $CH(R^4)C(O)$;
   $R^2$, $R^3$, $R^4$, $R^5$, $R^{22}$, $R^{23}$, $R^{24}$, $R^{25}$ and $R^{30}$ are each independently selected as in (i) or (ii) as follows:
      (i) $R^2$, $R^3$, $R^4$ and $R^5$ are each independently selected from a side chain of a naturally occurring $\alpha$-amino acid, H, alkyl, alkenyl, alkynyl, aryl, aralkyl, aralkenyl, aralkynyl, heteroaryl, heteroalkyl, heteroaralkenyl, $Z^1$-substituted aryl, aralkyl, aralkenyl or aralkynyl, and $Z^2$-substituted heteroaryl, heteroaralkyl or heteroaralkenyl;
   $Z^1$ is selected from halogen, lower alkyl, lower alkoxy, OH, haloalkyl, $NO_2$, nitrile, alkylthio, phenyl and —NR'R";

each of R' and R" is independently is H, alkyl, OH or halo lower alkyl;

$Z^2$ is lower alkyl or halo lower alkyl;

$R^{22}$, $R^{23}$ and $R^{24}$ are each independently H or alkyl; and $R^{30}$ and $R^{25}$ are each independently selected as in (a), (b) or (c) as follows:
  (a) $R^{30}$ is a peptide residue containing from 1 to 71 amino acid residues such that the compound contains at least two contiguous amino acids from the C-terminal portion of any one of SEQ ID Nos. 1 through 14 or other anaphylatoxin selected from C3a, C4a; and C5a, and $R^{25}$ is H or alkyl; or
  (b) $R^{30}$ and $R^{25}$ are each independently H, $C(O)R^{10}$, alkyl, alkenyl, alkynyl, aryl, heteroaryl, aralkyl, heteroaralkyl, $Si(R^{10})_3$, $S(O)_m R^{10}$ where m is 0–2 or $P(O)_n(R^{10})_p$ where n is 0–3; p is 1–2; $R^{10}$ is alkyl, aryl, heteroaryl, aralkyl, heteroaralkyl, alkoxy, aryloxy, heteroaryloxy, aralkoxy, heteroaralkoxy or $NR^{11}R^{12}$; and $R^{11}$ and $R^{12}$ are each independently selected from among H, alkyl, aryl, heteroaryl, aralkyl and heteroaralkyl; or
  (c) $R^{30}$ and $R^{25}$, together with the nitrogen atom to which they are attached, form a heterocyclyl, heteroaryl, cyclic amide or cyclic imide group; or
  (ii) $R^2$ and $R^{22}$, and/or $R^3$ and $R^{23}$, and/or $R^4$ and $R^{24}$, and/or $R^5$ and $R^{25}$ together form alkylene; and the remainder of $R^2$, $R^3$, $R^4$, $R^5$, $R^{22}$, $R^{23}$, $R^{24}$, $R^{25}$ and $R^{30}$ are selected as in (i);

Y is any group cleavable from the compound by MASP and comprises a radiolabelled, photochemical, colorimetric, chromogenic, fluorescent, fluorogenic, phosphorescent, electrochemical, chemiluminescent or bioluminescently-labelled tag; and $R^1$, $R^2$, $R^3$, $R^4$, $R^5$, $R^{25}$, $R^{30}$, X and Y are unsubstituted or are substituted with one or more substituents selection from Q, which, as defined herein, is halogen, hydroxy, nitrile, nitro, formyl, mercapto, carboxy, hydroxysulfonyl, hydroxyphosphoryl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl, or any two Q groups substituting adjacent atoms on an aryl or heteroaryl group may form 1,3-butadienylene, 1-aza-1,3-butadienylene or 2-aza-1,3-butadienylene;

with the proviso that the compound is not Ac-Tyr-Ile-Gly-Ser-Arg-pNA.

44. The compound of claim 39, wherein $R^5$, $R^{26}$ and $R^{30}$ are selected from (i), (ii) or (iii) as follows:
  (i) $R^5$ is the side chain of isoleucine, methionine, leucine, valine, alanine, glycine, serine or threonine; and $R^{25}$ and $R^{30}$ are selected as in (a), (b) or (c) as follows:
    (a) $R^{30}$ is a peptide containing from 1 to 71 amino acid residues such that the compound contains the C-terminal portion of any one of SEQ ID NOS. 1 through 14, and $R^{25}$ is H or alkyl; or
    (b) $R^{30}$ and $R^{25}$ are each independently H, $C(O)R^{10}$, alkyl, alkenyl, alkynyl, aryl, heteroaryl, aralkyl, heteroaralkyl, $Si(R^{10})_3$, $S(O)_m R^{10}$ where m is 0–2 or $P(O)_n(R^{10})_p$ where n is 0–3; p is 1–2; $R^{10}$ is alkyl, aryl, heteroaryl, aralkyl, heteroaralkyl, alkoxy, aryloxy, heteroaryloxy, aralkoxy, heteroaralkoxy or $NR^{11}R^{12}$; and $R^{11}$ and $R^{12}$ are each independently selected from among H, alkyl, aryl, heteroaryl, aralkyl and heteroaralkyl; or
    (c) $R^{30}$ and $R^{25}$, together with the nitrogen atom to which they are attached, form a heterocyclyl, heteroaryl, cyclic amide or cyclic imide group; or
  (ii) $R^5$ and $R^{25}$ together form alkylene; and $R^{30}$ is selected as in (i)(a) or (i)(b); or
  (iii) $R^5$ is alkyl, alkenyl or alkynyl; and $R^{25}$ and $R^{30}$ are selected as in (i).

45. The compound of claim 39, wherein:

the compound has formula (II):

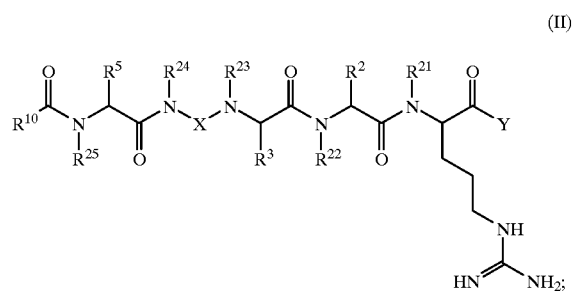

(II)

$R^{21}$ is H or alkyl;

X is alkylene, alkenylene or $CH(R^4)C(O)$;

$R^{10}$ is selected from (i) or (ii) as follows:
  (i) alkyl, aryl, heteroaryl, aralkyl, heteroaralkyl, alkoxy, aryloxy, heteroaryloxy, aralkoxy, heteroaralkoxy or $NR^{11}R^{12}$; or
  (ii) $R^{10}$ contains 1–5 amino acid residues or analogs thereof, with the N-terminus capped with $C(O)R^{70}$;

$R^{70}$ is alkyl, aryl, heteroaryl, aralkyl, heteroaralkyl, alkoxy, aryloxy, heteroaryloxy, aralkoxy, heteroaralkoxy or $NR^{11}R^{12}$;

$R^{11}$ and $R^{12}$ are each independently H, alkyl, aryl, heteroaryl, aralkyl or heteroaralkyl;

$R^2$, $R^3$, $R^4$, $R^5$, $R^{22}$, $R^{23}$, $R^{24}$ and $R^{25}$ are each independently selected as in (i) or (ii) as follows:
  (i) $R^2$, $R^3$, $R^4$ and $R^5$ are each independently selected from a side chain of a naturally occurring α-amino acid, H, alkyl, alkenyl, alkynyl, aryl, aralkyl, aralkenyl, aralkynyl, heteroaryl, heteroaralkyl, heteroaralkenyl, $Z^1$-substituted aryl, aralkyl, aralkenyl or aralkynyl, and $Z^2$-substituted heteroaryl, heteroaralkyl or heteroaralkenyl;

$Z^1$ is selected from halogen, lower alkyl, lower alkoxy, OH, haloalkyl, $NO_2$, nitrile, alkylthio, phenyl and —NR'R";

each of R' and R" is independently H, alkyl, OH or halo lower alkyl;

$Z^2$ is lower alkyl or halo lower alkyl;

$R^{22}$, $R^{23}$, $R^{24}$ and $R^{25}$ are each independently H or alkyl; or
  (ii) $R^2$ and $R^{22}$, and/or $R^3$ and $R^{23}$, and/or $R^4$ and $R^{24}$, and/or $R^5$ and $R^{25}$ together form alkylene; and the remainder of $R^2$, $R^3$, $R^4$, $R^5$, $R^{22}$, $R^{23}$, $R^{24}$ and $R^{25}$ are selected as in (i);

Y is a tag group capable of being assayed by radiolabelled, photochemical, colorimetric, chromogenic, fluorescent, fluorogenic, phosphorescent, electrochemical, chemiluminescent or bioluminescent assays; and $R^2$, $R^3$, $R^4$, $R^5$, X and Y are unsubstituted or are substituted with one or more substituents selection from Q, which, as defined herein, is halogen, hydroxy, nitrile, nitro, formyl, mercapto, carboxy, hydroxysulfonyl, hydroxyphosphoryl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl, or any two Q groups substituting adjacent atoms on an aryl or heteroaryl group may form 1,3-butadienylene, 1-aza-1,3-butadienylene or 2-aza-1,3-butadienylene.

46. The compound of claim 1 that has formula (III):

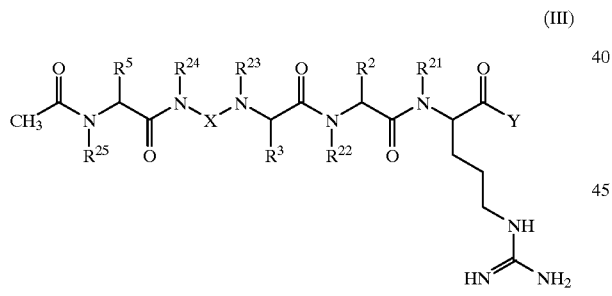

(III)

wherein:

$R^{21}$ is H or alkyl;

X is alkylene, alkenylene or $CH(R^4)C(O)$;

$R^2$, $R^3$, $R^4$, $R^5$, $R^{22}$, $R^{23}$, $R^{24}$ and $R^{25}$ are each independently selected as in (i) or (ii) as follows:

(i) $R^2$, $R^3$, $R^4$ and $R^5$ are each independently selected from a side chain of a naturally occurring α-amino acid, H, alkyl, alkenyl, alkynyl, aryl, aralkyl, aralkenyl, aralkynyl, heteroaryl, heteroalkyl, heteroaralkenyl, $Z^1$-substituted aryl, aralkyl, aralkenyl or aralkynyl, and $Z^2$-substituted heteroaryl, heteroaralkyl or heteroaralkenyl;

$Z^1$ is selected from halogen, lower alkyl, lower alkoxy, OH, haloalkyl, $NO_2$, nitrile, alkylthio, phenyl and —NR'R";

each of R' and R" is independently H, alkyl, OH or halo lower alkyl;

$Z^2$ is lower alkyl or halo lower alkyl;

$R^{22}$, $R^{23}$, $R^{24}$ and $R^{25}$ are each independently H or alkyl; or (ii) $R^2$ and $R^{22}$, and/or $R^3$ and $R^{23}$, and/or $R^4$ and $R^{24}$, and/or $R^5$ and $R^{25}$ together form alkylene; and the remainder of $R^2$, $R^3$, $R^4$, $R^5$, $R^{22}$, $R^{23}$, $R^{24}$ and $R^{25}$ are selected as in (i);

Y is a tag group capable of being assayed by radiolabelled, photochemical, colorimetric, chromogenic, fluorescent, fluorogenic, phosphorescent, electrochemical, chemiluminescent or bioluminescent assays; and $R^2$, $R^3$, $R^4$, $R^5$, X and Y are unsubstituted or are substituted with one or more substituents selection from Q, which, as defined herein, is halogen, hydroxy, nitrile, nitro, formyl, mercapto, carboxy, hydroxysulfonyl, hydroxyphosphoryl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl, or any two Q groups substituting adjacent atoms on an aryl or heteroaryl group may form 1,3-butadienylene, 1-aza-1,3-butadienylene or 2-aza-1,3-butadienylene.

47. The compound of claim 42, wherein $R^5$ and $R^{25}$ are selected from (i), (ii) or (iii) as follows:
(i) $R^5$ is the side chain of isoleucine, methionine, leucine, valine, alanine, glycine, serine or threonine; and $R^{25}$ is H or alkyl; or
(ii) $R^5$ and $R^{25}$ together form alkylene; or
(iii) $R^5$ is alkyl, alkenyl or alkynyl; and $R^{25}$ is selected as in (i).

48. The compound of claim 42, wherein $R^5$ and $R^{25}$ are selected from (i), (ii) or (iii) as follows:
(i) $R^5$ is the side chain of isoleucine, methionine, leucine, valine, alanine, glycine, serine or threonine; and $R^{25}$ is H or alkyl; or
(ii) $R^5$ and $R^{25}$ together form alkylene; or
(iii) $R^5$ is alkyl, alkenyl or alkynyl; and $R^{25}$ is selected as in (i).

49. The compound of claim 42, wherein $R^3$ is the side chain of leucine.

50. The compound of claim 39, wherein X is alkylene or $CH(R^4)C(O)$ where $R^4$ is H.

51. The compound of claim 42, wherein X is alkylene or $CH(R^4)C(O)$ where $R^4$ is H.

52. The compound of claim 39, wherein Y is $SR^{13}$, $OR^{13}$ or $NR^{13}R^{14}$, where $R^{13}$ is alkyl, aryl, heteroaryl, aralkyl and heteroaralkyl and $R^{14}$ is H, alkyl, aryl, heteroaryl, aralkyl and heteroaralkyl, wherein $HSR^{13}$, $HOR^{13}$ and $HNR^{13}R^{14}$ are capable of being quantitatively assayed by radiolabelled, photochemical, colorimetric, chromogenic, fluorescent, fluorogenic, phosphorescent, electrochemical, chemiluminescent or bioluminescent assays.

53. The compound of claim 1, wherein Y is selected from 4-methyl coumaryl-7-amino, 4-trifluoromethyl coumaryl-7-amino, dansyl, naphthylamino, 7-oxy-coumaryl, 5-amino isophthalic acid diethyl ester, dansyl, coumaryl-7-amino, 4-trifluoromethyl coumaryl-7-amino, 2-methylanthranilic acid, para-nitroanilino, para-nitrophenoxy, ortho-nitrophenoxy, ortho-carboxyphenoxy, nitrophenylamino, 1-carboxy-2-nitrophen-5-ylamino, 1-sulfo-2-nitrophen-5-ylamino, naphthylamino, $\mu$-naphthylamino, $\beta$-naphthylamino, nitronaphthylamino, 5-nitro-$\alpha$-naphthylamino, riboflavin methoxynaphthylamino, 4-methoxy-$\mu$-naphthylamino, quinonylamino, a luminol, isoluminol, a luciferin, quinon-5-ylamino, nitroquinonylamino, 8-nitroquinon-5-ylamino, 4-methylcoumaryl-7-amino, 4-trifluoromethylcoumaryl-7-amino, and naphthylamino tagged with radioactive halogen.

54. The compound of claim 39, wherein R and Y each comprise a detectable tag.

55. The compound of claim 50, wherein R is a fluoroscent tag and Y comprises a calorimetric, wherein the fluorescent of R is quenched until cleavage of Y.

56. The method of claim 51, wherein R comprises 2-methyl-anthranilic acid.

57. The method of claim 52, where Y comprises pNA.

58. The compound of claim 39, wherein:
   $R^1$ is the side chain of arginine or lysine;
   $R^2$ is the side chain of alanine, glycine, glutamine, asparagine, threonine or norleucine;
   $R^3$ is the side chain of leucine;
   $R^4$ is the side chain of glycine, histidine, glutamine or leucine; and
   $R^5$ is the side chain of alanine, leucine, isoleucine, methionine or valine.

59. The compound of claim 39 selected from the group consisting of R-Ala-Gly-Leu-Gln-Arg-Y, R-Ala-Gly-Leu-Asn-Arg-Y, R-Ala-Gly-Leu-Thr-Arg-Y, R-Ala-Gly-Leu-Nle-Arg-, R-Ala-Gly-Leu-Nle-Arg-Y, and R-Leu-Ala-Arg-Y.

60. The compound of claim 55 selected from the group consisting of Ac-Ala-Gly-Leu-Gln-Arg-pNA, Ac-Ala-Gly-Leu-Asn-Arg-pNA, Ac-Ala-Gly-Leu-Thr-Arg-pNA, Ac-Ala-Gly-Leu-Nle-Arg-pNA, Ac-Ala-Gly-Leu-Nle-Arg-pNA, and Ac-Leu-Ala-Arg-pNA.

61. The compound of claim 55, wherein Y is selected from the group consisting of 4-methylcoumaryl-7-amino, 4-trifluoromethylcoumaryl-7-amino, naphthylamino, 7-oxycoumaryl, 5-amino-iso-phthalic acid di(methyl or ethyl) ester, para-nitroanilino, para-nitrophenoxy, ortho-nitrophenoxy, ortho-carboxyphenoxy, nitrophenylamino, 1-carboxy-2-nitrophen-5-ylamino, 1 -sulfo-2-nitrophen-5-ylamino, p-naphthylamino, $\beta$-naphthylamino, nitronaphthylamino, 5-nitro-$\alpha$-naphthylamino, methoxynaphthylamino, 4-methoxy-$\mu$-naphthylamino, quinonylamino, quinon-5-ylamino, nitroquinonylamino and 8-nitroquinon-5-ylamino.

62. A kit, comprising:
   (a) a first reagent, comprising a compound of claim 39; and
   (b) a second reagent comprising an agent that inhibits the activity of a mannan-binding protein-associated serine protease (MASP).

63. The kit of claim 58, wherein the compound is on a solid support.

64. The method of claim 59, wherein the solid support is a microtiter plate.

65. A method of detecting or monitoring a condition in a mammal in which complement activation is effected by exposure to neutral sugars, comprising:
   obtaining a sample of plasma from the mammal, wherein the plasma comprises ethylenediaminetetraacetic acid (EDTA);
   measuring the level of in vivo levels of activated MASP by the method of claim 1,
   wherein the level activated MASP reflects the severity of the condition.

66. A method of assessing the efficacy of therapeutic treatments for infectious agents, organ transplant rejection, tissue injury, autoimmune diseases and inflammatory responses in which C activation is mediated or initiated by exposure of neutral sugars, comprising:
   obtaining a first sample of EDTA plasma from a subject prior to commencing treatment or after commencing treatment;
   determining mannan-binding protein-associated serine protease (MASP) activity in the first sample by the method of claim 1;
   obtaining a second sample of EDTA plasma from the subject after commencing treatment and at a time subsequent to the first sample;
   determining MASP activity in the second sample, and comparing the activity of MASP in the samples, wherein a reduction in MASP activity reflects the efficacy of the selected treatment.

67. A method of assessing the toxicity or injury of therapeutic treatments, comprising:
   obtaining a first sample of EDTA plasma from a subject prior to commencing treatment or after commencing treatment;
   determining mannan-binding protein-associated serine protease (MASP) activity in the first sample by the method of claim 1;
   obtaining a second sample of EDTA plasma from the subject after commencing treatment and at a time subsequent to the first sample;
   determining MASP activity in the second sample, and comparing the activity of MASP in the samples, wherein an increase in MASP activity reflects the toxicity of the treatment or injury from the treatment.

68. A method of screening test compounds as agents for treatments of viral diseases, parasitic infectious, tissue injury, organ transplant rejection, autoimmune diseases or inflammatory responses, comprising:
   obtaining a first sample of EDTA plasma from a test animal model for a selected condition or disorder prior to administering the test compound;
   determining mannan-binding protein-associated serine protease (MASP) activity in the first sample by the method of claim 1;
   administering the test compounds;
   obtaining a second sample of EDTA plasma;
   determining MASP activity in the second sample, and comparing the activity of MASP in the samples, wherein a decrease in MASP activity is indicative of activity of the test compound for the selected condition or disorder.

* * * * *

UNITED STATES PATENT AND TRADEMARK OFFICE
CERTIFICATE OF CORRECTION

PATENT NO. : 6,235,494 B1
DATED : May 22, 2001
INVENTOR(S) : Hugli

It is certified that error appears in the above-identified patent and that said Letters Patent is hereby corrected as shown below:

Column 1,
Line 50, please replace "The" with -- the --

Column 2,
Line 34, please replace "c1" with -- C1 --
Line 47, please replace "amplifier" with -- amplified --
Line 52, please replace "of" with -- pathway of --

Column 3,
Line 39, please replace "pathway is" with -- pathway --

Column 6,
Lines 10-11, please replace "attorney docket no. 24730-2203B" with -- 09/245,829 --

Column 7,
Line 7, please replace "which is" with -- which --
Line 63, please replace "via n" with -- via an --
Line 65, please replace "Blocking group" with -- (Blocking group) --

Column 8,
Line 5, please replace "can" with -- can be --
Line 14, please replace "bond" with -- bond, --
Line 62, please replace "substrate" with -- substrates --

Column 9,
Line 28, please replace "Arg " with -- Arg-pNA --
Line 32, please replace "fluoroescence" with -- fluorescence --

Column 11,
Line 4, please replace "selection" with -- selected --
Line 45, please replace "herein," with -- herein, and --
Line 51, please replace "trypsin or" with -- trypsin --

UNITED STATES PATENT AND TRADEMARK OFFICE
CERTIFICATE OF CORRECTION

PATENT NO. : 6,235,494 B1
DATED : May 22, 2001
INVENTOR(S) : Hugli

It is certified that error appears in the above-identified patent and that said Letters Patent is hereby corrected as shown below:

Column 12,
Line 58, please replace "participates" with -- participates in --
Line 60, please replace "Disease" with -- disease --
Line 63, please replace "rejections" with -- rejection --

Column 13,
Line 6, please replace "IL6" with -- IL-6 --
Lines 20-21, please replace "(PMNs). Polymorphonuclear" with
-- (PMNs) and polymorphonuclear --
Line 21, please replace "granulocytes (PMN)" 'with
-- (PMN) granulocytes --
Line 34, please replace "examples" with -- example --

Column 16,
Line 18, please replace "In" with -- in --

Column 20,
Line 2, please replace "and" with -- an --

Column 22,
Line 67, please delete the word "the"

Column 23,
Line 1, please replace "continuation-in-part, filed Feb. 5,
1999) were those" with -- Ser. No. 09/245,829) --
Line 11, please replace "must" with -- must be --
Line 38, please replace "Pathways" with -- pathways --
Line 62, please replace "samples" with -- samples are --
Line 64, please replace "specificity," with -- specificity; --

Column 24,
Line 7, please replace "Masp" with -- MASP --
Line 42, please replace "Simga" with -- Sigma --
Line 62, please replace "in" with -- are --

UNITED STATES PATENT AND TRADEMARK OFFICE
CERTIFICATE OF CORRECTION

PATENT NO. : 6,235,494 B1
DATED : May 22, 2001
INVENTOR(S) : Hugli

It is certified that error appears in the above-identified patent and that said Letters Patent is hereby corrected as shown below:

Column 25,
Line 16, please replace "compounds" with -- compounds, and --
Line 20, please replace "a" with -- as --
Line 21, please replace "Blocking group" with -- (Blocking group) --
Line 39, please replace "ntiranilide" with -- nitroaniline --
Line 39, please delete the word "that"
Line 60, please replace "3" with -- C --

Column 27,
Lines 26-27, please replace "is detectable tag group that is detectable labeled from a member" with -- is a detectable tag group that is or contains a label --
Line 29, please replace "fluorescent a" with -- fluorescent --
Line 30, please replace "chemiluminescent" with -- a chemiluminescent --
Line 32, please replace "therefor" with -- thereof --
Line 35, please replace "selection" with -- selected --

Column 28,
Line 50, please replace "(III)" with -- (II) --

Column 29,
Line 45, please replace "selection" with -- selected --

Column 30,
Line 60, please replace "a-amino" with -- *a*-amino --

Column 31,
Line 21, please replace "selection" with -- selected --

Column 33,
Line 51, please replace "1251 or 1311" with -- $^{125}$I or $^{131}$I --
Line 56, please replace "$^3$H]" with -- $^3$H --

Column 39,
Line 6, please replace "the with" with -- the --
Line 17, please replace "assess" with -- assessed --
Line 18, please replace "therefor" with -- thereof --
Line 32, please replace "only" with -- only in --
Line 42, please replace "include" with -- including --
Line 59, please replace "proteinases" with -- proteinases, --
Line 65, please replace *"Biophysl"* with -- *Biophys* --

UNITED STATES PATENT AND TRADEMARK OFFICE
CERTIFICATE OF CORRECTION

PATENT NO. : 6,235,494 B1
DATED : May 22, 2001
INVENTOR(S) : Hugli

It is certified that error appears in the above-identified patent and that said Letters Patent is hereby corrected as shown below:

Column 40,
Line 37, please replace "example is" with
-- examples are --

Column 41,
Line 2, please replace "background" with -- (background --
Line 4, please replace "Cost&" with -- Costar --
Line 27, please replace "mixture. The" with -- mixture, the --
Line 59, please replace "calcium" with -- unless calcium --

Column 42,
Line 2, please delete the phrase "Mechanism for MASP
activation in tissue injury."
Line 23, please replace "substrate:." with -- substrate --

Please delete claim 6 and replace it with the following claim:
-- 6. The method of claim 1, wherein Y is any group cleavable from the compound by MASP and comprises a radiolabelled, photochemical, colorimetric, chromogenic, fluorescent, fluorogenic, phosphorescent, electrochemical, chemiluminescent or bioluminescently-labelled tag or, where R comprises a tag, Y is an amino acid residue such that upon cleavage, the tag on R is detectable. --

Please delete claim 7 and replace it with the following claim:
-- 7. The method of claim 1, wherein the compound [of] has formula (I):

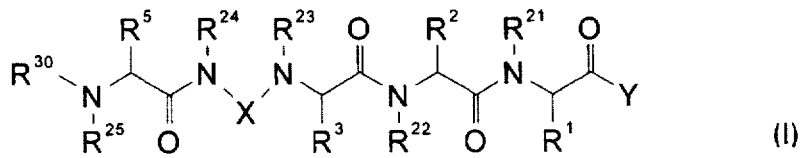

(I)

or analogs thereof:, wherein:
    R is $R^{30}$;
    $R^1$ is $R^{60}$-A, where A is $NH_t(R^{40})_{3-t}$, heterocyclyl, heteroaryl, guanidinyl, amidino or imino, and is capable of forming a cationic salt at physiological pH, or is $N^+(R^{40})_4$;

UNITED STATES PATENT AND TRADEMARK OFFICE
CERTIFICATE OF CORRECTION

PATENT NO. : 6,235,494 B1
DATED : May 22, 2001
INVENTOR(S) : Hugli

It is certified that error appears in the above-identified patent and that said Letters Patent is hereby corrected as shown below:

$R^{60}$ is alkylene, alkenylene, alkynylene, cycloalkylene, heterocyclylene, aralkylene, heteroaralkylene, arylene or heteroarylene;

$R^{40}$ is alkyl, alkenyl, alkynyl, aryl or heteroaryl;

t is 0-3;

$R^{21}$ is H or alkyl;

X is alkylene, alkenylene or $CH(R^4)C(O)$;

$R^2$, $R^3$, $R^4$, $R^5$, $R^{22}$, $R^{23}$, $R^{24}$, $R^{25}$ and $R^{30}$ are each independently selected as in (i) or (ii) as follows:

(i) $R^2$, $R^3$, $R^4$ and $R^5$ are each independently selected from a side chain of a naturally occurring $a$-amino acid, H, alkyl, alkenyl, alkynyl, aryl, aralkyl, aralkenyl, aralkynyl, heteroaryl, heteroaralkyl, heteroaralkenyl, $Z^1$-substituted aryl, aralkyl, aralkenyl or aralkynyl, and $Z^2$-substituted heteroaryl, heteroaralkyl or heteroaralkenyl;

$Z^1$ is selected from halogen, lower alkyl, lower alkoxy, OH, haloalkyl, $NO_2$, nitrile, alkylthio, phenyl and -NR'R";

each of R'R" is independently H, alkyl, OH or halo lower alkyl;

$Z^2$ is lower alkyl or halo lower alkyl;

$R^{22}$, $R^{23}$ and $R^{24}$ are each independently H or alkyl; and $R^{30}$ and $R^{25}$ are each independently selected as in (a), (b) or (c) as follows:

(a) $R^{30}$ is a peptide residue containing from 1 or more amino acid residues such that the compound contains at least two contiguous amino acids from the C-terminal portion of any one of SEQ ID NOS. 1 through 14 or other anaphylatoxin selected from C3a, C4a, and C5a, and the resulting peptide is cleaved by a MASP; and $R^{25}$ is H or alkyl; or (b) $R^{30}$ and $R^{25}$ are each independently H, $C(O)R^{10}$, alkyl, alkenyl, alkynyl, aryl, heteroaryl, aralkyl, heteroaralkyl, $Si(R^{10})_3$, $S(O)_m R^{10}$ where m is 0-2 or $P(O)_n(R^{10})_p$ where n is 0-3; p is 1-2; $R^{10}$ is alkyl, aryl, heteroaryl, aralkyl, heteroaralkyl, alkoxy, aryloxy, heteroaryloxy, aralkoxy, heteroaralkoxy or $NR^{11}R^{12}$; and $R^{11}$ and $R^{12}$ are each independently selected from among H, alkyl, aryl, heteroaryl, aralkyl and heteroaralkyl; or (c) $R^{30}$ and $R^{25}$, together with the nitrogen atom to which they are attached, form a heterocyclyl, heteroaryl, cyclic amide or cyclic imide group; or (ii) $R^2$ and $R^{22}$, and/or $R^3$ and $R^{23}$, and/or $R^4$ and $R^{24}$, and/or $R^5$ and $R^{25}$ together form alkylene; and the remainder of $R^2$, $R^3$, $R^4$, $R^5$, $R^{22}$, $R^{23}$, $R^{24}$, $R^{25}$ and $R^{30}$ are selected as in (i);

UNITED STATES PATENT AND TRADEMARK OFFICE
CERTIFICATE OF CORRECTION

PATENT NO. : 6,235,494 B1
DATED : May 22, 2001
INVENTOR(S) : Hugli

It is certified that error appears in the above-identified patent and that said Letters Patent is hereby corrected as shown below:

Y is any group cleavable from the compound by MASP and comprises a radiolabelled, photochemical, colorimetric, chromogenic, fluorescent, fluorogenic, phosphorescent, electrochemical, chemiluminescent or bioluminescently-labelled tag or, where R comprises a tag, Y is an amino acid residue such that upon cleavage of Y, the tag on R is detectable; and $R^1$, $R^2$, $R^3$, $R^4$, $R^5$, $R^{25}$, $R^{30}$, X and Y are unsubstituted or are substituted with one or more substituents selected from Q, which, as defined herein, is halogen, hydroxy, nitrile, nitro, formyl, mercapto, carboxy, hydroxysulfonyl, hydroxyphosphoryl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkyl-aminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl, or any two Q groups substituting adjacent atoms on an aryl or heteroaryl group may form 1,3-butadienylene, 1-aza-1,3-butadienylene or 2-aza-1,3-butadienylene. --

Please delete claim 13 and replace it with the following claim:
--13. The method of claim 1, wherein:
the compound has formula (II):

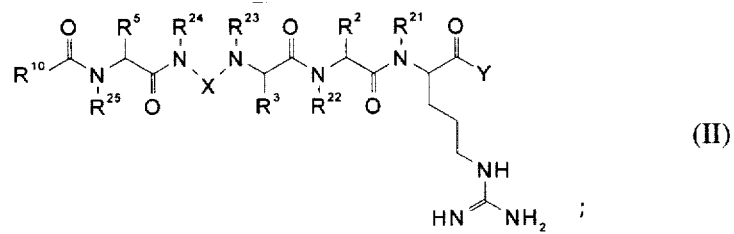

(II)

wherein

UNITED STATES PATENT AND TRADEMARK OFFICE
CERTIFICATE OF CORRECTION

PATENT NO. : 6,235,494 B1
DATED : May 22, 2001
INVENTOR(S) : Hugli

It is certified that error appears in the above-identified patent and that said Letters Patent is hereby corrected as shown below:

$R$ is $R^{30}$;

$R^{21}$ is H or alkyl; X is alkylene, alkenylene or $CH(R^4)C(O)$;

$R^{10}$ is selected from (i) or (ii) as follows:
   (i) alkyl, aryl, heteroaryl, aralkyl, heteroaralkyl, alkoxy, aryloxy, heteroaryloxy, aralkoxy, heteroaralkoxy or $NR^{11}R^{12}$; or
   (ii) $R^{10}$ contains 1-5 amino acid residues or analogs thereof, with the N-terminus capped with $C(O)R^{70}$;

$R^{70}$ is alkyl, aryl, heteroaryl, aralkyl, heteroaralkyl, alkoxy, aryloxy, heteroaryloxy, aralkoxy, heteroaralkoxy or $NR^{11}R^{12}$ $R^{11}$ and $R^{12}$ are each independently H, alkyl, aryl, heteroaryl, aralkyl or heteroaralkyl;

$R^2, R^3, R^4, R^5, R^{22}, R^{23}, R^{24}$ and $R^{25}$ are each independently selected as in (i) or (ii) as follows:
   (i) $R^2, R^3, R^4$ and $R^5$ are each independently selected from a side chain of a naturally occurring α-amino acid, H, alkyl, alkenyl, alkynyl, aryl, aralkyl, aralkenyl, aralkynyl, heteroaryl, heteroaralkyl, heteroaralkenyl, $Z^1$-substituted aryl, aralkyl, aralkenyl or aralkynyl, and $Z^2$- substituted heteroaryl, heteroaralkyl or heteroaralkenyl;

$Z^1$ is selected from halogen, lower alkyl, lower alkoxy, OH, haloalkyl, $NO_2$, nitrile, alkylthio, phenyl and -NR'R";
   each of R' and R" is independently H, alkyl, OH or halo lower alkyl;

$Z^2$ is lower alkyl or halo lower alkyl;

$R^{22}, R^{23}, R^{24}$ and $R^{25}$ are each independently H or alkyl; or
   (ii) $R^2$ and $R^{22}$, and/or $R^3$ and $R^{23}$, and/or $R^4$ and $R^{24}$, and/or $R^5$ and $R^{25}$ together form alkylene; and the remainder of $R^2, R^3, R^4, R^5, R^{22}, R^{23}, R^{24}$ and $R^{25}$ are selected as in (i);

Y is a tag group capable of being assayed by radiolabelled, photochemical, colorimetric, chromogenic, fluorescent, fluorogenic, phosphorescent, electrochemical, chemiluminescent or bioluminescent assays; and

UNITED STATES PATENT AND TRADEMARK OFFICE
CERTIFICATE OF CORRECTION

PATENT NO. : 6,235,494 B1
DATED : May 22, 2001
INVENTOR(S) : Hugli

It is certified that error appears in the above-identified patent and that said Letters Patent is hereby corrected as shown below:

$R^2$, $R^3$, $R^4$, $R^5$, X and Y are unsubstituted or are substituted with one or more substituents selected from Q, which, as defined herein, is halogen, hydroxy, nitrile, nitro, formyl, mercapto, carboxy, hydroxysulfonyl, hydroxyphosphoryl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl, or any two Q groups substituting adjacent atoms on an aryl or heteroaryl group may form 1,3-butadienylene, 1-aza-1,3-butadienylene or 2-aza-1,3-butadienylene. --

Please delete claim 16 and replace it with the following claim:
-- 16. The method of claim 1 wherein: the compound has formula (III):

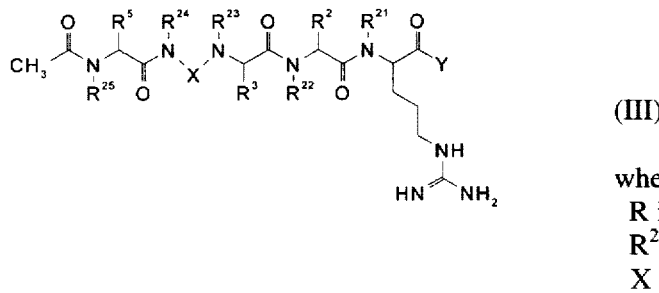

(III)

wherein:
R is $R^{30}$;
$R^{21}$ is H or alkyl;
X is alkylene, alkenylene or

UNITED STATES PATENT AND TRADEMARK OFFICE
CERTIFICATE OF CORRECTION

PATENT NO. : 6,235,494 B1
DATED : May 22, 2001
INVENTOR(S) : Hugli

It is certified that error appears in the above-identified patent and that said Letters Patent is hereby corrected as shown below:

$CH(R^4)C(O)$;

$R^2$, $R^3$, $R^4$, $R^5$, $R^{22}$, $R^{23}$, $R^{24}$ and $R^{25}$ are each independently selected as in (i) or (ii) as follows:

(i) $R^2$, $R^3$, $R^4$ and $R^5$ are each independently selected from a side chain of a naturally occurring α-amino acid, H, alkyl, alkenyl, alkynyl, aryl, aralkyl, aralkenyl, aralkynyl, heteroaryl, heteroaralkyl, heteroaralkenyl, $Z^1$-substituted aryl, aralkyl, aralkenyl or aralkynyl, and $Z^2$- substituted heteroaryl, heteroaralkyl or heteroaralkenyl;

$Z^1$ is selected from halogen, lower alkyl, lower alkoxy, OH, haloalkyl, $NO_2$, nitrile, alkylthio, phenyl and -NR'R";

each of R' and R" is independently H, alkyl, OH or halo lower alkyl;

$Z^2$ is lower alkyl or halo lower alkyl;

$R^{22}$, $R^{23}$, $R^{24}$ and $R^{25}$ are each independently H or alkyl; or (ii) $R^2$ and $R^{22}$, and/or $R^3$ and $R^{23}$, and/or $R^4$ and $R^{24}$, and/or $R^5$ and $R^{25}$ together form alkylene; and the remainder of $R^2$, $R^3$, $R^4$, $R^5$, $R^{22}$, $R^{23}$, $R^{24}$ and $R^{25}$ are selected as in (i);

Y is a tag group capable of being assayed by radiolabelled, photochemical, colorimetric, chromogenic, fluorescent, fluorogenic, phosphorescent, electrochemical, chemiluminescent or bioluminescent assays; and $R^2$, $R^3$, $R^4$, $R^5$, X and Y are unsubstituted or are substituted with one or more substituents selected from Q, which, as defined herein, is halogen, hydroxy, nitrile, nitro, formyl, mercapto, carboxy, hydroxysulfonyl, hydroxyphosphoryl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylamino-carbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diaryl-aminoalkyl, alkylamino, dialkylamino, arylamino, diarylamino, alkylarylamino, alkylcarbonylamino, alkoxycarbonylamino, arylcarbonylamino, aryloxycarbonyl-amino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylamino-sulfonyl, dialkylaminosulfonyl, arylaminosulfonyl or diarylaminosulfonyl, or any two Q groups substituting adjacent atoms on an aryl or heteroaryl group may form 1,3-butadienylene, 1-aza-1,3-butadienylene or 2-aza-1,3-butadienylene. --

UNITED STATES PATENT AND TRADEMARK OFFICE
CERTIFICATE OF CORRECTION

PATENT NO.   : 6,235,494 B1
DATED        : May 22, 2001
INVENTOR(S)  : Hugli

It is certified that error appears in the above-identified patent and that said Letters Patent is hereby corrected as shown below:

Please delete claim 28 and replace it with the following claim:
-- 28. The method of claim 1, wherein Y is selected from 4-methyl coumaryl-7-amino, 4-trifluoromethyl coumaryl-7-amino, dansyl, naphthylamino, 7-oxy-coumaryl, 5-amino isophthalic acid diethyl ester, coumaryl-7-amino, 2-methyl-anthranilic acid, para-nitroanilino, para-nitrophenoxy, ortho-nitrophenoxy, ortho carboxyphenoxy, nitrophenylamino, 1-carboxy-2-nitrophen-5-ylamino, 1-sulfo-2 nitrophen-5-ylamino, naphthylamino, $\mu$-naphthylamino, $\beta$-naphthylamino, nitronaphthylamino, 5-nitro-$a$-naphthylamino, riboflavin methoxynaphthylamino, 4-methoxy-$\mu$-naphthylamino, quinonylamino, a luminol, isoluminol, a luciferin, quinon-5-ylamino, nitroquinonylamino, 8-nitroquinon-5-ylamino, and naphthylamino tagged with radioactive halogen. --

Please delete claim 31 and replace it with the following claim:
-- 31. The method of claim 29, wherein R is a fluorescent tag and Y comprises a colorimetric tag, wherein the fluorescence of R is quenched until cleavage of Y. --

Please delete claim 43 and replace it with the following claim:
-- 43. A compound of formula (I):

or analogs thereof; wherein:

$R^1$ is $R^{60}$-A, where A is $NH_t(R^{40})_{3-t}$, heterocyclyl, heteroaryl, guanidinyl, amidino or imino, and is capable of forming a cationic salt at physiological pH, or is $N^+(R^{40})_4$;
$R^{60}$ is alkylene, alkenylene, alkynylene, cycloalkylene, heterocyclylene, aralkylene, heteroaralkylene, arylene or heteroarylene;  $R^{40}$ is alkyl, alkenyl, alkynyl, aryl or heteroaryl;
t is 0-3;
$R^{21}$ is H or alkyl;
X is alkylene, alkenylene or $CH(R^4)C(O)$;

UNITED STATES PATENT AND TRADEMARK OFFICE
CERTIFICATE OF CORRECTION

PATENT NO. : 6,235,494 B1
DATED : May 22, 2001
INVENTOR(S) : Hugli

It is certified that error appears in the above-identified patent and that said Letters Patent is hereby corrected as shown below:

$R^2$, $R^3$, $R^4$, $R^5$, $R^{22}$, $R^{23}$, $R^{24}$, $R^{25}$ and $R^{30}$ are each independently selected as in (i) or (ii) as follows:

(i) $R^2$, $R^3$, $R^4$ and $R^5$ are each independently selected from a side chain of a naturally occurring α-amino acid, H, alkyl, alkenyl, alkynyl, aryl, aralkyl, aralkenyl, aralkynyl, heteroaryl, heteroaralkyl, heteroaralkenyl, $Z^1$-substituted aryl, aralkyl, aralkenyl or aralkynyl, and $Z^2$-substituted heteroaryl, heteroaralkyl or heteroaralkenyl;

$Z^1$ is selected from halogen, lower alkyl, lower alkoxy, OH, haloalkyl, $NO_2$, nitrile, alkylthio, phenyl and -NR′R″;

each of R′ and R″ is independently is H, alkyl, OH or halo lower alkyl;

$Z^2$ is lower alkyl or halo lower alkyl;

$R^{22}$, $R^{23}$ and $R^{24}$ are each independently H or alkyl; and $R^{30}$ and $R^{25}$ are each independently selected as in (a), (b) or (c) as follows:

(a) $R^{30}$ is a peptide residue containing from 1 to 71 amino acid residues such that the compound contains at least two contiguous aminoacids from the C-terminal portion of any one of SEQ ID Nos. 1 through 14 or other anaphylatoxin selected from C3a, C4a; and C5a, and $R^{25}$ is H or alkyl; or (b) $R^{30}$ and $R^{25}$ are each independently H, $C(O)R^{10}$, alkyl, alkenyl, alkynyl, aryl, heteroaryl, aralkyl, heteroaralkyl, $Si(R^{10})3$, $S(O)_m R^{10}$ where m is 0-2 or $P(O)_n(R^{10})_p$ where n is 0-3; p is 1-2; $R^{10}$ is alkyl, aryl, heteroaryl, aralkyl, heteroaralkyl, alkoxy, aryloxy, heteroaryloxy, aralkoxy, heteroaralkoxy or $NR^{11}R^{12}$; and $R^{11}$ and $R^{12}$ are each independently selected from among H, alkyl, aryl, heteroaryl, aralkyl and heteroaralkyl; or (c) $R^{30}$ and $R^{25}$, together with the nitrogen atom to which they are attached, form a heterocyclyl, heteroaryl, cyclic amide or cyclic imide group; or (ii) $R^2$ and $R^{22}$, and/or $R^3$ and $R^{23}$, and/or $R^4$ and $R^{24}$, and/or $R^5$ and $R^{25}$ together form alkylene; and the remainder of $R^2$, $R^3$, $R^4$, $R^5$, $R^{22}$, $R^{23}$, $R^{24}$, $R^{25}$ and $R^{30}$ are selected as in (i);

Y is any group cleavable from the compound by MASP and comprises a radiolabelled, photochemical, colorimetric, chromogenic, fluorescent, fluorogenic, phosphorescent, electrochemical, chemiluminescent or bioluminescently-labelled tag; and $R^1$, $R^2$, $R^3$, $R^4$, $R^5$, $R^{25}$, $R^{30}$, X and Y are unsubstituted or are substituted with one or more substituents selected from Q, which, as defined herein, is halogen, hydroxy, nitrile, nitro, formyl, mercapto, carboxy, hydroxysulfonyl, hydroxyphosphoryl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene,

UNITED STATES PATENT AND TRADEMARK OFFICE
CERTIFICATE OF CORRECTION

PATENT NO. : 6,235,494 B1
DATED : May 22, 2001
INVENTOR(S) : Hugli

It is certified that error appears in the above-identified patent and that said Letters Patent is hereby corrected as shown below:

arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl, or any two Q groups substituting adjacent atoms on an aryl or heteroaryl group may form 1,3-butadienylene, 1-aza-1,3-butadienylene or 2-aza-1,3-butadienylene;

with the proviso that the compound is not Ac-Tyr-Ile-Gly-Ser-Arg-pNA. --

Please delete claim 44 and replace it with the following claim:
-- 44. The compound of claim 43, wherein $R^5$, $R^{25}$ and $R^{30}$ are selected from (i), (ii) or (iii) as follows:

(i) $R^5$ is the side chain of isoleucine, methionine, leucine, valine, alanine, glycine, serine or threonine; and $R^{25}$ and $R^{30}$ are selected as in (a), (b) or (c) as follows: (a) $R^{30}$ is a peptide containing from 1 to 71 amino acid residues such that the compound contains the C-terminal portion of any one of SEQ ID NOS. 1 through 14, and $R^{25}$ is H or alkyl; or (b) $R^{30}$ and $R^{25}$ are each independently H, $C(O)R^{10}$, alkyl, alkenyl, alkynyl, aryl, heteroaryl, aralkyl, heteroaralkyl, $Si(R^{10})_3$, $S(O)_m R^{10}$ where m is 0-2 or $P(O)_n(R^{10})_p$ where n is 0-3; p is 1-2; $R^{10}$ is alkyl, aryl, heteroaryl, aralkyl, heteroaralkyl, alkoxy, aryloxy, heteroaryloxy, aralkoxy, heteroaralkoxy or $NR^{11}R^{12}$; and $R^{11}$ and $R^{12}$ are each independently selected from among H, alkyl, aryl, heteroaryl, aralkyl and heteroaralkyl; or (c) $R^{30}$ and $R^{25}$, together with the nitrogen atom to which they are attached, form a heterocyclyl, heteroaryl, cyclic amide or cyclic imide group; or (ii) $R^5$ and $R^{25}$ together form alkylene; and $R^{30}$ is selected as in (i) (a) or (i) (b); or (iii) $R^5$ is alkyl, alkenyl or alkynyl; and $R^{25}$ and $R^{30}$ are selected as in (i). --

UNITED STATES PATENT AND TRADEMARK OFFICE
CERTIFICATE OF CORRECTION

PATENT NO. : 6,235,494 B1
DATED : May 22, 2001
INVENTOR(S) : Hugli

It is certified that error appears in the above-identified patent and that said Letters Patent is hereby corrected as shown below:

Please delete claim 45 and replace it with the following claim:
-- 45. The compound of claim 43, wherein the compound has formula (II):

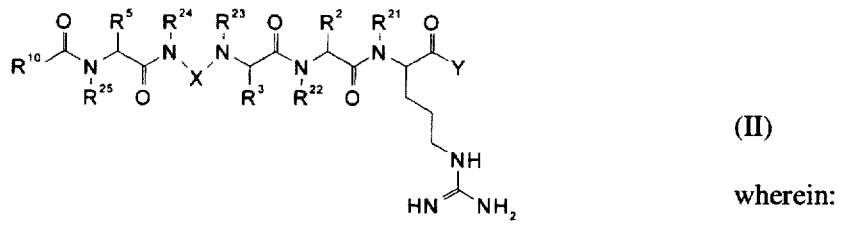

(II)

wherein:

$R^{21}$ is H or alkyl;

X is alkylene, alkenylene or $CH(R^4)C(0)$;
$R^{10}$ is selected from (i) or (ii) as follows:
    (i)     alkyl, aryl, heteroaryl, aralkyl, heteroaralkyl, alkoxy, aryloxy, heteroaryloxy, aralkoxy, heteroaralkoxy or $NR^{11}R^{12}$; or
    (ii)     $R^{10}$ contains 1-5 amino acid residues or analogs thereof, with the N-terminus capped with $C(O)R^{70}$;
$R^{70}$ is alkyl, aryl, heteroaryl, aralkyl, heteroaralkyl, alkoxy, aryloxy, heteroaryloxy, aralkoxy, heteroaralkoxy or $NR^{11}R^{12}$;
$R^{11}$ and $R^{12}$ are each independently H, alkyl, aryl, heteroaryl, aralkyl or heteroaralkyl;
$R^2$, $R^3$, $R^4$, $R^5$, $R^{22}$, $R^{23}$, $R^{24}$ and $R^{25}$ are each independently selected as in (i) or (ii) as follows:
    (i)     $R^2$, $R^3$, $R^4$ and $R^5$ are each independently selected from a side chain of a naturally occurring a-amino acid, H, alkyl, alkenyl, alkynyl, aryl, aralkyl, aralkenyl, aralkynyl, heteroaryl, heteroaralkyl, heteroaralkenyl, $Z^1$-substituted aryl, aralkyl, aralkenyl or aralkynyl, and $Z^2$-substituted heteroaryl, heteroaralkyl or heteroaralkenyl;
$Z^1$ is selected from halogen, lower alkyl, lower alkoxy, OH, haloalkyl, $NO_2$, nitrile, alkylthio, phenyl and -NR'R";
each of R' and R" is independently H, alkyl, OH or halo lower alkyl;
$Z^2$ is lower alkyl or halo lower alkyl;
$R^{22}$, $R^{23}$, $R^{24}$ and $R^{25}$ are each independently H or alkyl; or
    (ii)     $R^2$ and $R^{22}$, and/or $R^3$ and $R^{23}$, and/or $R^4$ and $R^{24}$, and/or $R^5$ and $R^{25}$ together form alkylene; and the remainder of $R^2$, $R^3$, $R^4$, $R^5$, $R^{22}$, $R^{23}$, $R^{24}$ and $R^{25}$ are selected as in (i);

UNITED STATES PATENT AND TRADEMARK OFFICE
CERTIFICATE OF CORRECTION

PATENT NO. : 6,235,494 B1
DATED : May 22, 2001
INVENTOR(S) : Hugli

It is certified that error appears in the above-identified patent and that said Letters Patent is hereby corrected as shown below:

Y is a tag group capable of being assayed by radiolabelled, photochemical, colorimetric, chromogenic, fluorescent, fluorogenic, phosphorescent, electrochemical, chemiluminescent or bioluminescent assays; and $R^2$, $R^3$, $R^4$, $R^5$, X and Y are unsubstituted or are substituted with one or more substituents selected from Q, which, as defined herein, is halogen, hydroxy, nitrile, nitro, formyl, mercapto, carboxy, hydroxysulfonyl, hydroxyphosphoryl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano,alkylsulfinyl, alkylsulfonyl, arylsulfinyl, arylsulfonyl, aminosulfonyl, alkyl-aminosulfonyl, dialkylaminosulfonyl, arylaminosulfonyl or diarylaminosulfonyl, or any two Q groups substituting adjacent atoms on an aryl or heteroaryl group may form 1,3-butadienylene, 1-aza-1,3-butadienylene or 2-aza-1,3-butadienylene. --

Please delete claim 46 and replace it with the following claim:
-- 46. The compound of claim 1 that has formula (III):

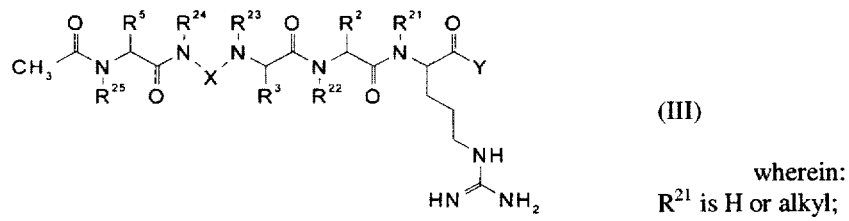

(III)

wherein:
$R^{21}$ is H or alkyl;

UNITED STATES PATENT AND TRADEMARK OFFICE
CERTIFICATE OF CORRECTION

PATENT NO. : 6,235,494 B1
DATED : May 22, 2001
INVENTOR(S) : Hugli

It is certified that error appears in the above-identified patent and that said Letters Patent is hereby corrected as shown below:

X is alkylene, alkenylene or $CH(R^4)C(O)$;
$R^2$, $R^3$, $R^4$, $R^5$, $R^{22}$, $R^{23}$, $R^{24}$ and $R^{25}$ are each independently selected as in (i) or (ii) as follows:
(i) $R^2$, $R^3$, $R^4$ and $R^5$ are each independently selected from a side chain of a naturally occurring α-amino acid, H, alkyl, alkenyl, alkynyl, aryl, aralkyl, aralkenyl, aralkynyl, heteroaryl, heteroaralkyl, heteroaralkenyl, $Z^1$-substituted aryl, aralkyl, aralkenyl or aralkynyl, and $Z^2$-substituted heteroaryl, heteroaralkyl or heteroaralkenyl;
$Z^1$ is selected from halogen, lower alkyl, lower alkoxy, OH, haloalkyl, $NO_2$, nitrile, alkylthio, phenyl and -NR'R";
each of R' and R" is independently H, alkyl, OH or halo lower alkyl;
$Z^2$ is lower alkyl or halo lower alkyl;
$R^{22}$, $R^{23}$, $R^{24}$ and $R^{25}$ are each independently H or alkyl; or
(ii) $R^2$ and $R^{22}$, and/or $R^3$ and $R^{23}$, and/or $R^4$ and $R^{24}$, and/or $R^5$ and $R^{25}$ together form alkylene; and the remainder of $R^2$, $R^3$, $R^4$, $R^5$, $R^{22}$, $R^{23}$, $R^{24}$ and $R^{25}$ are selected as in (i);
Y is a tag group capable of being assayed by radiolabelled, photochemical, colorimetric, chromogenic, fluorescent, fluorogenic, phosphorescent, electrochemical, chemiluminescent or bioluminescent assays; and
$R^2$, $R^3$, $R^4$, $R^5$, X and Y are unsubstituted or are substituted with one or more substituents selected from Q, which, as defined herein, is halogen, hydroxy, nitrile, nitro, formyl, mercapto, carboxy, hydroxysulfonyl, hydroxyphosphoryl,alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkyl-aminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonyl-amino, azido, alkylthio, arylthio, perfluoroalkylthio, thiocyano, isothiocyano, alkylsulfinyl, alkylsulfonyl, arylsulfinyl, arylsulfonyl, aminosulfonyl, alkyl-aminosulfonyl, dialkylaminosulfonyl, arylaminosulfonyl or diarylaminosulfonyl, or any two Q groups substituting adjacent atoms on an aryl or heteroaryl group may form 1, 3-butadienylene, 1-aza-1, 3-butadienylene or 2-aza-1, 3-butadienylene. --

UNITED STATES PATENT AND TRADEMARK OFFICE
CERTIFICATE OF CORRECTION

PATENT NO. : 6,235,494 B1
DATED : May 22, 2001
INVENTOR(S) : Hugli

It is certified that error appears in the above-identified patent and that said Letters Patent is hereby corrected as shown below:

Please delete claim 47 and replace it with the following claim:
-- 47. The compound of claim 46, wherein $R^5$ and $R^{25}$ are selected from (i), (ii) or (iii) as follows:
    (i)     $R^5$ is the side chain of isoleucine, methionine, leucine, valine, alanine, glycine, serine or threonine; and $R^{25}$ is H or alkyl; or
    (ii)   $R^5$ and $R^{25}$ together form alkylene; or
    (iii)  $R^5$ is alkyl, alkenyl or alkynyl; and $R^{25}$ is selected as in (i). --

Please delete claim 48 and replace it with the following claim:
-- 48. The compound of claim 46, wherein $R^5$ and $R^{25}$ are selected from (i), (ii) or (iii) as follows:
    (i) $R^5$ is the side chain of isoleucine, methionine, leucine, valine, alanine, glycine, serine or threonine; and $R^{25}$ is H or alkyl; or
    (ii)   $R^5$ and $R^{25}$ together form alkylene; or
    (iii)  $R^5$ is alkyl, alkenyl or alkynyl; and $R^{25}$ is selected as in (i). --

Please delete claim 49 and replace it with the following claim:
-- 49. The compound of claim 46, wherein $R^3$ is the side chain of leucine. --

Please delete claim 50 and replace it with the following claim:
-- 50. The compound of claim 43, wherein X is alkylene or $CH(R^4)C(O)$ where $R^4$ is H. --

Please delete claim 51 and replace it with the following claim:
-- 51. The compound of claim 46, wherein X is alkylene or $CH(R^4)C(O)$ where $R^4$ is H. --

Please delete claim 52 and replace it with the following claim:
-- 52. The compound of claim 43, wherein Y is $SR^{13}$, $OR^{13}$ or $NR^{13}R^{14}$, where $R^{13}$ is alkyl, aryl, heteroaryl, aralkyl and heteroaralkyl and $R^{14}$ is H, alkyl, aryl, heteroaryl, aralkyl and heteroaralkyl, wherein $HSR^{13}$, $HOR^{13}$ and $HNR^{13}R^{14}$ are capable of being quantitatively assayed by radiolabelled, photochemical, colorimetric, chromogenic, fluorescent, fluorogenic, phosphorescent, electrochemical, chemiluminescent or bioluminescent assays. --

UNITED STATES PATENT AND TRADEMARK OFFICE
CERTIFICATE OF CORRECTION

PATENT NO. : 6,235,494 B1
DATED : May 22, 2001
INVENTOR(S) : Hugli

It is certified that error appears in the above-identified patent and that said Letters Patent is hereby corrected as shown below:

Please delete claim 53 and replace it with the following claim:
-- 53. The compound of claim 1, wherein Y is selected from 4-methyl coumaryl-7-amino, 4-trifluoromethyl coumaryl-7-amino, dansyl, naphthylamino, 7-oxy-coumaryl, 5-amino isophthalic acid diethyl ester, coumaryl-7-amino, 2-methyl-anthranilic acid, para-nitroanilino, para-nitrophenoxy, ortho-nitrophenoxy, ortho-carboxyphenoxy, nitrophenylamino, 1-carboxy-2-nitrophen-5-ylamino, 1 sulfo-2-nitrophen-5-ylamino, naphthylamino, $\mu$-naphthylamino, $\beta$-naphthylamino, nitronaphthylamino, 5-nitro-$a$-naphthylamino, riboflavin methoxynaphthylamino, 4-methoxy-$\mu$-naphthylamino, quinonylamino, a luminol, isoluminol, a luciferin, quinon-5-ylamino, nitroquinonylamino, 8-nitroquinon-5-ylamino, and naphthylamino tagged with radioactive halogen. --

Please delete claim 54 and replace it with the following claim:
-- 54. The compound of claim 43, wherein R and Y each comprise a detectable tag. --

Please delete claim 55 and replace it with the following claim:
-- 55. The compound of claim 54, wherein R is a fluorescent tag and Y comprises a colorimetric tag, wherein the fluorescence of R is quenched until cleavage of Y. --

Please delete claim 56 and replace it with the following claim:
-- 56. The method of claim 55, wherein R comprises 2-methyl-anthranilic acid. --

Please delete claim 57 and replace it with the following claim:
-- 57. The method of claim 56, where Y comprises pNA. --

Please delete claim 58 and replace it with the following claim:
-- 58. The compound of claim 43, wherein:
$R^1$ is the side chain of arginine or lysine;
$R^2$ is the side chain of alanine, glycine, glutamine, asparagine, threonine or norleucine;
$R^3$ is the side chain of leucine;
$R^4$ is the side chain of glycine, histidine, glutamine or leucine; and
$R^5$ is the side chain of alanine, leucine, isoleucine, methionine or valine. --

UNITED STATES PATENT AND TRADEMARK OFFICE
CERTIFICATE OF CORRECTION

PATENT NO. : 6,235,494 B1
DATED : May 22, 2001
INVENTOR(S) : Hugli

It is certified that error appears in the above-identified patent and that said Letters Patent is hereby corrected as shown below:

Please delete claim 59 and replace it with the following claim:
-- 59. The compound of claim 43 selected from the group consisting of R-Ala-Gly-Leu-Gln-Arg-Y, R-Ala-Gly-Leu-Asn-Arg-Y, R-Ala-Gly-Leu-Thr-Arg-Y, R-Ala-Gly-Leu-Nle-Arg-, R-Ala-Gly-Leu-Nle-Arg-Y, and R-Leu-Ala-Arg-Y. --

Please delete claim 60 and replace it with the following claim:
-- 60. The compound of claim 59 selected from the group consisting of Ac-Ala-Gly-Leu-Gln-Arg-pNA, Ac-Ala-Gly-Leu-Asn-Arg-pNA, Ac-Ala-Gly-Leu-Thr-Arg-pNA, Ac-Ala-Gly-Leu-Nle-Arg-pNA, Ac-Ala-Gly-Leu-Nle-Arg-pNA, and Ac-Leu-Ala-Arg-pNA. --

Please delete claim 61 and replace it with the following claim:
-- 61. The compound of claim 59, wherein Y is selected from the group consisting of 4-methylcoumaryl-7-amino, 4-trifluoromethylcoumaryl-7-amino, naphthylamino, 7-oxycoumaryl, 5-amino-iso-phthalic acid di(methyl or ethyl) ester, para-nitroanilino, para-nitrophenoxy, ortho-nitrophenoxy, ortho-carboxyphenoxy, nitrophenylamino, 1-carboxy-2-nitrophen-5-ylamino, 1-sulfo-2-nitrophen-5-ylamino, $\mu$-naphthylamino, $\beta$-naphthylamino, nitronaphthylamino, 5-nitro-$a$-naphthylamino, methoxynaphthylamino, 4-methoxy-$\mu$-naphthylamino, quinonylamino, quinon-5-ylamino, nitroquinonylamino and 8-nitroquinon-5-ylamino.--

Please delete claim 62 and replace it with the following claim:
-- 62. A kit, comprising:
    (a)      a first reagent, comprising a compound of claim 43; and
    (b)      a second reagent comprising an agent that inhibits the activity of a mannan-binding protein-associated serine protease (MASP). --

UNITED STATES PATENT AND TRADEMARK OFFICE
CERTIFICATE OF CORRECTION

PATENT NO. : 6,235,494 B1
DATED : May 22, 2001
INVENTOR(S) : Hugli

It is certified that error appears in the above-identified patent and that said Letters Patent is hereby corrected as shown below:

Please delete claim 63 and replace it with the following claim:
-- 63. The kit of claim 62, wherein the compound is on a solid support. --

Please delete claim 64 and replace it with the following claim:
-- 64. The method of claim 55, wherein the solid support is a microtiter plate. --

Signed and Sealed this

Nineteenth Day of February, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO. : 6,235,494 B1
DATED : May 22, 2001
INVENTOR(S) : Hugli

It is certified that error appears in the above-identified patent and that said Letters Patent is hereby corrected as shown below:

Column 1,
Line 5 please insert -- This invention was made with Government support under Contract No. Al 41670 by the National Institutes of Health. The Government has certain rights in this invention. --

Signed and Sealed this

Fourteenth Day of May, 2002

Attest:

Attesting Officer

JAMES E. ROGAN
Director of the United States Patent and Trademark Office

SEQUENCE LISTING

<160> NUMBER OF SEQ ID NOS: 19

<210> SEQ ID NO 1
<211> LENGTH: 77
<212> TYPE: PRT
<213> ORGANISM: Human C3a Anaphylatoxin

<400> SEQUENCE: 1

Ser Val Gln Leu Thr Glu Lys Arg Met Asn Lys Val Gly Lys Tyr Pro
 1               5                  10                  15

Lys Glu Leu Arg Lys Cys Cys Glu Asp Gly Met Arg Gln Asn Pro Met
            20                  25                  30

Arg Phe Ser Cys Gln Arg Arg Thr Arg Phe Ile Ser Leu Gly Glu Ala
        35                  40                  45

Cys Lys Lys Val Phe Leu Asp Cys Cys Asn Tyr Ile Thr Glu Leu Arg
    50                  55                  60

Arg Gln His Ala Arg Ala Ser His Leu Gly Leu Ala Arg
65                  70                  75

<210> SEQ ID NO 2
<211> LENGTH: 77
<212> TYPE: PRT
<213> ORGANISM: Pig C3a Anaphylatoxin

<400> SEQUENCE: 2

Ser Val Gln Leu Met Glu Lys Arg Met Asn Lys Leu Gly Gln Tyr Ser
 1               5                  10                  15

Lys Glu Leu Arg Arg Cys Cys Glu His Gly Met Arg Asn Asn Pro Met
            20                  25                  30

Lys Phe Ser Cys Gln Arg Arg Ala Gln Phe Ile His Gln Gly Asn Ala
        35                  40                  45

Cys Val Lys Ala Phe Leu Asn Cys Cys Glu Tyr Ile Ala Lys Leu Arg
    50                  55                  60

Gln Gln His Ser Arg Asn Lys Pro Leu Gly Leu Ala Arg
65                  70                  75

<210> SEQ ID NO 3
<211> LENGTH: 78
<212> TYPE: PRT
<213> ORGANISM: Rat C3a Anaphylatoxin

<400> SEQUENCE: 3

Ser Val Gln Leu Met Glu Arg Arg Met Asp Lys Ala Gly Gln Tyr Thr
 1               5                  10                  15

Asp Lys Gly Leu Arg Lys Cys Cys Glu Asp Gly Met Arg Asp Ile Pro
            20                  25                  30

Met Lys Tyr Ser Cys Gln Arg Arg Ala Arg Leu Ile Thr Gln Gly Glu
        35                  40                  45

Ser Cys Lys Leu Ala Phe Met Asp Cys Cys Asn Tyr Ile Thr Lys Leu
    50                  55                  60

Arg Glu Gln His Arg Arg Asp His Val Leu Gly Leu Ala Arg
65                  70                  75

<210> SEQ ID NO 4
<211> LENGTH: 78
<212> TYPE: PRT
<213> ORGANISM: Mouse C3a Anaphylatoxin -continued

```
<400> SEQUENCE: 4

Ser Val Gln Leu Met Glu Arg Arg Met Asp Lys Ala Gly Gln Tyr Thr
1               5                   10                  15

Asp Lys Gly Leu Arg Lys Cys Cys Glu Asp Gly Met Arg Asp Ile Pro
            20                  25                  30

Met Arg Tyr Ser Cys Gln Arg Arg Ala Arg Leu Ile Thr Gln Gly Glu
        35                  40                  45

Asn Cys Ile Lys Ala Phe Ile Asp Cys Cys Asn His Ile Thr Lys Leu
    50                  55                  60

Arg Glu Gln His Arg Arg Asp His Val Leu Gly Leu Ala Arg
65                  70                  75

<210> SEQ ID NO 5
<211> LENGTH: 78
<212> TYPE: PRT
<213> ORGANISM: Guinea Pig C3a Anaphylatoxin

<400> SEQUENCE: 5

Ser Val Gln Leu Met Glu Arg Arg Met Asp Lys Ala Gly Lys Tyr Lys
1               5                   10                  15

Ser Lys Glu Leu Arg Arg Cys Cys Glu Asp Gly Met Arg Glu Asn Pro
            20                  25                  30

Met Gln Phe Ser Cys Gln Arg Arg Ala Arg Tyr Val Ser Leu Gly Glu
        35                  40                  45

Ala Cys Val Lys Ala Phe Leu Asp Cys Cys Thr Tyr Met Ala Gln Leu
    50                  55                  60

Arg Gln Gln His Arg Arg Glu Gln Asn Leu Gly Leu Ala Arg
65                  70                  75

<210> SEQ ID NO 6
<211> LENGTH: 77
<212> TYPE: PRT
<213> ORGANISM: Human C4a Anaphylatoxin

<400> SEQUENCE: 6

Asn Val Asn Phe Gln Lys Ala Ile Asn Glu Lys Leu Gly Gln Tyr Ala
1               5                   10                  15

Ser Pro Thr Ala Lys Arg Cys Cys Gln Asp Gly Val Thr Arg Leu Pro
            20                  25                  30

Met Met Arg Ser Cys Glu Gln Arg Ala Ala Arg Val Gln Gln Pro Asn
        35                  40                  45

Cys Arg Glu Pro Phe Leu Ser Cys Cys Gln Phe Ala Glu Ser Leu Arg
    50                  55                  60

Lys Lys Ser Arg Asp Lys Gly Gln Ala Gly Leu Gln Arg
65                  70                  75

<210> SEQ ID NO 7
<211> LENGTH: 77
<212> TYPE: PRT
<213> ORGANISM: Cow C4a Anaphylatoxin

<400> SEQUENCE: 7

Asn Val Asn Phe Gln Lys Ala Ile His Glu Lys Leu Gly Gln Tyr Thr
1               5                   10                  15

Ser Pro Val Ala Lys Arg Cys Cys Gln Asp Gly Leu Thr Arg Leu Pro
            20                  25                  30

Met Met Arg Ser Cys Glu Gln Arg Ala Ala Arg Val Gln Gln Pro Ala
        35                  40                  45
```

-continued

```
Cys Arg Glu Pro Phe Leu Ser Cys Cys Gln Phe Ala Glu Ser Leu Arg
        50                  55                  60

Lys Ala Ser Ile Asp Lys Gly Val Ala Gly Leu Ala Arg
65                  70                  75

<210> SEQ ID NO 8
<211> LENGTH: 76
<212> TYPE: PRT
<213> ORGANISM: Rat C4a Anaphylatoxin
<220> FEATURE:
<221> NAME/KEY: CARBOHYD
<222> LOCATION: (66)...(68)

<400> SEQUENCE: 8

Asn Val Asn Phe Gln Lys Ala Ile Ser Glu Lys Leu Gly Gln Tyr Ser
1               5                   10                  15

Ser Pro Asp Thr Lys Arg Cys Cys Gln Asp Gly Met Thr Lys Leu Pro
            20                  25                  30

Met Ala Arg Thr Cys Glu Gln Arg Ala Ala Arg Val Pro Gln Pro Ala
        35                  40                  45

Cys Arg Glu Pro Phe Leu Ser Cys Cys Lys Phe Ala Glu Asp Leu Arg
    50                  55                  60

Arg Asn Gln Thr Arg Ser Gln Ile Gly Leu Ala Arg
65                  70                  75

<210> SEQ ID NO 9
<211> LENGTH: 76
<212> TYPE: PRT
<213> ORGANISM: Mouse C4a Anaphylatoxin
<220> FEATURE:
<221> NAME/KEY: CARBOHYD
<222> LOCATION: (66)...(68)

<400> SEQUENCE: 9

Asn Val Asn Phe Gln Lys Ala Val Asn Glu Lys Leu Gly Gln Tyr Ala
1               5                   10                  15

Ser Pro Thr Ala Lys Arg Cys Cys Gln Asp Gly Val Thr Arg Leu Pro
            20                  25                  30

Met Lys Arg Ser Cys Glu Gln Arg Ala Ala Gly Val Pro Gln Gln Ala
        35                  40                  45

Cys Arg Glu Pro Phe Leu Ser Cys Cys Lys Phe Ala Glu Ala Ile Arg
    50                  55                  60

Arg Asn Gln Thr Lys Ser Gln Ala His Leu Ala Arg
65                  70                  75

<210> SEQ ID NO 10
<211> LENGTH: 74
<212> TYPE: PRT
<213> ORGANISM: Human C5a Anaphylatoxin
<220> FEATURE:
<221> NAME/KEY: CARBOHYD
<222> LOCATION: (64)...(66)

<400> SEQUENCE: 10

Thr Leu Gln Lys Lys Ile Glu Glu Ile Ala Ala Lys Tyr Lys His Ser
1               5                   10                  15

Val Val Lys Lys Cys Cys Tyr Asp Gly Ala Cys Val Asn Asn Asp Glu
            20                  25                  30

Thr Cys Glu Gln Arg Ala Ala Arg Ile Ser Leu Gly Pro Arg Cys Ile
        35                  40                  45
```

```
Lys Ala Phe Thr Glu Cys Cys Val Ala Ser Gln Leu Arg Ala Asn
        50                  55                  60

Ile Ser His Lys Asp Met Gln Leu Gly Arg
65                  70
```

<210> SEQ ID NO 11
<211> LENGTH: 74
<212> TYPE: PRT
<213> ORGANISM: Pig C5a Anaphylatoxin
<220> FEATURE:
<221> NAME/KEY: CARBOHYD
<222> LOCATION: (64)...(66)

<400> SEQUENCE: 11

```
Met Leu Gln Lys Lys Ile Glu Glu Ala Ala Lys Tyr Lys Tyr Ala
1               5                   10                  15

Met Leu Lys Lys Cys Cys Tyr Asp Gly Ala Tyr Arg Asn Asp Asp Glu
                20                  25                  30

Thr Cys Glu Glu Arg Ala Ala Arg Ile Lys Ile Gly Pro Lys Cys Val
            35                  40                  45

Lys Ala Phe Thr Asp Cys Cys Tyr Val Ala Asn Gln Val Arg Ala Glu
        50                  55                  60

Gln Ser His Lys Asn Ile Gln Leu Gly Arg
65                  70
```

<210> SEQ ID NO 12
<211> LENGTH: 74
<212> TYPE: PRT
<213> ORGANISM: Cow C5a Anaphylatoxin

<400> SEQUENCE: 12

```
Met Leu Lys Lys Lys Ile Glu Glu Ala Ala Lys Tyr Arg Asn Ala
1               5                   10                  15

Trp Val Lys Lys Cys Cys Tyr Asp Gly Ala His Arg Asn Asp Asp Glu
                20                  25                  30

Thr Cys Glu Glu Arg Ala Ala Arg Ile Ala Ile Gly Pro Glu Cys Ile
            35                  40                  45

Lys Ala Phe Thr Ser Cys Cys Ala Val Ala Ser Gln Phe Arg Ala Asp
        50                  55                  60

Ile His His Lys Asn Ile Gln Leu Gly Arg
65                  70
```

<210> SEQ ID NO 13
<211> LENGTH: 77
<212> TYPE: PRT
<213> ORGANISM: Rat C5a Anaphylatoxin
<220> FEATURE:
<221> NAME/KEY: CARBOHYD
<222> LOCATION: (67)...(69)

<400> SEQUENCE: 13

```
Asp Leu Gln Leu Leu His Gln Lys Val Glu Glu Gln Ala Ala Lys Tyr
1               5                   10                  15

Lys His Arg Val Pro Lys Lys Cys Cys Tyr Asp Gly Ala Arg Glu Asn
                20                  25                  30

Lys Tyr Glu Thr Cys Glu Gln Arg Val Ala Arg Val Thr Ile Gly Pro
            35                  40                  45

His Cys Ile Arg Ala Phe Lys Glu Cys Cys Thr Ile Ala Asp His Ile
        50                  55                  60

Arg Lys Asn Glu Ser His Lys Gly Met Leu Leu Gly Arg
```

```
65                  70                  75

<210> SEQ ID NO 14
<211> LENGTH: 77
<212> TYPE: PRT
<213> ORGANISM: Mouse C5a Anaphylatoxin

<400> SEQUENCE: 14

Asn Leu His Leu Leu Arg Gln Lys Ile Glu Glu Ala Ala Lys Tyr
1               5                   10                  15

Lys His Ser Val Val Lys Lys Cys Cys Tyr Asp Gly Ala Arg Val Asn
                20                  25                  30

Phe Tyr Glu Thr Cys Glu Glu Arg Ala Ala Arg Val Ser Ile Gly Pro
            35                  40                  45

Leu Cys Ile Arg Ala Phe Asn Glu Cys Cys Val Val Ala Asn Lys Ile
        50                  55                  60

Arg Lys Glu Ser Pro His Lys Pro Val Gln Leu Gly Arg
65                  70                  75

<210> SEQ ID NO 15
<211> LENGTH: 5
<212> TYPE: PRT
<213> ORGANISM: MASP substrate

<400> SEQUENCE: 15

Ala Gly Leu Gln Arg
1               5

<210> SEQ ID NO 16
<211> LENGTH: 5
<212> TYPE: PRT
<213> ORGANISM: MASP substrate

<400> SEQUENCE: 16

Ala Gly Leu Asn Arg
1               5

<210> SEQ ID NO 17
<211> LENGTH: 5
<212> TYPE: PRT
<213> ORGANISM: MASP substrate

<400> SEQUENCE: 17

Ala Gly Leu Thr Arg
1               5

<210> SEQ ID NO 18
<211> LENGTH: 5
<212> TYPE: PRT
<213> ORGANISM: MASP substrate
<220> FEATURE:
<221> NAME/KEY: MOD_RES
<222> LOCATION: 4
<223> OTHER INFORMATION: Nle

<400> SEQUENCE: 18

Ala Gly Leu Xaa Arg
1               5

<210> SEQ ID NO 19
<211> LENGTH: 5
<212> TYPE: PRT
<213> ORGANISM: MASP substrate
```

-continued

```
<400> SEQUENCE: 19

Ala Gly Leu Gly Arg
1               5
```